(12) United States Patent
Gerlach et al.

(10) Patent No.: US 7,714,000 B2
(45) Date of Patent: May 11, 2010

(54) SUBSTITUTED PYRROLIDINONES AND THEIR USE AS MEDICAMENTS

(75) Inventors: Kai Gerlach, Biberach (DE); Henning Priepke, Warthausen (DE); Roland Pfau, Biberach (DE); Georg Dahmann, Attenweiler (DE); Wolfgang Wienen, Biberach (DE); Annette Schuler-Metz, Ulm (DE); Herbert Nar, Ochsenhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1116 days.

(21) Appl. No.: 11/276,247

(22) Filed: Feb. 21, 2006

(65) Prior Publication Data

US 2006/0217435 A1   Sep. 28, 2006

(30) Foreign Application Priority Data

Feb. 25, 2005   (DE)  .................. 10 2005 008 649

(51) Int. Cl.
*A61K 31/40* (2006.01)
*C07D 401/04* (2006.01)

(52) U.S. Cl. .................. 514/343; 514/423; 546/276.4; 548/517

(58) Field of Classification Search .................. None
See application file for complete search history.

(56) References Cited

FOREIGN PATENT DOCUMENTS

WO   WO03053925   7/2003
WO   WO2004110434   12/2004

OTHER PUBLICATIONS

Merderski, et al; Chlorothiophenecarboxamides as P1 surrogates of inhibitors of blood coagulation factor Xa; Bioorganic & Medicinal Chemistry Letters; Oxford, GB; Bd. 14, Nr. 23; Dec. 6, 2004; Seiten; pp. 5817-5822.
Ewing, et al; Design and Structure-Activity Relationships of Potent and Selective Inhibitors of Blood Coagulation Factor Xa; Journal of Medicinal Chemistry, American Chemical Society; Bd. 42, Nr. 18; Aug. 21, 1999; Seiten; pp. 3557-3571.

*Primary Examiner*—Zinna N Davis
(74) *Attorney, Agent, or Firm*—Michael P. Morris; Mary-Ellen M. Devlin; Edouard G. Lebel

(57) ABSTRACT

The present invention relates to new substituted pyrrolidinones of general formula

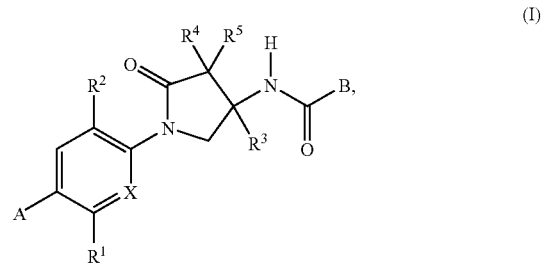

wherein A, X, B and $R^1$ to $R^9$ are defined as in claim 1, the tautomers, the enantiomers, the diastereomers, the mixtures thereof and the salts thereof, particularly the physiologically acceptable salts thereof with inorganic or organic acids or bases, which have valuable properties.

14 Claims, No Drawings

SUBSTITUTED PYRROLIDINONES AND THEIR USE AS MEDICAMENTS

The present invention relates to new substituted pyrrolidinones of general formula

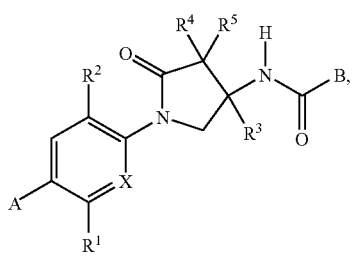

(I)

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

The present application relates to novel compounds of the above general formula I, the preparation thereof, the pharmaceutical compositions containing the pharmacologically effective compounds, the preparation and use thereof.

A first embodiment of the present invention comprises those compounds of general formula I, wherein A denotes a 4- to 7-membered cycloalkyleneiminocarbonyl or cycloalkyleneiminosulphonyl group, while
the cycloalkyleneimino moiety in the carbon skeleton may be substituted by one or two fluorine atoms, one or two $C_{1-3}$-alkyl, $C_{2-3}$-alkenyl, $C_{2-3}$-alkynyl, hydroxy-$C_{1-3}$-alkyl, $C_{1-3}$-alkyloxy-$C_{1-3}$-alkyl, phenyl-$C_{1-3}$-alkyl, 1,1-diphenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, trifluoromethylcarbonylamino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom, a sulphinyl or sulphonyl group or a methylene group in the 4-position of a 6- or 7-membered cycloalkyleneimino group may be replaced by an oxygen or sulphur atom, a carbonyl, sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the previously mentioned optionally substituted —NH group may be replaced by a carbonyl, sulphinyl or sulphonyl group, with the proviso that during the substitution of the previously mentioned 6- to 7-membered cycloalkyleneimino groups, wherein a methylene group is replaced by an oxygen or sulphur atom, a sulphinyl or sulphonyl group, two heteroatoms are separated from one another by at least two carbon atoms, a 5- to 7-membered cycloalkenyleneiminocarbonyl or cycloalkenyleneiminosulphonyl group optionally substituted by one or two $C_{1-3}$-alkyl, hydroxy-$C_{1-3}$-alkyl, $C_{1-5}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, wherein the double bond is not bound to a nitrogen atom and may be fused to a 5- or 6-membered heteroaryl group, an aminocarbonyl or aminosulphonyl group optionally substituted by one or two $C_{1-5}$-alkyl, $C_{2-3}$-alkenyl, $C_{2-3}$-alkynyl or $C_{3-6}$-cycloalkyl groups,
while the substituents may be identical or different and
in each case one of the $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-3}$-alkyl-aminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, or a group of formula

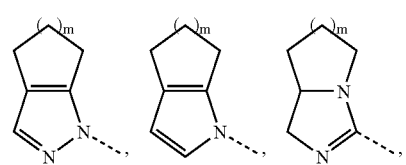

-continued which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkylsulphonyl, $C_{1-3}$-alkyl-sulphonyl-$C_{1-3}$-alkyl, aminosulphonyl, $C_{1-3}$-alkylsulphonyl-$C_{1-3}$-alkyl, $C_{1-3}$-alkylsulphonylamino-$C_{1-3}$-alkyl, $C_{1-3}$-alkylsulphonylamino, $C_{1-3}$-alkylcarbonylamino-$C_{1-3}$-alkyl, $C_{1-3}$-alkylcarbonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, hydroxy-$C_{1-3}$-alkyl, $C_{1-5}$-alkoxy-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH— group, $R^3$ denotes a hydrogen atom or a $C_{1-3}$-alkyl group, $R^4$ and $R^5$ each independently of one another denote
a hydrogen atom, a hydroxy group, an $OR^9$ group, a $C_{2-6}$-alkenyl or $C_{2-6}$-alkynyl group,
a straight-chain or branched $C_{1-6}$-alkyl group,
while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group,
while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to an above-mentioned—$NR^7$ group may be replaced by a carbonyl group,
a phenyl or heteroaryl group
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
a phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group,
a 3- to 7-membered cycloalkyl, cycloalkyleneimino, cycloalkyl-$C_{1-5}$-alkyl or cycloalkyleneimino-$C_{1-3}$-alkyl group,
wherein in 4- to 7-membered cyclic groups in the cyclic moiety a methylene group may optionally be replaced by an —N(R$^7$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N(R$^8$) or —S(O)$_2$N(R$^8$) group, or wherein in 6- to 7-membered cyclic groups in the cyclic moiety three adjacent methylene groups together may optionally be replaced by a substituted —OC(O)N (R$^8$) or —N(R$^8$)C(O)N(R$^8$) or —N(R$^8$)S(O)$_2$N(R$^8$) group, with the proviso that a 3- to 7-membered cycloalkyl, cycloalkyleneimino, cycloalkyl-C$_{1-5}$-alkyl or cycloalkyleneimino-C$_{1-3}$-alkyl group as hereinbefore defined wherein two heteroatoms selected from oxygen and nitrogen are separated from one another by precisely one optionally substituted —CH$_2$ group, is excluded, while a 3- to 7-membered cycloalkyl, cycloalkyleneimino, cycloalkyl-C$_{1-5}$-alkyl or cycloalkyleneimino-C$_{1-3}$-alkyl group as hereinbefore defined may be substituted at one or two —CH$_2$ groups by one or two C$_{1-3}$-alkyl groups in each case, with the proviso that R$^4$ and R$^5$ may not simultaneously be defined as hydroxy or OR$^9$ groups, or R$^4$ and R$^5$ together with the carbon atom to which they are bound form a C$_{3-8}$-cycloalkyl or C$_{3-8}$-cycloalkenyl group, while one of the methylene groups of a C$_{4-8}$-cycloalkyl group may be replaced by an oxygen or sulphur atom or a —N(R$^7$), or a carbonyl, sulphinyl or sulphonyl group, and/or two directly adjacent methylene groups of a C$_{4-8}$-cycloalkyl group may together be replaced by a —C(O)N (R$^8$) or —S(O)$_2$N(R$^8$) group, and/or three directly adjacent methylene groups of a C$_{6-8}$-cycloalkyl group may together be replaced by a —OC(O) N(R$^8$), —N(R$^8$)C(O)N(R$^8$) or —N(R$^8$)S(O)$_2$N(R$^8$) group, while 1 to 3 carbon atoms of a C$_{3-8}$-cycloalkyl group may optionally be substituted independently of one another by in each case one or two identical or different halogen atoms or C$_{1-5}$-alkyl, nitrile, hydroxy, C$_{1-5}$-alkyloxy, C$_{1-5}$-alkylcarbonyloxy, carboxy-C$_{1-5}$-alkyl, C$_{1-5}$-alkyloxycarbonyl-C$_{1-5}$-alkyl, C$_{1-5}$-alkylsulphanyl, C$_{1-5}$-alkylsulphonyl, carboxy, C$_{1-5}$-alkyloxycarbonyl, aminocarbonyl, C$_{1-5}$-alkylaminocarbonyl, di-(C$_{1-5}$-alkyl)-aminocarbonyl, C$_{3-6}$-cycloalkyleneiminocarbonyl, aminosulphonyl, C$_{1-5}$-alkylaminosulphonyl, di-(C$_{1-5}$-alkyl)-aminosulphonyl, C$_{3-6}$-cycloalkyleneiminosulphonyl, amino, C$_{1-5}$-alkylamino, di-(C$_{1-5}$-alkyl)-amino, C$_{1-5}$-alkylcarbonylamino, C$_{1-5}$-alkyl-sulphonylamino, N—(C$_{1-5}$-alkylsulphonyl)-C$_{1-5}$-alkylamino or C$_{3-6}$-cycloalkylcarbonylamino groups, while 1 to 2 carbon atoms of a C$_{3-8}$-cycloalkenyl group may optionally be substituted independently of one another by in each case a C$_{1-5}$-alkyl, nitrile, carboxy-C$_{1-5}$-alkyl, C$_{1-5}$-alkyloxycarbonyl-C$_{1-5}$-alkyl, carboxy, C$_{1-5}$-alkyloxycarbonyl, aminocarbonyl, C$_{1-5}$-alkylaminocarbonyl, di-(C$_{1-5}$-alkyl)-aminocarbonyl, C$_{3-6}$-cycloalkyleneiminocarbonyl, aminosulphonyl, C$_{1-5}$-alkylaminosulphonyl, di-(C$_{1-5}$-alkyl)-aminosulphonyl, C$_{3-6}$-cycloalkyleneiminosulphonyl groups, and 1 to 2 carbon atoms of a C$_{4-8}$-cycloalkenyl group which are not linked to another carbon atom by a double bond, may optionally be substituted independently of one another by a fluorine atom or a hydroxy, C$_{1-5}$-alkyloxy, C$_{1-5}$-alkylcarbonyloxy, C$_{1-5}$-alkylsulphanyl, C$_{1-5}$-alkylsulphonyl, amino, C$_{1-5}$-alkylamino, di-(C$_{1-5}$-alkyl)-amino, C$_{1-5}$-alkylcarbonylamino, C$_{1-5}$-alkylsulphonylamino, N—(C$_{1-5}$-alkylsulphonyl)-C$_{1-5}$-alkylamino or C$_{3-6}$-cycloalkylcarbonyl-amino groups, with the proviso that a C$_{3-8}$-cycloalkyl or C$_{3-8}$-cycloalkenyl group of this kind formed from R$^4$ and R$^5$ together, wherein two heteroatoms in the cyclic group comprising oxygen and nitrogen are separated from one another by precisely one optionally substituted —CH$_2$ group, and/or wherein one or both methylene groups of the cyclic group which are directly connected to the carbon atom to which the groups R$^4$ and R$^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one optionally substituted methylene group, and/or wherein two oxygen atoms are directly joined together, is excluded, R$^7$ in each case independently of one another denotes a hydrogen atom, a hydroxy, a formyl, a C$_{1-5}$-alkyl, C$_{1-5}$-alkylcarbonyl, C$_{1-5}$-alkyloxycarbonyl or C$_{1-5}$-alkylsulphonyl group, R$^8$ in each case independently of one another denotes a hydrogen atom or a C$_{1-5}$-alkyl group, R$^9$ denotes a straight-chain or branched C$_{1-6}$-alkyl group, while the hydrogen atoms of the straight-chain or branched C$_{1-6}$-alkyl group may optionally be wholly or partly replaced by fluorine atoms, and which may optionally be substituted by a C$_{3-5}$-cycloalkyl group, a hydroxy, a C$_{1-5}$-alkyloxy group, while the hydrogen atoms of the C$_{1-5}$-alkyloxy group may optionally be wholly or partly replaced by fluorine atoms, an allyloxy, propargyloxy, benzyloxy, C$_{1-5}$-alkylcarbonyloxy, C$_{1-5}$-alkyloxycarbonyloxy, carboxy-C$_{1-5}$-alkyloxy, C$_{1-5}$-alkyloxycarbonyl-C$_{1-5}$-alkyloxy, carboxy, C$_{1-5}$-alkyloxycarbonyl, aminocarbonyl, C$_{1-5}$-alkylaminocarbonyl, di-(C$_{1-5}$-alkyl)-aminocarbonyl, C$_{4-6}$-cycloalkyleneiminocarbonyl, C$_{1-5}$-alkyloxycarbonylamino, amino, C$_{1-5}$-alkylamino, di-(C$_{1-5}$-alkyl)-amino, C$_{1-5}$-alkylcarbonylamino, C$_{1-5}$-alkylsulphonylamino, N—(C$_{1-5}$-alkylsulphonyl)-C$_{1-5}$-alkylamino or C$_{3-6}$-cycloalkylcarbonyl-amino group, while the 6- to 7-membered cyclic groups of the C$_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —NR$^7$ group and additionally a methylene group adjacent to an above-mentioned —NR$^7$ group may be replaced by a carbonyl group, with the proviso that replacement of hydrogen atoms of the first carbon atom of the straight-chain or branched C$_{1-6}$-alkyl group by substituents from the group comprising oxygen, sulphur or nitrogen is excluded, a phenyl, heteroaryl, phenyl-C$_{1-5}$-alkyl or heteroaryl-C$_{1-5}$-alkyl group, which may optionally be mono- to trisubstituted in the phenyl or heteroaryl moiety by identical or different substituents selected from among halogen atoms, C$_{1-5}$-alkyl, di-(C$_{1-5}$-alkyl)-amino, hydroxy, C$_{1-5}$- alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$-alkyl group, wherein in 4- to 7-membered cyclic groups in the cyclic moiety a methylene group may optionally be replaced by a —N($R^7$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N($R^8$) or —S(O)$_2$N($R^8$) group, or wherein in 6- to 7-membered cyclic groups in the cyclic moiety three adjacent methylene groups together may optionally be replaced by a substituted —OC(O)N($R^8$) or —N($R^8$)C(O)N($R^8$) or —N($R^8$)S(O)$_2$N($R^8$) group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms selected from oxygen and nitrogen are separated from one another by precisely one optionally substituted —CH$_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —CH$_2$ groups by one or two $C_{1-3}$-alkyl groups in each case, B denotes a group of general formula

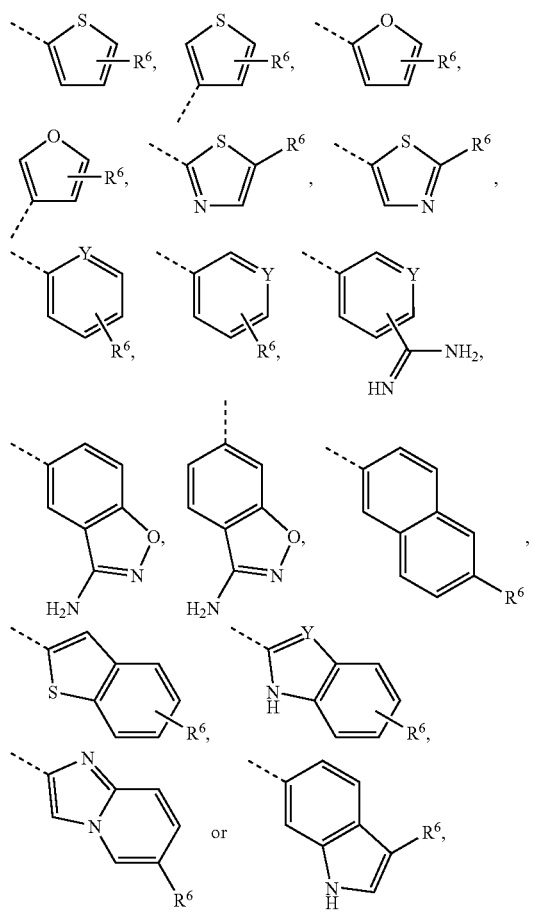

Y denotes a nitrogen or a CH— group, $R^6$ denotes a hydrogen, a halogen atom, a nitrile group, a $C_{2-3}$-alkenyl, $C_{2-3}$-alkynyl, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$ cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the afore-mentioned definitions which have more than two carbon atoms may unless otherwise stated be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated to the contrary, may be wholly or partly replaced by fluorine atoms, the tautomers, the enantiomers, the diastereomers, the mixtures thereof and the salts thereof.

A second embodiment of the present invention comprises those compounds of general formula I, wherein A denotes a 4- to 7-membered cycloalkyleneiminocarbonyl or cycloalkyleneiminosulphonyl group, while the cycloalkyleneimino moiety in the carbon skeleton may be substituted by one or two fluorine atoms, one or two $C_{1-3}$-alkyl, $C_{2-3}$-alkenyl, $C_{2-3}$-alkynyl, hydroxy-$C_{1-3}$-alkyl, $C_{1-3}$-alkyloxy-$C_{1-3}$-alkyl, phenyl-$C_{1-3}$-alkyl, 1,1-diphenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, trifluoromethylcarbonylamino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom, a sulphinyl or sulphonyl group or a methylene group in the 4-position of a 6- or 7-membered cycloalkyleneimino group may be replaced by an oxygen or sulphur atom, a carbonyl, sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the previously mentioned optionally substituted —NH group may be replaced by a carbonyl, sulphinyl or sulphonyl group, with the proviso that in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, a 5- to 7-membered cycloalkenyleneiminocarbonyl or cycloalkenyleneiminosulphonyl group optionally substituted by one or two $C_{1-3}$-alkyl, hydroxy-$C_{1-3}$-alkyl, $C_{1-5}$-alkoxy-$C_{1-3}$-alkyl, amino-$C_{1-3}$-alkyl, $C_{1-3}$-alkyl-amino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, $C_{2-3}$-alkenyl, $C_{2-3}$-alkynyl, or $C_{3-6}$-cycloalkyl groups, while the substituents may be identical or different and in each case one of the $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-3}$-alkyl-aminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, or a group of formula

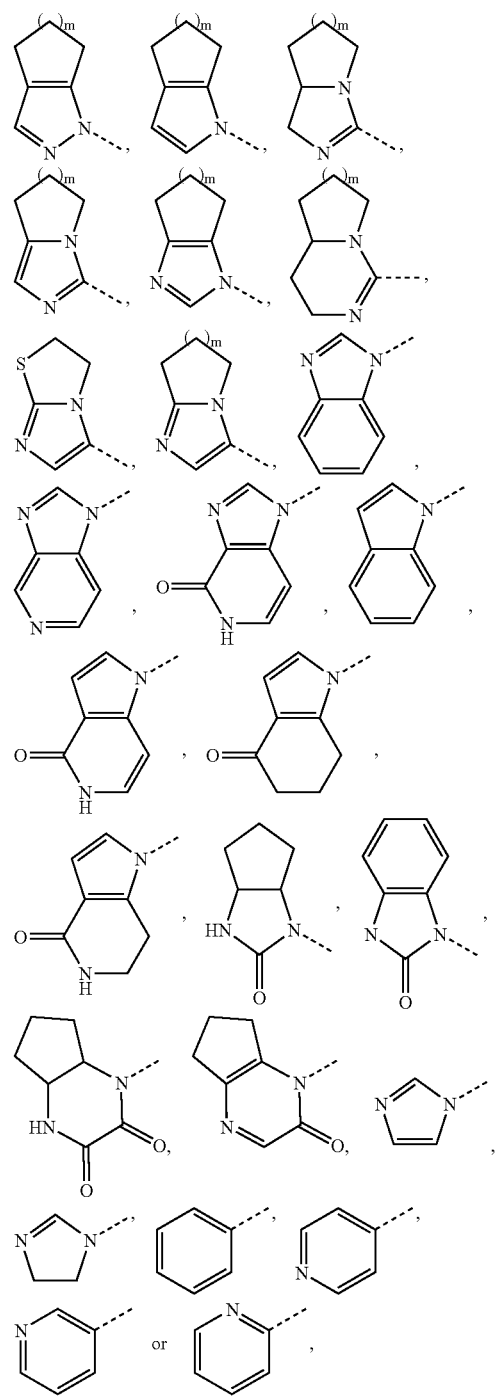

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkylsulphonyl, $C_{1-3}$-alkyl-sulphonyl-$C_{1-3}$-alkyl, aminosulphonyl, $C_{1-3}$-alkylsulphonyl-$C_{1-3}$-alkyl, $C_{1-3}$-alkylsulphonylamino-$C_{1-3}$-alkyl, $C_{1-3}$-alkylsulphonylamino, $C_{1-3}$-alkylcarbonylamino-$C_{1-3}$-alkyl, $C_{1-3}$-alkylcarbonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, hydroxy-$C_{1-3}$-alkyl, $C_{1-5}$-alkoxy-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH— group, $R^3$ denotes a hydrogen atom or a $C_{1-3}$-alkyl group, $R^4$ and $R^5$ each independently of one another denote
a hydrogen atom, a hydroxy group, an $OR^9$ group, a $C_{2-6}$-alkenyl or $C_{2-6}$-alkynyl group, a straight-chain or branched $C_{1-6}$-alkyl group,
while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group,
while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to an above-mentioned —$NR^7$ group may be replaced by a carbonyl group, a phenyl or heteroaryl group
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group, a 3- to 7-membered cycloalkyl, cycloalkyleneimino, cycloalkyl-$C_{1-5}$-alkyl or cycloalkyleneimino-$C_{1-3}$-alkyl group,
wherein in 4- to 7-membered cyclic groups in the cyclic moiety a methylene group may optionally be replaced by an —$N(R^7)$ group, an oxygen or sulphur atom or a —S(O) or —S(O)$_2$ group, or
wherein in 4- to 7-membered cyclic groups in the cyclic moiety two adjacent methylene groups together may optionally be replaced by a —$C(O)N(R^8)$ or —$S(O)_2N(R^8)$ group, or
wherein in 6- to 7-membered cyclic groups in the cyclic moiety three adjacent methylene groups together may optionally be replaced by a substituted —OC(O)N($R^8$) or —$N(R^8)C(O)N(R^8)$ or —$N(R^8)S(O)_2N(R^8)$ group,
with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms selected from oxygen and nitrogen are separated from one another by precisely one optionally substituted —$CH_2$ group, is excluded,
while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$ groups by one or two $C_{1-3}$-alkyl groups in each case,
with the proviso that $R^4$ and $R^5$ may not simultaneously be defined as hydroxy or $OR^9$ groups, or $R^4$ and $R^5$ together with the carbon atom to which they are bound form a $C_{3-8}$-cycloalkyl or $C_{3-8}$-cycloalkenyl group,
while one of the methylene groups of a $C_{4-8}$-cycloalkyl group may be replaced by an oxygen or sulphur atom or an —$N(R^7)$, or a carbonyl, sulphinyl or sulphonyl group, and/or
two directly adjacent methylene groups of a $C_{4-8}$-cycloalkyl group may together be replaced by a —$C(O)N(R^8)$ or —$S(O)_2N(R^8)$ group, and/or
three directly adjacent methylene groups of a $C_{6-8}$-cycloalkyl group may together be replaced by a —$OC(O)N(R^8)$, —$N(R^8)C(O)N(R^8)$ or —$N(R^8)S(O)_2N(R^8)$ group,
while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino groups,
while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not linked to another carbon atom by a double bond may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonyl-amino groups, with the proviso that a $C_{3-8}$-cycloalkyl or $C_{3-8}$-cycloalkenyl group of this kind formed from $R^4$ and $R^5$ together, wherein two heteroatoms in the cyclic group comprising oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one optionally substituted methylene group, and/or wherein two oxygen atoms are directly joined together, is excluded, $R^7$ each independently of one another denote a hydrogen atom, a hydroxy, a formyl, a $C_{1-5}$-alkyl, $C_{1-5}$-alkylcarbonyl, $C_{1-5}$-alkyloxycarbonyl or $C_{1-5}$-alkylsulphonyl group, $R^8$ each independently of one another denote a hydrogen atom or a $C_{1-5}$-alkyl group, $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonyl-amino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —NR$^7$ group and additionally a methylene group adjacent to an above-mentioned —NR$^7$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$-alkyl group, wherein in 4- to 7-membered cyclic groups in the cyclic moiety a methylene group may optionally be replaced by a —N(R$^7$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N(R$^8$) or —S(O)$_2$N(R$^8$) group, or wherein in 6- to 7-membered cyclic groups in the cyclic moiety three adjacent methylene groups together may optionally be replaced by a substituted —OC(O)N(R$^8$) or —N(R$^8$)C(O)N(R$^8$) or —N(R$^8$)S(O)$_2$N(R$^8$) group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms selected from oxygen and nitrogen are separated from one another by precisely one optionally substituted —CH$_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —CH$_2$ groups by one or two $C_{1-3}$-alkyl groups in each case, B denotes a group of general formula

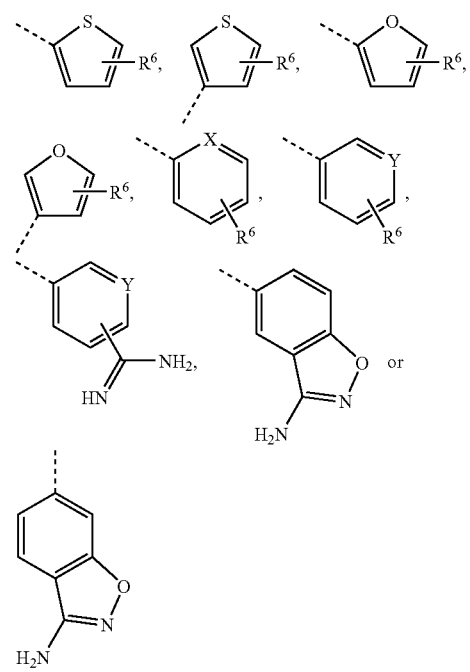

Y denotes a nitrogen atom or a CH— group, $R^6$ denotes a hydrogen, a halogen atom, a nitrile group, a $C_{2-3}$-alkenyl, $C_{2-3}$-alkynyl, a $C_{1-3}$-alkyl group, or a $C_{1-3}$- alkoxy group, while the hydrogen atoms of the $C_{1-3}$-alkyl or $C_{1-3}$-alkoxy group may optionally be wholly or partly replaced by fluorine atoms, while, unless otherwise stated, by the "heteroaryl group" mentioned hereinbefore in the definitions is meant a mono-cyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the afore-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated to the contrary, may be wholly or partly replaced by fluorine atoms, the tautomers, the enantiomers, the diastereomers, the mixtures thereof and the salts thereof.

A third embodiment of the present invention includes those compounds of general formula I, wherein A denotes a 4- to 7-membered cycloalkyleneiminocarbonyl or cycloalkyleneiminosulphonyl group, while the cycloalkyleneimino moiety in the carbon skeleton may be substituted by one or two fluorine atoms, one or two $C_{1-3}$-alkyl, $C_{2-3}$-alkenyl, $C_{2-3}$-alkynyl, hydroxy-$C_{1-3}$-alkyl, $C_{1-3}$-alkyloxy-$C_{1-3}$-alkyl, phenyl-$C_{1-3}$-alkyl, 1,1-diphenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, trifluoromethylcarbonylamino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- or 7-membered cycloalkyleneimino group may be replaced by an oxygen or sulphur atom, a carbonyl, sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the previously mentioned optionally substituted —NH group may be replaced by a carbonyl, sulphinyl or sulphonyl group, with the proviso that in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, a 5- to 7-membered cycloalkenyleneiminocarbonyl or cycloalkenyleneiminosulphonyl group optionally substituted by one or two $C_{1-3}$-alkyl, hydroxy-$C_{1-3}$-alkyl, $C_{1-5}$-alkoxy-$C_{1-3}$-alkyl, amino-$C_{1-3}$-alkyl, $C_{1-3}$-alkyl-amino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, $C_{2-3}$-alkenyl, $C_{2-3}$-alkynyl, or $C_{3-6}$-cycloalkyl groups, while the substituents may be identical or different and in each case one of the $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-3}$-alkyl-aminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, or a group of formula

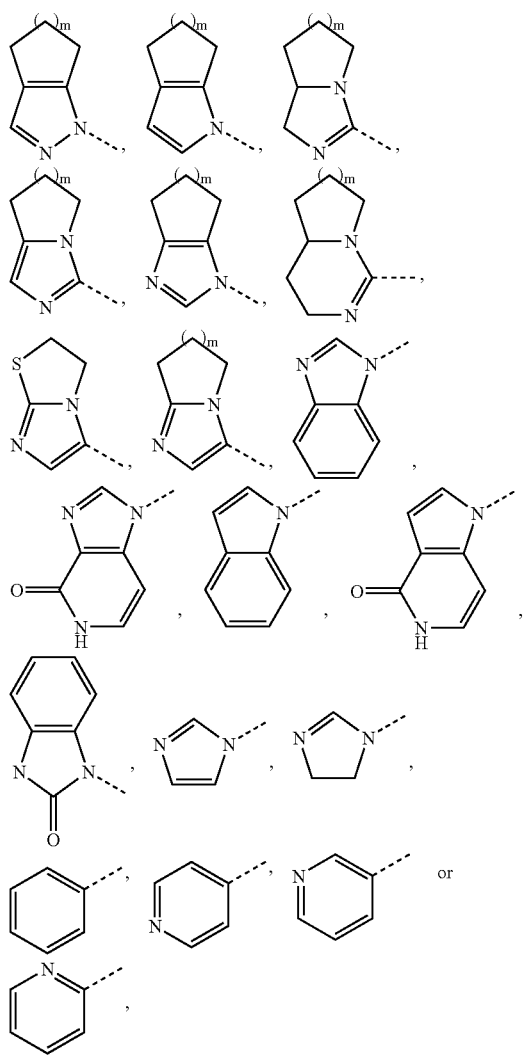

which may be substituted in each case at a carbon atom by
a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkylsulphonyl, $C_{1-3}$-alkyl-sulphonyl-$C_{1-3}$-alkyl, aminosulphonyl, $C_{1-3}$-alkylsulphonyl-$C_{1-3}$-alkyl, $C_{1-3}$-alkylsulphonylamino-$C_{1-3}$-alkyl, $C_{1-3}$-alkylsulphonylamino, $C_{1-3}$-alkylcarbonylamino-$C_{1-3}$-alkyl, $C_{1-3}$-alkylcarbonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, hydroxy-$C_{1-3}$-alkyl, $C_{1-5}$-alkoxy-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and
wherein
m denotes the number 1 or 2,
$R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group,
$R^2$ denotes a hydrogen or halogen atom or a methyl group,
X denotes a nitrogen atom or a CH— group,
$R^3$ denotes a hydrogen atom or a $C_{1-3}$-alkyl group,
$R^4$ and $R^5$ each independently of one another denote
a hydrogen atom, a hydroxy group, an $OR^9$ group, a $C_{2-6}$-alkenyl or $C_{2-6}$-alkynyl group,
a straight-chain or branched $C_{1-6}$-alkyl group,
while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group,
while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom or by a carbonyl, sulphinyl, sulphonyl or —$NR^7$ group and additionally a methylene group adjacent to an above-mentioned —$NR^7$ group may be replaced by a carbonyl group,
a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
a 3- to 7-membered cycloalkyl, cycloalkyleneimino, cycloalkyl-$C_{1-5}$-alkyl or cycloalkyleneimino-$C_{1-3}$-alkyl group,
wherein in 4- to 7-membered cyclic groups in the cyclic moiety a methylene group may optionally be replaced by a —$N(R^7)$ group, an oxygen or sulphur atom or a —S(O) or —$S(O)_2$ group, or
wherein in 4- to 7-membered cyclic groups in the cyclic moiety two adjacent methylene groups together may optionally be replaced by a —$C(O)N(R^8)$ or —$S(O)_2N(R^8)$ group, or
wherein in 6- to 7-membered cyclic groups in the cyclic moiety three adjacent methylene groups together may optionally be replaced by a substituted —OC(O)N($R^8$) or —$N(R^8)C(O)N(R^8)$ or —$N(R^8)S(O)_2N(R^8)$ group,
with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms selected from oxygen and nitrogen are separated from one another by precisely one optionally substituted —$CH_2$ group, is excluded,
while a 3- to 7-membered cycloalkyl, cycloalkyleneimino, cycloalkyl-$C_{1-5}$-alkyl or cycloalkyleneimino- $C_{1-3}$-alkyl group as hereinbefore defined may be substituted at one or two —$CH_2$ groups by one or two $C_{1-3}$-alkyl groups in each case, with the proviso that $R^4$ and $R^5$ may not simultaneously be defined as hydroxy or $OR^9$ groups, $R^7$ each independently of one another denote a hydrogen atom, a hydroxy, a formyl, a $C_{1-3}$-alkyl, $C_{1-3}$-alkylcarbonyl, $C_{1-3}$-alkyloxycarbonyl or $C_{1-3}$-alkylsulphonyl group, $R^8$ each independently of one another denote a hydrogen atom or a $C_{1-3}$-alkyl group $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to an above-mentioned —$NR^7$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a 3- to 7-membered cycloalkyl, cycloalkyl-$C_{1-5}$-alkyl or cycloalkyleneimino-$C_{2-3}$-alkyl group, wherein in 4- to 7-membered cyclic groups in the cyclic moiety a methylene group may optionally be replaced by an —$N(R^7)$ group, an oxygen or sulphur atom or a —$S(O)$ or —$S(O)_2$ group, or wherein in 4- to 7-membered cyclic groups in the cyclic moiety two adjacent methylene groups together may optionally be replaced by a —$C(O)N(R^8)$ or —$S(O)_2N(R^8)$ group, or wherein in 6- to 7-membered cyclic groups in the cyclic moiety three adjacent methylene groups together may optionally be replaced by a substituted —$OC(O)N(R^8)$ or —$N(R^8)C(O)N(R^8)$ or —$N(R^8)S(O)_2N(R^8)$ group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms selected from oxygen and nitrogen are separated from one another by precisely one optionally substituted —$CH_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —$CH_2$ groups by one or two $C_{1-3}$-alkyl groups in each case, B denotes a group of general formula

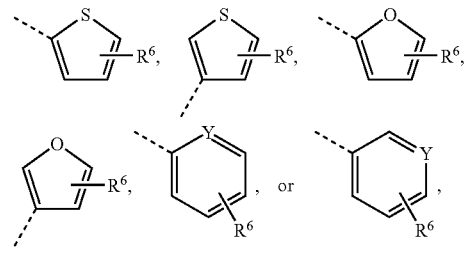

Y denotes a nitrogen atom or a CH— group, $R^6$ denotes a hydrogen, a halogen atom, an ethynyl, a methyl group, a methoxy group, while the hydrogen atoms of the methoxy group may optionally be wholly or partly replaced by fluorine atoms, while, unless otherwise stated, by the "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the afore-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated to the contrary, may be wholly or partly replaced by fluorine atoms, the tautomers, the enantiomers, the diastereomers, the mixtures thereof and the salts thereof.

A fourth embodiment of the present invention includes those compounds of general formula I, wherein A denotes a 4- to 7-membered cycloalkyleneiminocarbonyl or cycloalkyleneiminosulphonyl group, while the cycloalkyleneimino moiety in the carbon skeleton may be substituted by one or two fluorine atoms, one or two $C_{1-3}$-alkyl, hydroxy-$C_{1-3}$-alkyl, $C_{1-3}$-alkyloxy-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylamino-carbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- or 7-membered cycloalkyleneimino group may be replaced by an oxygen or sulphur atom, a sulphinyl or sulphonyl group or by an -NH group optionally substituted by a $C_{1-3}$-alkyl, hydroxy, formyl or $C_{1-3}$-alkylcarbonyl group, while additionally a methylene group adjacent to the previously mentioned optionally substituted —NH group may be replaced by a carbonyl, sulphinyl or sulphonyl group, with the proviso that in the substitution of the previously mentioned 6- to 7-membered cyclo-alkyleneimino groups, wherein a methylene group is replaced by an oxygen or sulphur atom, a sulphinyl or sulphonyl group, two heteroatoms are separated from one another by at least two carbon atoms, a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, or $C_{3-6}$-cycloalkyl groups, while the substituents may be identical or different and in each case one of the $C_{1-5}$-alkyl groups may be substituted by one or two hydroxy-$C_{1-3}$-alkyl, $C_{1-3}$-alkoxy-$C_{1-3}$-alkyl, amino-$C_{1-3}$-alkyl, di-($C_{1-3}$-alkyl)-amino-$C_{1-3}$-alkyl, a 4- to 7-membered cycloalkyleneimino-$C_{1-3}$-alkyl, aminocarbonyl, $C_{1-3}$-alkylamino-carbonyl, di-($C_{1-3}$-alkyl)-aminocarbonyl or a 4- to 7-membered cycloalkyleneiminocarbonyl group, or a group of formula

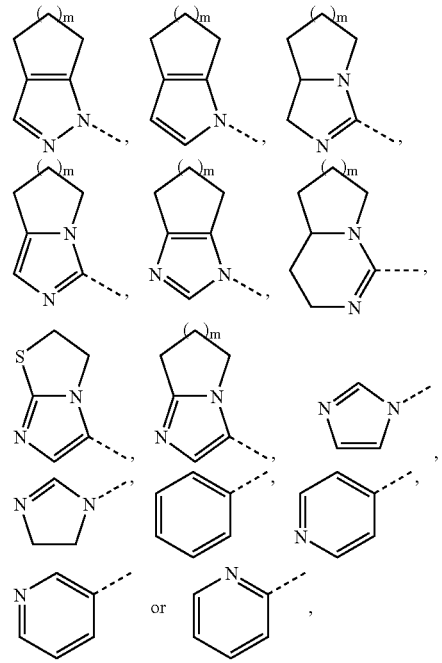

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkylsulphonyl, $C_{1-3}$-alkyl-sulphonyl-$C_{1-3}$-alkyl, aminosulphonyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, morpholin-4-yl-$C_{1-3}$- alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or fluorine atom or a methyl group, X denotes a nitrogen atom or a CH— group, $R^3$ denotes a hydrogen atom or a $C_{1-3}$-alkyl group, $R^4$ denotes a hydrogen atom, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{1-3}$-alkyloxy group, while the hydrogen atoms of the $C_{1-3}$-alkyloxy group may optionally be wholly or partly replaced by fluorine atoms, $R^5$ denotes a hydrogen atom, a hydroxy group, an $OR^9$ group, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to an above-mentioned —$NR^7$ group may be replaced by a carbonyl group a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, $R^7$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonyl-amino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to an above-mentioned —$NR^7$ group may be replaced by a carbonyl group with the proviso that the replacement of hydrogen atoms of the first carbon atom of the straight-chain or branched $C_{1-4}$-alkyl group by substituents from the group comprising oxygen, sulphur or nitrogen is excluded, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

B denotes a group of general formula

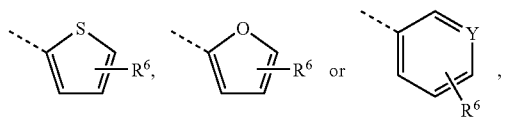

Y denotes a nitrogen atom or a CH— group, $R^6$ denotes a hydrogen, a halogen atom, an ethynyl, a methyl group, a methoxy group, while the hydrogen atoms of the methoxy group may optionally be wholly or partly replaced by fluorine atoms, while, unless otherwise stated, by the "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the afore-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated to the contrary, may be wholly or partly replaced by fluorine atoms, the tautomers, the enantiomers, the diastereomers, the mixtures thereof and the salts thereof.

A fifth embodiment of the present invention includes those compounds of general formula I wherein A denotes a 5- to 6-membered cycloalkyleneiminocarbonyl or cycloalkyleneiminosulphonyl group, while the cycloalkyleneimino moiety in the carbon skeleton may be substituted by one or two fluorine atoms, one or two $C_{1-3}$-alkyl, hydroxy-$C_{1-3}$-alkyl, $C_{1-3}$-alkyloxy-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a $C_{1-3}$-alkylcarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylamino-carbonyl, hydroxy, $C_{1-3}$-alkyloxy, amino, $C_{1-3}$-alkylamino, di-($C_{1-3}$-alkyl)-amino, N—($C_{1-3}$-alkyl)-piperazin-4-yl-$C_{1-3}$-alkyl, a phenyl or a 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- to 7-membered cycloalkyleneimino group may be replaced by an oxygen or sulphur atom or by an —NH group optionally substituted by a $C_{1-3}$-alkyl, hydroxy, formyl or $C_{1-3}$-alkylcarbonyl group, while additionally a methylene group adjacent to the previously mentioned optionally substituted —NH group may be replaced by a carbonyl group, with the proviso that in the substitution of the previously mentioned 6- to 7-membered cyclo-alkyleneimino groups, wherein a methylene group is replaced by an oxygen or sulphur atom, two heteroatoms are separated from one another by at least two carbon atoms, or A denotes a group of formula

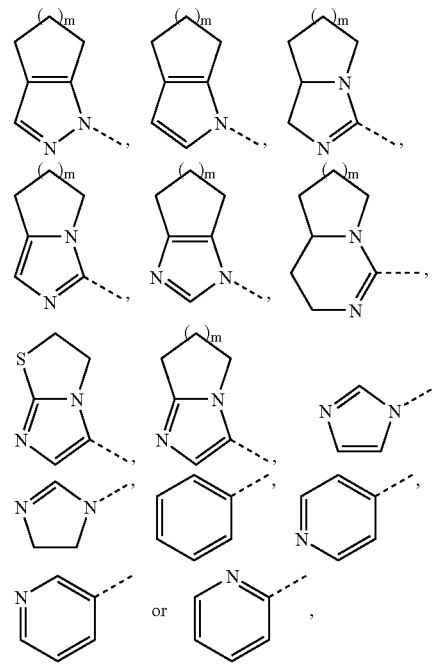

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkylsulphonyl, $C_{1-3}$-alkyl-sulphonyl-$C_{1-3}$-alkyl, aminosulphonyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen, fluorine, chlorine or bromine atom, a methyl or methoxy group, while the hydrogen atoms of the methyl or methoxy group may optionally be wholly or partly replaced by fluorine atoms, $R^2$ denotes a hydrogen or fluorine atom, X denotes a nitrogen atom or a CH— group, $R^3$ denotes a hydrogen atom or a $C_{1-3}$-alkyl group, $R^4$ denotes a hydrogen atom, $R^5$ denotes a hydrogen atom, a hydroxy group, an $OR^9$ group, a $C_{2-4}$-alkenyl or $C_{2-4}$-alkynyl group, a straight-chain or branched $C_{1-4}$-alkyl group, while the hydrogen atoms may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{4-6}$-cycloalkyleneiminocarbonyl, amino, $C_{1-3}$-alkylamino, di-($C_{1-3}$-alkyl)-amino, $C_{1-3}$-alkylcarbonylamino, or $C_{1-3}$-alkylsulphonylamino group, a phenyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, a phenyl-$C_{1-3}$-alkyl, heteroaryl-$C_{1-3}$-alkyl- group, while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, and which may optionally be substituted in the $C_{1-3}$-alkyl moiety by a hydroxy, a $C_{1-3}$-alkyloxy group, while the hydrogen atoms of the $C_{1-3}$-alkyloxy group may optionally be wholly or partly replaced by fluorine atoms, a $C_{1-5}$-alkylcarbonyloxy, or a $C_{1-5}$-alkyloxycarbonyloxy group;

$R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkyloxycarbonyl, aminocarbonyl, $C_{1-3}$-alkylaminocarbonyl, di-($C_{1-3}$-alkyl)-aminocarbonyl, $C_{4-6}$-cycloalkyleneiminocarbonyl, amino, $C_{1-3}$-alkylamino, di-($C_{1-3}$-alkyl)-amino, $C_{1-3}$-alkylcarbonylamino, $C_{1-3}$-alkyl-sulphonylamino group, with the proviso that the replacement of hydrogen atoms of the first carbon atom of the straight-chain or branched $C_{1-4}$-alkyl group by substituents from the group comprising oxygen, sulphur or nitrogen is excluded, a phenyl, phenyl-$C_{1-2}$-alkyl, heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, B denotes a group of general formula

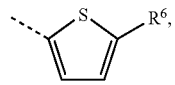

$R^6$ denotes a hydrogen, a chlorine or bromine atom, an ethynyl, a methyl or a methoxy group, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the afore-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated to the contrary, may be wholly or partly replaced by fluorine atoms, the tautomers, the enantiomers, the diastereomers, the mixtures thereof and the salts thereof.

A sixth embodiment of the present invention includes those compounds of general formula I, wherein A denotes a 5- to 6-membered cycloalkyleneiminocarbonyl or cycloalkyleneiminosulphonyl group, while the cycloalkyleneimino moiety may be substituted in the carbon skeleton by one or two $C_{1-3}$-alkyl, hydroxy-$C_{1-3}$-alkyl, $C_{1-3}$-alkyloxy-$C_{1-3}$-alkyl, pyridinyl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N-pyrrolidinyl-$C_{1-3}$-alkyl, $C_{1-3}$-alkyloxycarbonyl-$C_{1-3}$-alkyl, $C_{1-3}$-alkyloxycarbonyl, aminocarbonyl, $C_{1-3}$-alkylaminocarbonyl, di-($C_{1-3}$-alkyl)-aminocarbonyl, hydroxy, $C_{1-3}$-alkyloxy, $C_{1-3}$-alkylamino, di-($C_{1-3}$-alkyl)-amino, N—($C_{1-3}$-alkyl)-piperazin-4-yl-$C_{1-3}$-alkyl, a phenyl or a pyridinyl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- to 7-membered cycloalkyleneimino group may be replaced by an oxygen or sulphur atom, by an —NH group optionally substituted by a $C_{1-3}$-alkyl, hydroxy, formyl or $C_{1-3}$-alkylcarbonyl group, while additionally a methylene group adjacent to the previously mentioned optionally substituted -NH group may be replaced by a carbonyl group, with the proviso that in the substitution of the previously mentioned 6- to 7-membered cyclo-alkyleneimino groups wherein a methylene group is replaced by an oxygen or sulphur atom, two heteroatoms are separated from one another by at least two carbon atoms, or A denotes a group of formula

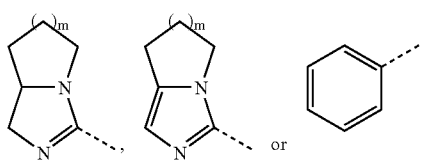

which may be substituted in each case at a carbon atom by a $C_{1-3}$-alkyl, methylsulphonylmethyl, aminosulphonyl, amino-$C_{1-3}$-alkyl, $C_{1-3}$-alkylamino-$C_{1-3}$-alkyl or a di-($C_{1-3}$-alkyl)-amino-$C_{1-3}$-alkyl group and wherein m denotes the number 1 or 2, $R^1$ denotes a hydrogen, fluorine, chlorine or bromine atom, a methyl, trifluoromethyl or methoxy group, $R^2$ denotes a hydrogen atom, X denotes a nitrogen atom or a CH— group, $R^3$ denotes a hydrogen atom or a methyl group, $R^4$ denotes a hydrogen atom, $R^5$ denotes a hydrogen atom, a hydroxy group, an $OR^9$ group, an allyl or methallyl group, a methyl group which may optionally be substituted by a $C_{1-3}$-alkyl, hydroxy, $OR^9$ group, aminocarbonyl, pyridin-4-yl, pyridin-3-yl, pyridin-2-yl, pyrazin-2-yl, pyrazin-3-yl or phenyl group, or a phenyl group, $R^9$ denotes a straight-chain or branched $C_{1-4}$-alkyl group, which may optionally be substituted by a hydroxy, a $C_{1-3}$-alkoxy group, a benzyloxy or a di-($C_{1-3}$-alkyl)-amino group, with the proviso that the replacement of hydrogen atoms of the first carbon atom of the straight-chain or branched $C_{1-4}$-alkyl group by substituents from the group oxygen or nitrogen is excluded, B denotes a group of general formula

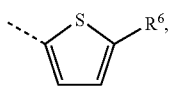

$R^6$ denotes a chlorine or bromine atom or an ethynyl group, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the afore-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated to the contrary, may be wholly or partly replaced by fluorine atoms, the tautomers, the enantiomers, the diastereomers, the mixtures thereof and the salts thereof.

A seventh embodiment of the present invention includes those compounds of general formula I, wherein the group B denotes the group

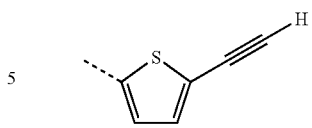

the tautomers, the enantiomers, the diastereomers, the mixtures thereof and the salts thereof.

An eighth embodiment of the present invention includes those compounds of general formula I, wherein the group B denotes the group

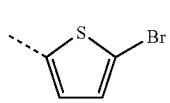

the tautomers, the enantiomers, the diastereomers, the mixtures thereof and the salts thereof.

A ninth embodiment of the present invention includes those compounds of general formula I, wherein the group A denotes the group

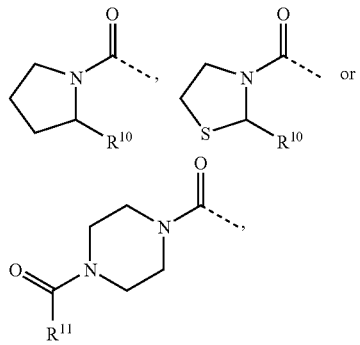

wherein $R^{10}$ denotes the hydrogen atom, a methyl, aminomethyl, $C_{1-3}$-alkylamino-$C_{1-2}$-alkyl, di-($C_{1-3}$-alkyl)-amino-$C_{1-2}$-alkyl, pyrrolidin-1-yl-methyl or 2-(pyrrolidin-1-yl)-ethyl group, $R^{11}$ denotes the hydrogen atom or a methyl group, the tautomers, the enantiomers, the diastereomers, the mixtures thereof and the salts thereof.

Within the scope of the present application unless otherwise defined, the following general terms mentioned in the definitions are more specifically defined as shown below or illustrated by Examples.

Examples of the monocyclic heteroaryl groups mentioned hereinbefore in the definitions are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of the bicyclic heteroaryl groups mentioned hereinbefore in the definitions are the benzimidazolyl, benzofuranyl, benzo[c]furanyl, benzothiophenyl, benzo[c]thiophenyl, benzothiazolyl, benzo[c]isothiazolyl, benzo[d]

isothiazolyl, benzooxazolyl, benzo[c]isoxazolyl, benzo[d]isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-6}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-i-en-3-yl, pent-2-en-3-yl, 2-methyl-but-i-en-1-yl, 2-methyl-but-2-en-1-yl, 2-methyl-but-3-en-1-yl, 2-ethyl-prop-2-en-1-yl, hex-1-en-2-yl, hex-2-en-2-yl, hex-3-en-2-yl, hex-4-en-2-yl, hex-5-en-2-yl, hex-i-en-3-yl, hex-2-en-3-yl, hex-3-en-3-yl, hex-4-en-3-yl, hex-5-en-3-yl, hex-1-en-4-yl, hex-2-en-4-yl, hex-3-en-4-yl, hex-4-en-4-yl, hex-5-en-4-yl, 4-methyl-pent-1-en-3-yl, 3-methyl-pent-1-en-3-yl, 2-methyl-pent-1-en-3-yl, 2,3-dimethyl-but-1-en-3-yl, 3,3-dimethyl-but-1-en-2-yl or 2-ethyl-but-1-en-3-yl group, Examples of the $C_{2-6}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-pentyn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

By a group which may be converted in vivo into a carboxy group is meant for example a carboxy group esterified with an alcohol wherein the alcoholic moiety is preferably a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bond to the oxygen atom starts from a carbon atom which carries a double or triple bond, a $C_{3-8}$-cycloalkyl-$C_{1-3}$-alkanol or an alcohol of formula

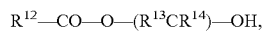

wherein
$R^{12}$ denotes a $C_{1-8}$-alkyl, $C_{5-7}$-cycloalkyl, phenyl or phenyl-$C_{1-3}$-alkyl group,
$R^{13}$ denotes a hydrogen atom, a $C_{1-3}$-alkyl, $C_{5-7}$-cycloalkyl or phenyl group and
$R^{14}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

By a group which may be converted in vivo into a hydroxyl group is meant for example a hydroxyl group esterified with a carboxylic acid wherein the carboxylic acid moiety is preferably a $C_{1-7}$-alkanoic acid, a phenyl-$C_{1-3}$-alkanoic acid, a $C_{3-9}$-cycloalkylcarboxylic acid, a $C_{5-7}$-cycloalkenecarboxylic acid, a $C_{3-7}$-alkenoic acid, a phenyl-$C_{3-5}$-alkenoic acid, a $C_{3-7}$-alkynoic acid or phenyl-$C_{3-5}$-alkynoic, while individual methylene groups of the carboxylic acid group may be replaced by oxygen atoms, with the proviso that no bond to the oxygen atom starts from a carbon atom which carries a double or triple bond.

Preferred groups which may be cleaved from a hydroxyl group in vivo include a $C_{1-7}$-acyl group such as the formyl, acetyl, n-propionyl, isopropionyl, n-propanoyl, n-butanoyl, n-pentanoyl, n-hexanoyl or cyclohexylcarbonyl group or a benzoyl group and also a methoxyacetyl, 1-methoxypropionyl, 2-methoxypropionyl or 2-methoxy-ethoxyacetyl group.

Those compounds of general formula I wherein A, $R^4$ and/or $R^5$ contains a group which may be converted in vivo into a carboxy or hydroxyl group are prodrugs for those compounds of general formula I wherein A, $R^4$ and/or $R^5$ contains a carboxy or hydroxyl group.

The following preferred compounds of general formula I will now be mentioned by way of example:

(1) 5-bromo-thiophene-2-carboxylic acid-{1-[3-methyl-4-(3-oxo-piperazine-1-carbonyl)-phenyl]-5-oxo-pyrrolidin-3-yl}-amide (2) 5-bromo-thiophene-2-carboxylic acid-{1-[4-(4-hydroxy-piperazine-1-carbonyl)-3-methyl-phenyl]-5-oxo-pyrrolidin-3-yl}-amide (3) (2S)-1-(4-{4-[(5-bromo-thiophene-2-carbonyl)-amino]-2-oxo-pyrrolidin-1-yl}-2-methyl-benzoyl)-pyrrolidine-2-carboxylic acid dimethylamide (4) methyl 1-(4-{4-[(5-bromo-thiophene-2-carbonyl)-amino]-2-oxo-pyrrolidin-1-yl}-2-methyl-benzoyl)-pyrrolidine-2-carboxylate (5) (2S)-1-(4-{4-[(5-bromo-thiophene-2-carbonyl)-amino]-2-oxo-pyrrolidin-1-yl}-2-methyl-benzoyl)-pyrrolidine-2-carboxylic acid methylamide (6) 5-bromo-thiophene-2-carboxylic acid-{1-[3-methyl-4-(3,4,5,6-tetrahydro-2H-[2,3']bipyridinyl-1-carbonyl)-phenyl]-5-oxo-pyrrolidin-3-yl}-amide (7) 5-bromo-thiophene-2-carboxylic acid-{1-[3-methyl-4-((2S)-2-pyrrolidin-1-ylmethyl-pyrrolidine-1-carbonyl)-phenyl]-5-oxo-pyrrolidin-3-yl}-amide (8) methyl 1-(4-{4-[(5-bromo-thiophene-2-carbonyl)-amino]-2-oxo-pyrrolidin-1-yl}-2-methyl-benzoyl)-piperidine-2-carboxylate (9) (2R)-1-(4-{4-[(5-bromo-thiophene-2-carbonyl)-amino]-2-oxo-pyrrolidin-1-yl}-2-methyl-benzoyl)-pyrrolidine-2-carboxylic acid amide

(10) 5-bromo-thiophene-2-carboxylic acid-(1-{4-[3-(butane-1-sulphonylamino)-piperidine-1-carbonyl]-3-methyl-phenyl}-5-oxo-pyrrolidin-3-yl)-amide

(11) 1-(4-{4-[(5-bromo-thiophene-2-carbonyl)-amino]-2-oxo-pyrrolidin-1-yl}-2-methyl-benzoyl)-piperidine-4-carboxylic acid amide

(12) 5-bromo-thiophene-2-carboxylic acid-{1-[3-methyl-4-(3-methyl-piperidine-1-carbonyl)-phenyl]-5-oxo-pyrrolidin-3-yl}-amide

(13) 5-bromo-thiophene-2-carboxylic acid-{1-[3-methyl-4-(4-methyl-piperidine-1-carbonyl)-phenyl]-5-oxo-pyrrolidin-3-yl}-amide
(14) 5-bromo-thiophene-2-carboxylic acid-(1-{4-[3-(3-butyl-ureido)-piperidine-1-carbonyl]-3-methyl-phenyl}-5-oxo-pyrrolidin-3-yl)-amide
(15) 5-bromo-thiophene-2-carboxylic acid-{1-[4-(dimethyl-carbamoylmethyl-methyl-carbamoyl)-3-methyl-phenyl]-5-oxo-pyrrolidin-3-yl}-amide
(16) 5-bromo-thiophene-2-carboxylic acid-(1-{4-[2-(4-dimethylamino-butyl)-piperidine-1-carbonyl]-3-methyl-phenyl}-5-oxo-pyrrolidin-3-yl)-amide
(17) methyl (2S,4R)-1-(4-{4-[(5-bromo-thiophene-2-carbonyl)-amino]-2-oxo-pyrrolidin-1-yl}-2-methyl-benzoyl)-4-hydroxy-pyrrolidine-2-carboxylate
(18) 5-bromo-thiophene-2-carboxylic acid-{1-[4-(R-2-hydroxymethyl-pyrrolidine-1-carbonyl)-3-methyl-phenyl]-5-oxo-pyrrolidin-3-yl}-amide
(19) 5-bromo-thiophene-2-carboxylic acid-{1-[4-(3,5-dimethyl-piperidine-1-carbonyl)-3-methyl-phenyl]-5-oxo-pyrrolidin-3-yl}-amide
(20) 5-bromo-thiophene-2-carboxylic acid-{1-[3-methyl-4-(thiomorpholine-4-carbonyl)-phenyl]-5-oxo-pyrrolidin-3-yl}-amide
(21) 5-bromo-thiophene-2-carboxylic acid-{1-[3-methyl-4-(2-methyl-morpholine-4-carbonyl)-phenyl]-5-oxo-pyrrolidin-3-yl}-amide
(22) 5-bromo-thiophene-2-carboxylic acid-{1-[3-methyl-4-(1-oxo-1$\lambda^4$-thiomorpholine-4-carbonyl)-phenyl]-5-oxo-pyrrolidin-3-yl}-amide
(23) 5-bromo-thiophene-2-carboxylic acid-(1-{3-methyl-4-[2-(4-methyl-piperazin-1-ylmethyl)-piperidine-1-carbonyl]-phenyl}-5-oxo-pyrrolidin-3-yl)-amide
(24) methyl 1-(4-{4-[(5-bromo-thiophene-2-carbonyl)-amino]-2-oxo-pyrrolidin-1-yl}-2-methyl-benzoyl)-piperidin-3-yl]acetate
(25) 5-bromo-thiophene-2-carboxylic acid-{1-[4-((2R)-2-methoxymethyl-pyrrolidine-1-carbonyl)-3-methyl-phenyl]-5-oxo-pyrrolidin-3-yl}-amide
(26) 5-bromo-thiophene-2-carboxylic acid-{1-[4-(3-hydroxy-piperidine-1-carbonyl)-3-methyl-phenyl]-5-oxo-pyrrolidin-3-yl}-amide
(27) 5-bromo-thiophene-2-carboxylic acid-{1-[4-((2S)-2-hydroxymethyl-pyrrolidine-1-carbonyl)-3-methyl-phenyl]-5-oxo-pyrrolidin-3-yl}-amide
(28) 5-bromo-thiophene-2-carboxylic acid-{1-[4-((2S)-2-methoxymethyl-pyrrolidine-1-carbonyl)-3-methyl-phenyl]-5-oxo-pyrrolidin-3-yl}-amide
(29) 5-bromo-thiophene-2-carboxylic acid-{1-[4-(4-methoxy-piperidine-1-carbonyl)-3-methyl-phenyl]-5-oxo-pyrrolidin-3-yl}-amide
(30) 5-bromo-thiophene-2-carboxylic acid-(1-{4-[2-(2-diethylamino-ethyl)-piperidine-1-carbonyl]-3-methyl-phenyl}-5-oxo-pyrrolidin-3-yl)-amide
(31) 5-bromo-thiophene-2-carboxylic acid-{1-[3-methyl-4-(2-methyl-pyrrolidine-1-carbonyl)-phenyl]-5-oxo-pyrrolidin-3-yl}-amide
(32) 5-bromo-thiophene-2-carboxylic acid-{1-[3-methyl-4-(4-methyl-[1,4]diazepan-1-carbonyl)-phenyl]-5-oxo-pyrrolidin-3-yl}-amide
(33) 5-bromo-thiophene-2-carboxylic acid-(1-{4-[2-(3-hydroxy-propyl)-piperidine-1-carbonyl]-3-methyl-phenyl}-5-oxo-pyrrolidin-3-yl)-amide
(34) 5-bromo-thiophene-2-carboxylic acid-{1-[3-methyl-4-(piperidine-1-carbonyl)-phenyl]-5-oxo-pyrrolidin-3-yl}-amide
(35) 5-bromo-thiophene-2-carboxylic acid-{1-[3-methyl-4-(2-methyl-piperidine-1-carbonyl)-phenyl]-5-oxo-pyrrolidin-3-yl}-amide
(36) 1-(4-{4-[(5-bromo-thiophene-2-carbonyl)-amino]-2-oxo-pyrrolidin-1-yl}-2-methyl-benzoyl)-piperidine-3-carboxylic acid amide
(37) 5-bromo-thiophene-2-carboxylic acid-{1-[4-(4-hydroxy-piperidine-1-carbonyl)-3-methyl-phenyl]-5-oxo-pyrrolidin-3-yl}-amide
(38) 5-bromo-thiophene-2-carboxylic acid-{1-[4-(4-acetyl-piperazine-1-carbonyl)-3-methyl-phenyl]-5-oxo-pyrrolidin-3-yl}-amide
(39) 5-bromo-thiophene-2-carboxylic acid-{1-[3-methyl-4-((2R)-2-phenylaminomethyl-pyrrolidine-1-carbonyl)-phenyl]-5-oxo-pyrrolidin-3-yl}-amide
(40) 5-bromo-thiophene-2-carboxylic acid-{1-[3-methyl-4-(morpholine-4-carbonyl)-phenyl]-5-oxo-pyrrolidin-3-yl}-amide
(41) 5-bromo-thiophene-2-carboxylic acid-{1-[3-methyl-4-(3-oxo-[1,4]diazepan-1-carbonyl)-phenyl]-5-oxo-pyrrolidin-3-yl}-amide
(42) 5-bromo-thiophene-2-carboxylic acid-{1-[3-methyl-4-(2-methyl-5-phenyl-pyrrolidine-1-carbonyl)-phenyl]-5-oxo-pyrrolidin-3-yl}-amide
(43) 5-bromo-thiophene-2-carboxylic acid-{1-[3-methyl-4-(4-methyl-piperazine-1-carbonyl)-phenyl]-5-oxo-pyrrolidin-3-yl}-amide
(44) 5-bromo-thiophene-2-carboxylic acid-{1-[4-(3,3-dimethyl-piperidine-1-carbonyl)-3-methyl-phenyl]-5-oxo-pyrrolidin-3-yl}-amide
(45) 5-bromo-thiophene-2-carboxylic acid-{1-[4-(2-ethyl-piperidine-1-carbonyl)-3-methyl-phenyl]-5-oxo-pyrrolidin-3-yl}-amide
(46) ethyl 1-(4-{4-[(5-bromo-thiophene-2-carbonyl)-amino]-2-oxo-pyrrolidin-1-yl}-2-methyl-benzoyl)-piperidine-3-carboxylate
(47) 5-bromo-thiophene-2-carboxylic acid-{1-[3-methyl-4-(thiazolidine-3-carbonyl)-phenyl]-5-oxo-pyrrolidin-3-yl}-amide
(48) 5-bromo-thiophene-2-carboxylic acid-[1-(4-{2-[(ethyl-methyl-amino)-methyl]-piperidine-1-carbonyl}-3-methyl-phenyl)-5-oxo-pyrrolidin-3-yl]-amide
(49) 5-bromo-thiophene-2-carboxylic acid-{1-[4-(3,6-dihydro-2H-pyridine-1-carbonyl)-3-methyl-phenyl]-5-oxo-pyrrolidin-3-yl}-amide
(50) 5-bromo-thiophene-2-carboxylic acid-(1-{4-[2-(3-dimethylamino-propyl)-piperidine-1-carbonyl]-3-methyl-phenyl}-5-oxo-pyrrolidin-3-yl)-amide
(51) 5-bromo-thiophene-2-carboxylic acid-{1-[4-(4-formyl-piperazine-1-carbonyl)-3-methyl-phenyl]-5-oxo-pyrrolidin-3-yl}-amide
(52) 5-bromo-thiophene-2-carboxylic acid-{1-[3-methyl-4-(2-piperidin-1-ylmethyl-piperidine-1-carbonyl)-phenyl]-5-oxo-pyrrolidin-3-yl}-amide
(53) 5-bromo-thiophene-2-carboxylic acid-{1-[4-(azepan-1-carbonyl)-3-methyl-phenyl]-5-oxo-pyrrolidin-3-yl}-amide
(54) 5-bromo-thiophene-2-carboxylic acid-{1-[3-methyl-4-(5-oxo-[1,4]diazepan-1-carbonyl)-phenyl]-5-oxo-pyrrolidin-3-yl}-amide
(55) 5-bromo-thiophene-2-carboxylic acid-{1-[4-(4-dimethylamino-piperidine-1-carbonyl)-3-methyl-phenyl]-5-oxo-pyrrolidin-3-yl}-amide
(56) 5-bromo-thiophene-2-carboxylic acid-{1-[3-methyl-4-(2-pyridin-2-yl-pyrrolidine-1-carbonyl)-phenyl]-5-oxo-pyrrolidin-3-yl}-amide

(57) 5-bromo-thiophene-2-carboxylic acid-{1-[3-methyl-4-(2-pyridin-4-yl-pyrrolidine-1-carbonyl)-phenyl]-5-oxo-pyrrolidin-3-yl}-amide

(58) 5-bromo-thiophene-2-carboxylic acid-{1-[3-methyl-4-((2S)-2-phenylaminomethyl-pyrrolidine-1-carbonyl)-phenyl]-5-oxo-pyrrolidin-3-yl}-amide

(59) 5-bromo-thiophene-2-carboxylic acid-{1-[4-(3-dimethylamino-pyrrolidine-1-carbonyl)-3-methyl-phenyl]-5-oxo-pyrrolidin-3-yl}-amide

(60) 5-bromo-thiophene-2-carboxylic acid-(1-{4-[3-(4-diethylamino-butyl)-piperidine-1-carbonyl]-3-methyl-phenyl}-5-oxo-pyrrolidin-3-yl)-amide

(61) 5-bromo-thiophene-2-carboxylic acid-{1-[4-(2-aminomethyl-piperidine-1-carbonyl)-3-methyl-phenyl]-5-oxo-pyrrolidin-3-yl}-amide

(62) 5-bromo-thiophene-2-carboxylic acid-{1-[4-((2R)-2-aminomethyl-pyrrolidine-1-carbonyl)-3-methyl-phenyl]-5-oxo-pyrrolid in-3-yl}-amide

(63) 5-bromo-thiophene-2-carboxylic acid-{1-[4-(3-aminomethyl-piperidine-1-carbonyl)-3-methyl-phenyl]-5-oxo-pyrrolidin-3-yl}-amide

(64) 5-bromo-thiophene-2-carboxylic acid-(1-{4-[(2S)-2-(2-amino-ethyl)-pyrrolidine-1-carbonyl]-3-methyl-phenyl}-5-oxo-pyrrolidin-3-yl)-amide

(65) 5-bromo-thiophene-2-carboxylic acid-{1-[3-methyl-4-(4-methylamino-piperidine-1-carbonyl)-phenyl]-5-oxo-pyrrolidin-3-yl}-amide

(66) 5-bromo-thiophene-2-carboxylic acid-{1-[4-(3-amino-pyrrolidine-1-carbonyl)-3-methyl-phenyl]-5-oxo-pyrrolidin-3-yl}-amide

(67) 5-bromo-thiophene-2-carboxylic acid-(1-{4-[3-(2-amino-ethyl)-piperidine-1-carbonyl]-3-methyl-phenyl}-5-oxo-pyrrolidin-3-yl)-amide

(68) 5-bromo-thiophene-2-carboxylic acid-{1-[4-([1.4]diazepan-1-carbonyl)-3-methyl-phenyl]-5-oxo-pyrrolidin-3-yl}-amide

(69) 5-bromo-thiophene-2-carboxylic acid-{1-[3-methyl-4-(4-methylaminomethyl-piperidine-1-carbonyl)-phenyl]-5-oxo-pyrrolidin-3-yl}-amide

(70) 5-bromo-thiophene-2-carboxylic acid-{1-[4-(4-amino-4-methyl-piperidine-1-carbonyl)-3-methyl-phenyl]-5-oxo-pyrrolidin-3-yl}-amide

(71) 5-bromo-thiophene-2-carboxylic acid-(1-{4-[2-(2-amino-ethyl)-piperidine-1-carbonyl]-3-methyl-phenyl}-5-oxo-pyrrolidin-3-yl)-amide

(72) 5-bromo-thiophene-2-carboxylic acid-{1-[4-(4-aminomethyl-piperidine-1-carbonyl)-3-methyl-phenyl]-5-oxo-pyrrolidin-3-yl}-amide

(73) 5-bromo-thiophene-2-carboxylic acid-(1-{4-[4-(3-ethylamino-propyl)-piperidine-1-carbonyl]-3-methyl-phenyl}-5-oxo-pyrrolidin-3-yl)-amide

(74) 5-bromo-thiophene-2-carboxylic acid-{1-[4-(dimethylcarbamoylmethyl-carbamoyl)-3-methyl-phenyl]-5-oxo-pyrrolidin-3-yl}-amide

(75) 5-bromo-thiophene-2-carboxylic acid-{1-[4-(1-dimethylcarbamoyl-2-methyl-propylcarbamoyl)-3-methyl-phenyl]-5-oxo-pyrrolidin-3-yl}-amide

(76) 5-bromo-thiophene-2-carboxylic acid-{1-[4-(carbamoylmethyl-carbamoyl)-3-methyl-phenyl]-5-oxo-pyrrolidin-3-yl}-amide

(77) 5-bromo-thiophene-2-carboxylic acid-{1-[4-(carbamoylmethyl-methyl-carbamoyl)-3-methyl-phenyl]-5-oxo-pyrrolidin-3-yl}-amide

(78) 5-bromo-thiophene-2-carboxylic acid-{1-[3-methyl-4-(methyl-methylcarbamoylmethyl-carbamoyl)-phenyl]-5-oxo-pyrrolidin-3-yl}-amide

(79) 5-bromo-thiophene-2-carboxylic acid-{1-[4-(cyclopropyl-methyl-carbamoyl)-3-methyl-phenyl]-5-oxo-pyrrolidin-3-yl}-amide

(80) 5-bromo-thiophene-2-carboxylic acid-(1-{4-[(2-amino-ethyl)-ethyl-carbamoyl]-3-methyl-phenyl}-5-oxo-pyrrolidin-3-yl)-amide

(81) 5-bromo-thiophene-2-carboxylic acid-(1-{3-methyl-4-[methyl-(2-methylamino-ethyl)-carbamoyl]-phenyl}-5-oxo-pyrrolidin-3-yl )-amide

(82) 5-bromo-thiophene-2-carboxylic acid-(1-{4-[(3-aminopropyl)-ethyl-carbamoyl]-3-methyl-phenyl}-5-oxo-pyrrolidin-3-yl)-amide

(83) 5-bromo-thiophene-2-carboxylic acid-{1-[3-methyl-4-(pyrrolidine-1-carbonyl)-phenyl]-5-oxo-pyrrolidin-3-yl}-amide

(84) 5-bromo-thiophene-2-carboxylic acid[1-(2'-dimethylaminomethyl-biphenyl-4-yl)-5-oxo-pyrrolidin-3-yl]amide

(85) 5-bromo-thiophene-2-carboxylic acid[1-(2'-dimethylaminomethyl-biphenyl-4-yl)-5-oxo-pyrrolidin-3-yl]amide

(86) 5-chloro-thiophene-2-carboxylic acid-[1-(2'-methanesulphonyl-biphenyl-4-yl)-5-oxo-pyrrolidin-3-yl]-amide

(87) 5-chloro-thiophene-2-carboxylic acid-[1-(2'-methanesulphonyl-biphenyl-4-yl)-5-oxo-pyrrolidin-3-yl]-amide

(88) 5-bromo-furan-2-carboxylic acid-[1-(2'-methanesulphonyl-biphenyl-4-yl)-5-oxo-pyrrolidin-3-yl]-amide

(89) 4-bromo-N-[1-(2'-methanesulphonyl-biphenyl-4-yl)-5-oxo-pyrrolidin-3-yl]-benzamide

(90) 4-chloro-N-[1-(2'-methanesulphonyl-biphenyl-4-yl)-5-oxo-pyrrolidin-3-yl]-benzamide

(91) 4-bromo-N-[1-(2'-dimethylaminomethyl-biphenyl-4-yl)-5-oxo-pyrrolidin-3-yl]-benzamide

(92) 4-chloro-N-[1-(2'-dimethylaminomethyl-biphenyl-4-yl)-5-oxo-pyrrolidin-3-yl]-benzamide

(93) (R)-5-bromo-thiophene-2-carboxylic acid-{1-[3-methyl-4-(pyrrolidine-1-sulphonyl)-phenyl]-5-oxo-pyrrolidin-3-yl}-amide

(94) (R)-5-ethynyl-thiophene-2-carboxylic acid-{1-[3-methyl-4-(pyrrolidine-1-sulphonyl)-phenyl]-5-oxo-pyrrolidin-3-yl}-amide

(95) 5-bromo-thiophene-2-carboxylic acid-{4-hydroxy-1-[3-methyl-4-(pyrrolidine-1-carbonyl)-phenyl]-5-oxo-pyrrolidin-3-yl}-amide

(96) 5-chloro-thiophene-2-carboxylic acid-{4-allyl-1-[3-methyl-4-(pyrrolidine-1-carbonyl)-phenyl]-5-oxo-pyrrolidin-3-yl}-amide

(97) 5-ethynyl-thiophene-2-carboxylic acid-{4-hydroxy-1-[3-methyl-4-(pyrrolidine-1-carbonyl)-phenyl]-5-oxo-pyrrolidin-3-yl}-amide

(98) 5-bromo-thiophene-2-carboxylic acid-{4-methoxy-1-[3-methyl-4-(pyrrolidine-1-carbonyl)-phenyl]-5-oxo-pyrrolidin-3-yl}-amide

(99) 5-bromo-thiophene-2-carboxylic acid-{4-(2-hydroxy-ethyl)-1-[3-methyl-4-(pyrrolidine-1-carbonyl)-phenyl]-5-oxo-pyrrolidin-3-yl}-amide (100) 5-bromo-thiophene-2-carboxylic acid-{4-(1,2-dihydroxy-ethyl)-1-[3-methyl-4-(pyrrolidine-1-carbonyl)-phenyl]-5-oxo-pyrrolidin-3-yl}-amide (101) 5-bromo-thiophene-2-carboxylic acid-1-[3-methyl-4-(5,6,7,7a-tetrahydro-1H-pyrrolo[1,2c]imidazol-3-yl)-phenyl]-5-oxo-pyrrolidin-3-yl}-amide (102) 5-bromo-thiophene-2-carboxylic acid-{1-[4-(6,7-dihydro-5H-pyrrolo[1,2c]imidazol-3-yl)-3-methyl-phenyl]-5-oxo-pyrrolidin-3-yl}-amide (103) 5-bromo-thiophene-2-carboxylic acid-{1-[4-(2,5-dihydropyrrole-1-carbonyl)-3-methyl-phenyl]-5-oxo-pyrrolidin-3-yl}-amide
(104) 5-bromo-thiophene-2-carboxylic acid-{4-methoxymethyl-1-[3-methyl-4-(pyrrolidine-1-carbonyl)-phenyl]-5-oxo-pyrrolidin-3-yl}-amide
(105) 5-chloro-thiophene-2-carboxylic acid-{4-propyl-1-[3-methyl-4-(pyrrolidine-1-carbonyl)-phenyl]-5-oxo-pyrrolidin-3-yl}-amide the tautomers, the enantiomers, the diastereomers, the mixtures thereof and the salts thereof.

Of the above-mentioned compounds the following compounds are particularly preferred:
(1), (2), (3), (4), (5), (6), (7), (8), (9), (10), (16), (17), (18), (20), (21), (23), (25), (27), (28), (29), (30), (31), (32), (33), (34), (37), (38), (39), (40), (41), (43), (46), (47), (48), (50), (51), (52), (53), (54), (56), (57), (58), (61), (62), (64), (65), (66), (67), (68), (69), (71), (2), (79), (80), (81), (82), (83), (84), (85), (86), (87), (93), (94), (95), (96), (97), (98), (99), (103), (104), (105), the tautomers, the enantiomers, the diastereomers, the mixtures thereof and the salts thereof.

Of the above-mentioned compounds the following compounds are most particularly preferred:
(7), (16), (18), (25), (27), (28), (30), (31), (33), (38), (39), (40), (41), (47), (51), (54), (58), (61), (62), (64), (83), (84), (85), (93), (94), (95), (96), (97), (98), (99), (104), (105), the tautomers, the enantiomers, the diastereomers, the mixtures thereof and the salts thereof.

Within the scope of the present application, if applicable, by the terms "isomer", "stereoisomer", "diastereomer", "enantiomer", "chiral", "racemate" or "racemic mixture" are meant the following. Compounds of the same empirical formula which differ in the nature or arrangement of the bonds of their atoms or their connectivity or the spatial arrangement of the atoms in the molecule, are referred to as "isomers". Isomers which while having the same nature and type of connectivity of their atoms differ in the spatial arrangement of the atoms in the molecule and are not congruent are known as "stereoisomers".

Stereoisomers which do not behave towards one another as image and mirror image are referred to as "diastereomers", and stereoisomers which do behave towards one another as image and mirror image are referred to as "enantiomers". When an asymmetrical centre or atom is present (also referred to as stereocentre or chiral centre), for example in a carbon atom substituted by four different substituents, the molecule is "chiral" in nature and a pair of enantiomers are possible. An enantiomer may be characterised by the absolute configuration of its stereocentre. The absolute configuration is described using the descriptors (R) and (S), which are determined by applying the sequence rules according to Cahn, Ingold and Prelog, or by describing the rotation of the plane of polarised light on interaction with the molecule, which is referred to as dextrorotatory or laevorotatory (i.e. with (+) or (−) as descriptor, accordingly). A chiral compound may occur both as an individual enantiomer or as a mixture of the corresponding enantiomers. A mixture which contains equal amounts of the two enantiomers of a compound is referred to as a "racemate" or "racemic mixture".

According to the invention the compounds of general formula (I) are obtained by methods known per se, for example by the following methods:

(a) In order to prepare a compound of general formula

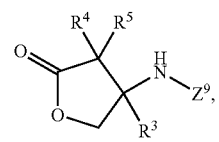

where $Z^9$ denotes a protective group of the amino function which may subsequently be cleaved by methods known from the literature, and $R^3$ to $R^5$ are as defined herein:

1) reduction and subsequent lactonisation of a compound of general formula

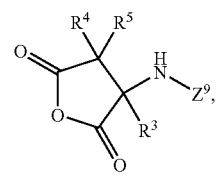

where $Z^9$ denotes a protective group of the amino function, which may subsequently be cleaved by methods known from the literature, and $R^3$ to $R^5$ are as defined herein:

The reduction to the intermediate hydroxy acid is for example conveniently carried out in a solvent or mixture of solvents such as tetrahydrofuran, dioxane, glycoldimethylether, diethyleneglycoldimethylether, pentane, hexane, cyclohexane, heptane, benzene, toluene or xylene with complex hydrides such as sodium borohydride, lithium borohydride, sodium cyanoborohydride, for example at temperatures between −80 and 250° C., but preferably between −30 and 150° C.

The subsequent lactonisation of the intermediate is conveniently carried out for example in a solvent or mixture of solvents such as benzene, chlorobenzene, toluene, xylene, dichloromethane, chloroform, tetrachloromethane, 1,2-dichloroethane, in the presence of a catalyst such as para-toluenesulphonic acid, camphorsulphonic acid or acid ion exchanger, optionally in the presence of a desiccant such as sodium sulphate, magnesium sulphate or molecular sieves, for example at temperatures between −30 and 250° C., but preferably between temperatures of 0 and 200° C. For example this reaction may be carried out as described by G. J. McGarvey, J. M. Williams, R. N. Hiner, Y. Matsubara, T. Oh *J. Am. Chem. Soc.* 1986, 108, 4943-4952.

2) (Sequential) alkylation of a compound of general formula

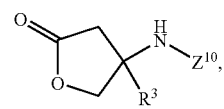

where $R^3$ is as defined herein and $Z^{10}$ denotes a protective group of the amino function, which may subsequently be cleaved by methods known from the literature, but may also represent an acyl group of formula

wherein B is as defined herein,
with a compound of general formula $$T-Z^{11} \quad (V),$$

wherein the group T denotes the groups $R^4$ or $R^5$ as defined herein, with the proviso that T cannot represent the group $OR^9$, and $Z^{11}$ denotes a nucleofugic group, for example an iodine, bromine or chlorine atom or a tosylate, triflate or mesylate group:

The alkylation may be repeated with an identical or different alkylating agent of formula (V), so as to obtain a,a-disubstituted lactones of compound (II). The alkylations may be carried out analogously to the conditions described under (a) 1) i) b) or as described by A. El Hadri, A. Ahbouabdellah, U. Thomet, R. Baur, R. Furtmuller, E. Sigel, W. Sieghart, R. H. Dodd, *J. Med. Chem.* 2002, 45, 2824-2831.

3) Nucleophilic substitution of a compound of general formula

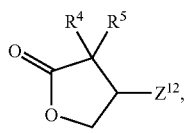

(VI)

wherein $Z^{12}$ denotes a nucleofugic group, for example an iodine, bromine or chlorine atom or a tosylate, triflate or mesylate group, and $R^4$ and $R^5$ are as defined herein, with a compound selected for example from among lithium-, sodium-, potassium azide, sodium-, potassium phthalimide, 4-methoxybenzylamine, benzylamine, 2,4-dimethoxybenzylamine, dibenzylamine, potassium or sodium cyanide, and subsequent reduction of the group thus introduced and manipulation of the protective groups.

The nucleophilic substitution is conveniently carried out in a solvent or mixture of solvents such as ethanol, isopropanol, benzene, chlorobenzene, toluene, xylene, glycol, glycol dimethylether, diethyleneglycol dimethylether, dimethylformamide, N-methylpyrrolidinone, tetraline, dimethylsulphoxide, sulpholane, methylene chloride, chloroform, tetrachloromethane or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between –30 and 250° C., but preferably between 0 and 150° C., optionally conveniently in the presence of bases such as lithium-, sodium-, potassium-, caesium carbonate, potassium-tert.-butoxide, sodium ethoxide, potassium hexamethyldisilazane, sodium hydride or lithium diisopropylamide. For example this reaction may be carried out as described by R. N. Salvatore, A. S. Nagle, K. W. Jung, *J. Org. Chem.* 2002, 67, 674-683.

The subsequent reduction of the nitrogen nucleophile thus introduced is carried out for example analogously to the method described in (a) 1).

The aminolactone thus obtained is provided with a protective group, for example, by methods known from the literature.

Compounds of formula (VI) may for example be prepared from malonic acids as described by J. -L. Canet, A. Fadel, J. Salaun, *J. Org. Chem.* 1992, 57, 3463-3473.

(c) In order to prepare a compound of general formula

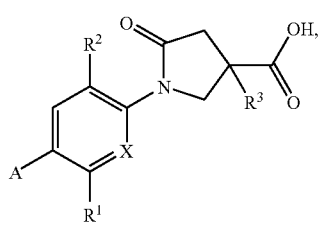

(VII)

wherein A, X and $R^1$ to $R^3$ are as defined herein:
tandem Michael addition/lactamisation of a compound of general formula

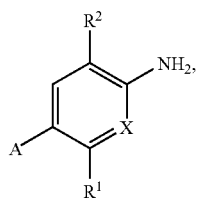

(VIII)

wherein A, X, $R^1$ and $R^2$ are as defined herein,
with itaconic acid and
optionally a subsequent sequence of esterification,
α-alkylation with a compound of general formula $$T^1-Z^{11} \quad (IX),$$

wherein $T^1$ denotes a $C_{1-3}$-alkyl group and $Z^{11}$ denotes a nucleofugic group, for example an iodine, bromine or chlorine atom or a tosylate, triflate or mesylate group, and unblocking of the carboxylic acid:

The tandem Michael addition/lactamisation is conveniently carried out with itaconic acid at a temperature of 50-250° C., but preferably at 80-200° C., in the presence or absence of a solvent or mixture of solvents such as water, ethanol, propanol, butanol, toluene, xylene, chlorobenzene, tetralin, diphenylether. This reaction makes it possible to synthesise compounds of general formula (VII) with the proviso that $R^3$ denotes a hydrogen atom.

Optional subsequent substitution is prepared for by blocking the carboxylic acid function by esterification using methods known from the literature.

The alkylation may be carried out analogously to the conditions described under (a) 1) i) b) or as described by X.-H. Jiang, Y.-L. Song, Y.-Q. Long, *Bioorg. Med. Chem. Lett.* 2004, 14, 3675-3678.

The unblocking of the esterified carboxylic acid by methods known from the literature makes it possible to prepare α-substituted carboxylic acids of general formula (VII), wherein $R^3$ then also denotes a $C_{1-3}$-alkyl group.

(d) In order to prepare a compound of general formula

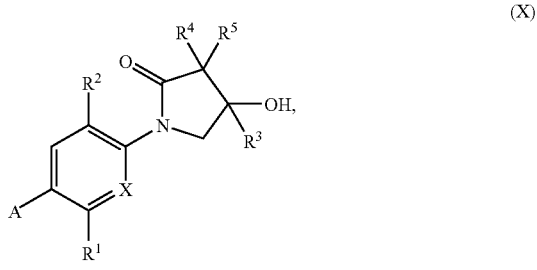
(X)

wherein A, X and $R^1$ to $R^5$ are as defined herein:
1) Transition metal-catalysed coupling reaction of a compound of general formula

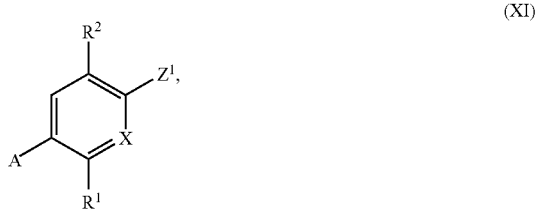
(XI)

wherein A, X, $R^1$ and $R^2$ are as defined herein and $Z^1$ denotes a chlorine, bromine or iodine atom or a triflate group, with a compound of general formula

(XII)

wherein $R^3$ to $R^5$ are as defined herein and $Z^{15}$ denotes a protective group for the hydroxy function, and subsequent unblocking of the hydroxy function:

The coupling reaction may for example be carried out analogously to the conditions described under (a) 1) a) ii).

The unblocking of the hydroxy function may be carried out using methods known from the literature.

The compounds of general formula (XI) may be prepared from the corresponding amines of general formula (VIII) by methods known from the literature such as for example the Sandmeyer reaction.

(e) In order to prepare a compound of general formula

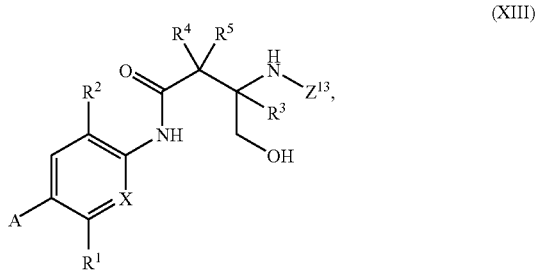
(XIII)

wherein A, X and $R^1$ to $R^5$ are as defined herein and $Z^{13}$ denotes a protective group of the amino function, which may subsequently be cleaved by methods known from the literature, but may also represent an acyl group of formula

wherein B is as defined herein:

Lewis acid-assisted lactone opening of a compound of general formula

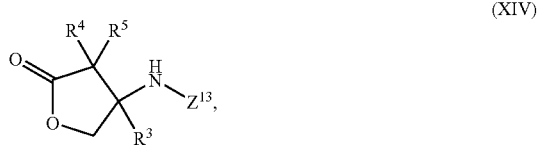
(XIV)

wherein $R^3$ to $R^5$ are as defined herein and $Z^{13}$ denotes a protective group for the amino function, which may subsequently be cleaved using methods known from the literature, but may also denote an acyl group of formula

wherein B is as defined herein,
with a compound of general formula

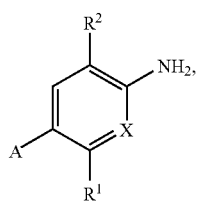
(VIII)

wherein A, X, $R^1$ and $R^2$ are as defined herein:

The compound of general formula (VIII) is activated with an organoaluminium compound such as for example trimethylaluminium, triethylaluminium, tripropylaluminium, triisobutylaluminium, tributylaluminium, triphenylaluminium in a solvent or mixture of solvents such as dichloromethane, toluene, xylene, benzene, hexane, cyclohexane, heptane, tetrahydrofuran, at a temperature of –100 to 100° C., but preferably between –80 and 80° C., and reacted with the lactone of general formula (XIV).

(f) In order to prepare a compound of general formula

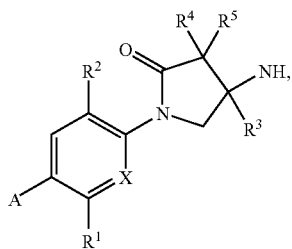

(XV)

wherein A, X and $R^1$ to $R^5$ are as defined herein:
1) nucleophilic ring opening of a compound of general formula

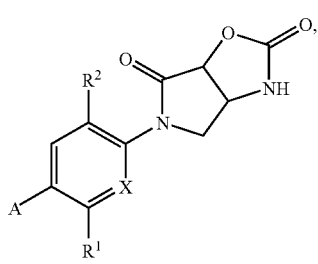

(XVI)

wherein A, X, $R^1$ and $R^2$ are as defined herein,
with an alkali metal salt of the compound $R^9OH$,
wherein $R^9$ is as defined herein:

The nucleophilic ring opening of the carbamate to form the free amine is conveniently carried out in a solvent or mixture of solvents such as water, methanol, ethanol, isopropanol, pentane, hexane, cyclohexane, heptane, benzene, toluene, xylene, glycol, glycol dimethylether, diethyleneglycol dimethylether, dioxane, tetrahydrofuran, N-methylpyrrolidinone, dimethylformamide with the lithium, sodium or potassium salt of the compound $R^9OH$, for example at temperatures between −30 and 250° C., but preferably between 0 and 150° C.

The compounds of formula (XVI) may for example be prepared as described by T. Kametani, Y. Kigawa, M. Ihara, *Tetrahedron.* 1979, 35, 313-316.

2) Acid breakdown reaction of a compound of general formula

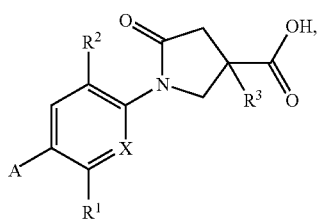

(VII)

wherein A, X, $R^1$ to $R^3$ are as defined herein:

The carboxylic acids are converted into, for example, activated carbonylamides or carbonylazides by methods known from the literature. By a rearrangement reaction (for example Hofmann, Lossen or Curtius rearrangement) these intermediates are converted into isocyanates.

The isocyanates thus formed are converted by reaction with an alcohol into the carbamates conventionally used as protective groups for the amine function.

These carbamate protective groups are subsequently cleaved using methods known from the literature and free the amine of formula (XV).

The isocyanates may optionally also be converted directly into the amine of formula (XV) under the effect of aqueous acid.

The preparation of the activated carboxylic acid derivatives may for example be carried out by activation of the above-mentioned carboxylic acids of formula (VII) as carbonylhalides or as asymmetric anhydrides with subsequent reaction with lithium-, sodium-, potassium azide or hydrazine or hydroxylamine in a solvent or mixture of solvents such as acetone, butanone, water, dimethylformamide, benzene, toluene, xylene, chlorobenzene, acetonitrile, nitromethane, tetrahydrofuran, dioxane, glycoldimethylether, diethyleneglycol dimethylether, dimethylformamide, N-methylpyrrolidinone, dimethylsulphoxide, sulpholane, methylene chloride, chloroform, tetrachloromethane, optionally in the presence of a base such as for example N-ethyldiisopropylamine, N—$C_{1-5}$-alkylmorpholine, N—$C_{1-5}$-alkylpiperidine, N—$C_{1-5}$-alkylpyrrolidine, triethylamine or pyridine, at temperatures between −80 and 250° C., but preferably between −30 and 150° C.

The acid breakdown reaction (i.e. rearrangement to form the isocyanate and carbamate) starting from the carboxylic acid of formula (VII) is conveniently carried out with diphenylphosphorylazide and a base such as for example N-ethyldiisopropylamine, N—$C_{1-5}$-alkylmorpholine, N—$C_{1-5}$-alkylpiperidine, N—$C_{1-5}$-alkylpyrrolidine, triethylamine, pyridine, in a solvent or mixture of solvents such as benzene, toluene, chlorobenzene, xylene, tetrahydrofuran, dioxane, glycol dimethylether, diethyleneglycol dimethylether, dimethylformamide, N-methylpyrrolidinone, dimethylsulphoxide, sulpholane, methylene chloride, chloroform or tetrachloromethane, at temperatures between −30 and 250° C., but preferably between 0 and 200° C., in the presence of an alcohol such as for example tert.-butanol, benzylalcohol, para-methoxybenzylalcohol and fluorenylmethanol.

These carbamate protective groups are subsequently cleaved using methods known from the literature and free the amine of formula (XV).

3) Mitsunobu cyclodehydration and subsequent cleaving of the protective groups from a compound of general formula

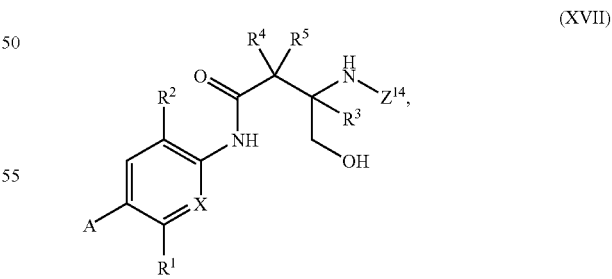

(XVII)

wherein A, X and $R^1$ to $R^5$ are as defined herein and $Z^{14}$ denotes a protective group for the amino function:

The lactamisation under Mitsunobo conditions is conveniently carried out in an inert solvent or mixture of solvents such as for example tetrahydrofuran, dioxane, benzene, toluene, xylene, acetonitrile in the presence of phosphines such as for example triphenylphosphine, tributylphosphine with dialkylazodicarboxylates such as for example diethyl azodicarboxylate, diisopropyl azodicarboxylate, di(tert.-butyl) azodicarboxylate, for example at a temperature of −50 to 200° C., but preferably between −20 and 150° C. The subsequent unblocking of the amino function may be carried out using methods described in the literature.

4) Activation, nucleophilic substitution and reduction of the thus introduced group of a compound of general formula

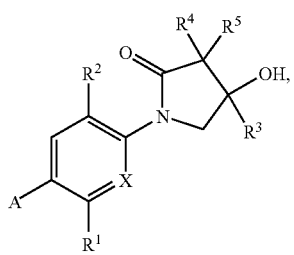
(X)

wherein A, X and $R^1$ to $R^5$ are as defined herein, and nucleophilic substitution with a compound selected for example from among lithium-, sodium-, potassium azide, sodium-, potassium phthalimide, 4-methoxybenzylamine, benzylamine, 2,4-dimethoxybenzylamine, dibenzylamine, potassium or sodium cyanide, and subsequent reduction of the nitrogen-containing group thus introduced:

The activation of the alcohol function of a compound of formula (X) is carried out using methods known from the literature such as for example transformation into a chlorine, bromine or iodine group or conversion into a nucleofugic group such as for example mesylate, triflate or tosylate.

The nucleophilic substitution with a nitrogen nucleophile and the subsequent reduction of the nitrogen nucleophile thus introduced is carried out for example analogously to the method described in (f) 3).

5) Reduction of the aliphatic nitro group of a compound of general formula

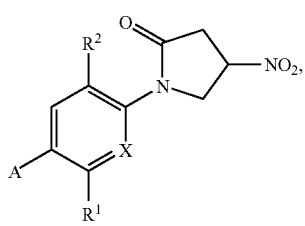
(XVIII)

wherein A, X, $R^1$ and $R^2$ are as defined herein:

The reduction of the nitro group is conveniently carried out in a solvent or mixture of solvents such as for example methanol, ethanol, isopropanol, propanol, butanol, water in the presence of transition metal salts such as for example nickel (II)chloride or cobalt(II)chloride with a reducing agent such as for example lithium borohydride, sodium borohydride, for example at a temperature of −80° C. to 150° C., but preferably between −20 and 100° C.

Compounds of general formula (XVIII) may be prepared analogously to the conditions described in (c) by a tandem Michael addition/lactamisation from compounds of general formula (VIII) by reaction with for example methyl 3-nitro-but-3-enoate.

(g) In order to prepare a compound of general formula

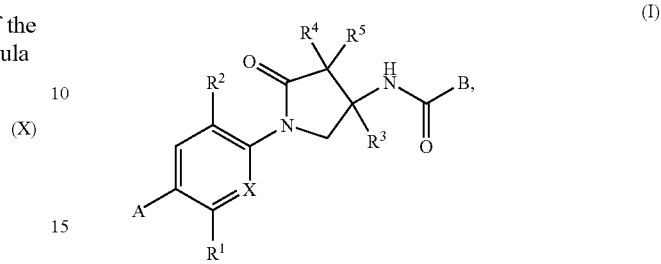
(I)

wherein A, X, B and $R^1$ to $R^5$ are as defined herein:

1) Mitsunobu cyclodehydration of a compound of general formula

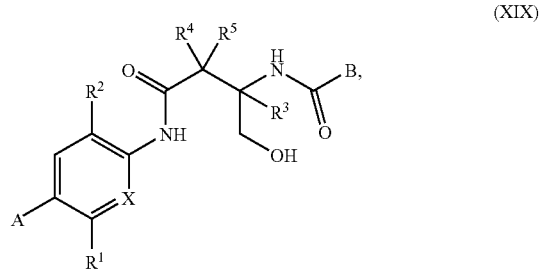
(XIX)

wherein A, X, B and $R^1$ to $R^5$ are as defined herein:

The lactamisation under Mitsunobu conditions is carried out for example 20 analogously to the method described in (e) 3).

2) Reduction of the aromatic nitro group, subsequent conversion of the amino group thus freed into the group A as defined herein and cleaving of the protective group from a compound of general formula

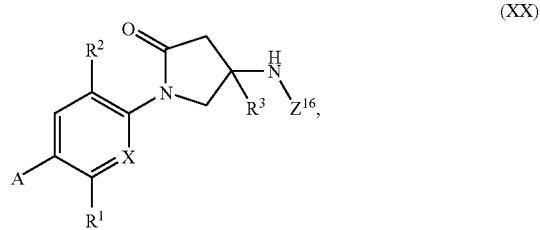
(XX)

wherein A, X and $R^1$ to $R^3$ are as defined herein are and $Z^{16}$ denotes a protective group for the amino function, by (sequential) alkylation analogously to the conditions described in (a) 1) i) b), by mono-hydroxylation with oxaziridines of the Davis type and optionally subsequent etherification or by aldol reaction with aldehydes of general formula

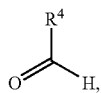

(XXI)

wherein R⁴ is as defined herein, while excluding the hydroxy group as the group R⁴.

The alkyation may be repeated with the same or a different alkylating agent, so as to obtain α, α-disubstituted lactams of the compound (XVIII).

In the alkylation, mono-hydroxylation and the aldol reaction the lactam of general formula (XX) may in each case be deprotonated analogously to the conditions described under (a) 1) i) b) and reacted with an electrophil such as e.g. an oxaziridine (for example phenylsulphonyloxaziridine or camphorsulphonyloxaziridine) or an aldehyde of general formula (XXI).

3) Acylation of a compound of general formula

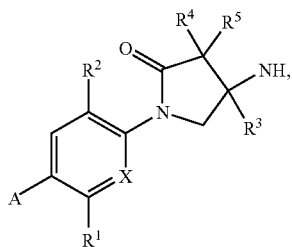

(XV)

wherein A, X, and $R^1$ to $R^5$ are as defined herein, with a carboxylic acid or a reactive carboxylic acid derivative of general formula

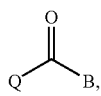

(XXII)

wherein B is as defined herein and Q denotes a hydroxy or $C_{1-4}$-alkoxy group, a halogen atom or an acyloxy group.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The acylation may however also be carried out with the free acid, optionally in the presence of an acid-activating agent or a dehydrating agent, for example in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole, N,N'-carbonyldiitriazole, O-(benzotriazol-1-yl)-N,N,N',N'-tetramethyl-uroniumtetrafluoroborate/N-methylmorpholine, O-(benzotriazol-1-yl)-N,N,N',N'-tetramethyl-uroniumtetrafluoroborate/N-ethyldiisopropylamine, O-pentafluorophenyl-N,N,N',N'-tetramethyluronium-hexafluorophosphate/triethylamine, N,N'-thionyldiimidazole or triphenylphosphine/carbon tetrachloride, at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff., Pergamon 1995.

In the reactions described hereinbefore any reactive groups present such as hydroxy, carboxy, amino, alkylamino or imino groups may be protected during the reaction by conventional protective groups which are cleaved again after the reaction.

For example a protecting group for a hydroxy group might be the methoxy, benzyloxy, trimethylsilyl, acetyl, benzoyl, tert.-butyl, trityl, benzyl or tetrahydropyranyl group, protecting groups for a carboxyl group might be the trimethylsilyl, methyl, ethyl, tert.-butyl, benzyl or tetrahydropyranyl group and a protecting group for an amino, alkylamino or imino group might be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

Other protective groups and their removal are described in T. W. Greene, P.G.M. Wuts, "Protective Groups in Organic Synthesis", Wiley, 1991 and 1999.

Any protective group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by means of ether splitting, e.g. in the presence of iodotrimethylsilane, at temperatures between 0 and 100° C., preferably at temperatures between 10 and 50° C.

A benzyl, methoxybenzyl or benzyloxycarbonyl group, however, is cleaved by hydrogenolysis, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and under a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.-butyl or tert.-butyloxycarbonyl group is preferably cleaved by treatment with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least two asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+) or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned hereinbefore, the compounds of general formula I and the tautomers, enantiomers, diastereomers and physiologically acceptable salts thereof have valuable pharmacological properties, particularly an antithrombotic activity which is preferably based on an effect on thrombin or factor Xa, for example on a thrombin-inhibiting or factor Xa-inhibiting activity, on a prolonging effect on the aPTT time and on an inhibitory effect on related serine proteases such as e.g. urokinase, factor VIIa, factor IX, factor XI and factor XII.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:
Tris(hydroxymethyl)-aminomethane buffer (100 mMol) and sodium chloride (150 mMol), pH 8.0 plus 1 mg/ml Human Albumin Fraction V, protease-free
Factor Xa (Calbiochem), spec. activity: 217 IU/mg, final concentration: 7 IU/ml for each reaction mixture
Substrate S 2765 (Chromogenix), final concentration: 0.3 mMol/l (1 KM) for each reaction mixture
Test substance: final concentration 100, 30, 10, 3, 1, 0.3, 0.1, 0.03, 0.01, 0.003, 0.001 µMol/l Procedure:
10 µl of a 23.5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation and severe sepsis, for the prevention and prophylaxis of DVT in patients with exacerbated COPD, for treating ulcerative colitis, for preventing and treating coronary thrombosis, for preventing stroke and the prevention of occlusion of shunts. In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. in the treatment of pulmonary fibrosis, for preventing and treating rheumatoid arthritis, for preventing or averting fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples that follow are intended to illustrate the invention, without restricting its scope:

As a rule, melting points, IR, UV, $^1$H-NMR and/or mass spectra have been obtained for the compounds prepared. Unless otherwise stated, $R_f$ values were determined using ready-made silica gel 60 $F_{254}$ TLC plates (E. Merck, Darmstadt, Item no.1.05714) without chamber saturation. The $R_f$ values given under the heading Alox were determined using ready-made aluminium oxide 60 $F_{254}$ TLC plates (E. Merck, Darmstadt, Item no.1.05713) without chamber saturation. The $R_f$ values given under the heading Reversed-phase-8 (RP-8) were determined using ready-made RP-8 $F_{254s}$ TLC plates (E. Merck, Darmstadt, Item no.1.15684) without chamber saturation. The ratios given for the eluants refer to units by volume of the solvents in question. For chromato-graphic purification silica gel made by the company Millipore (MATREX™, 35-70 μm) was used. Unless more detailed information is provided as to the configuration, it is not clear whether the products are pure stereoisomers or mixtures of enantiomers and diastereomers.

The following abbreviations are used in the descriptions of the experiments:

| | |
|---|---|
| Boc | tert.-butoxycarbonyl |
| DCC | N,N'-dicyclohexylcarbodiimide |
| DIPEA | N-ethyl-diisopropylamine |
| DMSO | dimethylsulphoxide |
| DMF | N,N-dimethylformamide |
| DPPA | diphenylphosphorylazide |
| sat. | saturated |

-continued

| | |
|---|---|
| i. vac. | in vacuo |
| conc. | concentrated |
| NMM | N-methyl-morpholine |
| NMP | N-methyl-pyrrolidin-2-one |
| o | ortho |
| PfTU | O-pentafluorophenyl-N,N,N',N'-tetramethyluronium-hexafluorophosphate |
| PPA | propanephosphonic acid cycloanhydride |
| quant. | quantitative |
| $R_f$ | retention factor |
| $R_t$ | retention time |
| rac. | racemic |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |
| tert. | tertiary |
| Σ | yield over all the steps described, carried out analogously |

The HPLC/MS data for Examples 2 to 82 were obtained under the following conditions:

Waters ZQ2000 mass spectrometer (mass range: 120-1000 m/z), HP 1100

HPLC+DAD, Gilson 215 Autosampler

The mobile phase used is:

A: water with 0.10% TFA

B: acetonitrile with 0.10% TFA

| time in min | % A | % B | flow rate in ml/min |
|---|---|---|---|
| 0.0 | 95 | 5 | 1.00 |
| 0.4 | 95 | 5 | 1.00 |
| 4.0 | 2 | 98 | 1.00 |
| 4.35 | 2 | 98 | 1.00 |
| 4.5 | 95 | 5 | 1.00 |

The stationary phase used was an XTerra® column, MS $C_{18}$ 3.5 μm, 4.6 mm×50 mm (column temperature: constant at 40° C.).

The diode array detection was carried out at a wavelength range of 210-500 nm.

The HPLC data for all the other Examples were obtained under the following conditions:

Waters ZMD, Alliance 2695 HPLC, Waters 2700 Autosampler, Waters 2996 Diode array detector The mobile phase used was:

A: water with 0.10% TFA

B: acetonitrile with 0.10% TFA

| time in min | % A | % B | flow rate in ml/min |
|---|---|---|---|
| 0.0 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

EXAMPLE 1

5-bromo-thiophene-2-carboxylic acid-{1-[3-methyl-4-(3-oxo-piperazine-1-carbonyl)-phenyl]-5-oxo-pyrrolidin-3-yl}-amide

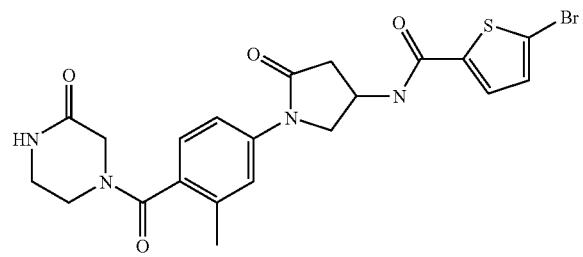

(a) methyl 4-amino-2-methyl-benzoate 15 g (78 mmol) 4-acetamido-2-methyl-benzoic acid are suspended in 150 ml of methanol and combined with 11.2 ml (210 mmol) conc. sulphuric acid. The mixture is refluxed for three hours. Then excess methanol is eliminated in vacuo. The residue is poured onto ice water, made alkaline with 5 N sodium hydroxide solution and extracted twice with ethyl acetate. The combined organic phases are dried over sodium sulphate and evaporated to dryness.

Yield: quantitative $R_t$ value: 2.0 min $C_9H_{11}NO_2$ (165.19) Mass spectrum: $(M+H)^{30}$ =166

(b) 1-(4-methoxycarbonyl-3-methyl-phenyl)-5-oxo-pyrrolidine-3-carboxylic acid 10 g (60.5 mmol) methyl 4-amino-2-methyl-benzoate and 7.9 g (60.5 mmol) itaconic acid are suspended in 50 ml xylene and refluxed for seven hours. The reaction mixture is cooled to ambient temperature and evaporated to dryness. The residue is suspended in methanol. The undissolved solid is filtered off and dried until the weight remains constant.

Yield: 6.9 g (42%) $R_t$ value: 2.53 min $C_{14}H_{15}NO_5$ (277.27) Mass spectrum: $(M+H)^{30}$ =278

(c) methyl 4-(4-tert.-butoxycarbonylamino no-2-oxo-pyrrolidin- 1-yl)-2-methyl-benzoate 3 g (70%, 7.6 mmol) 1-(4-methoxycarbonyl-3-methyl-phenyl)-5-oxo-pyrrolidine-3-carboxylic acid are suspended in 105 ml tert.-butanol, combined with 1.05 ml (7.6 mmol) triethylamine and then with 1.7 ml (7.6 mmol) DPPA. The mixture is stirred for five hours at reflux temperature, then 2 days at ambient temperature. It is evaporated to dryness and the residue is purified by chromatography on silica gel (eluant: dichloromethane/isopropanol 95:5)

Yield: 2.38 g (75%, 68% corrected yield) $R_t$ value: 3.02 min $C_{18}H_{24}N_2O_5$ (348.39) Mass spectrum: $(M+H)^{30}$ =349

(d) methyl 4-(4-amino-2-oxo-pyrrolidin-1-yl)-2-methyl-benzoate trifluoroacetate 1.9 g (75%, 5.5 mmol) methyl 4-(4-tert.-butoxycarbonylamino-2-oxo-pyrrolidin-1-yl)-2-methyl-benzoate are dissolved in 25 ml dichloromethane and combined with 4.4 ml TFA. The mixture is stirred for 18 hours at ambient temperature, then evaporated to dryness and the residue is purified by chromatography on silica gel (eluant: gradient dichloromethane/isopropanol/ammonia 90:10:0.2-dichloromethane/methanol/ammonia 50:50:0.4).

Yield: quantitative $R_t$ value: 2.0 min $C_{13}H_{16}N_2O_3$ (248.28) Mass spectrum: $(M+H)^+$=249

(e) methyl 4-{4-[(5-bromo-thiophene-2-carbonyl)-amino]-2-oxo-pyrrolidin-1-yl}-2-methyl-benzoate 1.1 g (5.3 mmol) 5-bromo-thiophene-2-carboxylic acid in 10 ml DMF are combined with 4.2 ml (38.2 mmol) NMM and 1.7 g (5.2 mmol) TBTU and then stirred for 10 min under a nitrogen atmosphere at ambient temperature. Then 2.5 g (5.2 mmol) methyl 4-(4-amino-2-oxo-pyrrolidin-1-yl)-2-methyl-benzoate trifluoroacetate dissolved in 10 ml DMF are added and the mixture is stirred for 16 hours at ambient temperature. Then it is combined with sat. sodium hydrogen carbonate solution and water and extracted with ethyl acetate. The aqueous phase is extracted twice with ethyl acetate. The combined organic phases are dried over sodium sulphate and evaporated down completely i. vac. The residue is chromatographed on silica gel (eluant: petroleum ether/ethyl acetate 3:2).

Yield: 1.6 g (70%) $R_t$ value: 3.17 min $C_{18}H_{17}BrN_2O_4S$ (437.31) Mass spectrum: $(M+H)^+$=437/439 (bromine isotope)

(f) 4-f4-[(5-bromo-thiophene-2-carbonyl)-amino]-2-oxo-pyrrolidin-1-yl-2-methyl-benzoic acid 1.98 g (4.54 mmol) methyl 4-{4-[(5-bromo-thiophene-2-carbonyl)-amino]-2-oxo-pyrrolidin-1-yl}-2-methyl-benzoate are suspended in 10 ml of ethanol, combined with 8.1 ml (27 mmol) aqueous 8% lithium hydroxide solution and stirred for three days at ambient temperature. The mixture is evaporated down to a third of the volume and combined with water and ethyl acetate, and 2 N hydrochloric acid is added until a pH of 5 is obtained. The aqueous phase is extracted twice with ethyl acetate. The combined organic phases are dried over sodium sulphate and evaporated to dryness. The residue is purified by chromatography on silica gel (eluant: dichloromethane/isopropanol 9:1-0:100 gradient).

Yield: 160 mg (8%) $R_t$ value: 2.81 min $C_{17}H_{15}BrN_2O_4S$ (423.28) Mass spectrum: $(M+H)^+$=423/425 (bromine isotope)

(g) 5-bromo-thiophene-2-carboxylic acid-{1-[3-methyl-4-(3-oxo-piperazine-1-carbonyl)-phenyl]-5-oxo-pyrrolidin-3-yl}-amide Prepared analogously to Example 1 e from 4-{4-[(5-bromo-thiophene-2-carbonyl)-amino]-2-oxo-pyrrolidin-1-yl}-2-methyl-benzoic acid and piperazin-2-one with TBTU and NMM in DMF and subsequent purification by chromatography (silica gel, eluant: dichloromethane/isopropanol 95:5).

Yield: 84% $R_f$ value: 0.28 (silica gel; dichloromethane/isopropanol 9:1) $C_{21}H_{21}BrN_4O_4S$ (505.39) Mass spectrum: $(M+H)^+$=505/507 (bromine isotope)

The following compounds were prepared analogously:

| No. | Structural formula Name | Mass peak(s) | $R_f$ value or $R_t$ |
|---|---|---|---|
| 2 | 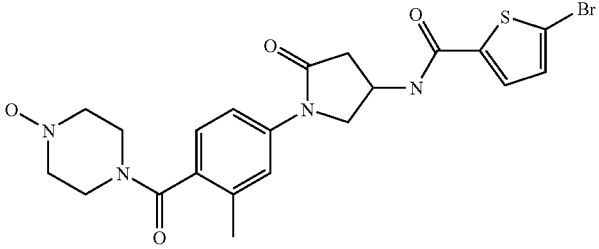<br>5-bromo-thiophene-2-carboxylic acid-{1-[4-(4-hydroxy-piperazine-1-carbonyl)-3-methyl-phenyl]-5-oxo-pyrrolidin-3-yl}-amide | $(M + H)^+ = 508.42$ | 3.20 min |
| 3 | 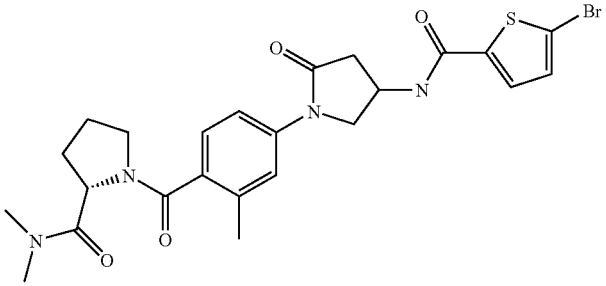<br>(2S)-1-(4-{4-[(5-bromo-thiophene-2-carbonyl)-amino]-2-oxo-pyrrolidin-1-yl}-2-methyl-benzoyl)-pyrrolidine-2-carboxylic acid dimethylamide | $(M + H)^+ = 548.48$ | 3.55 min |
| 4 | 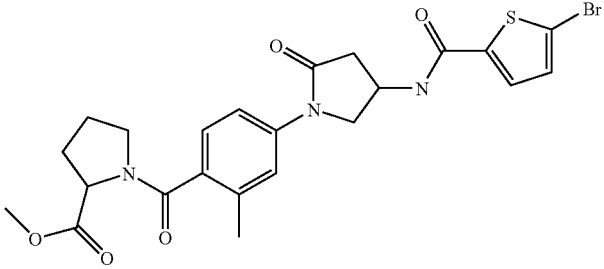<br>methyl 1-(4-{4-[(5-bromo-thiophene-2-carbonyl)-amino]-2-oxo-pyrrolidin-1-yl}-2-methyl-benzoyl)-pyrrolidine-2-carboxylate | $(M + H)^+ = 535.44$ | 3.81 min |
| 5 | 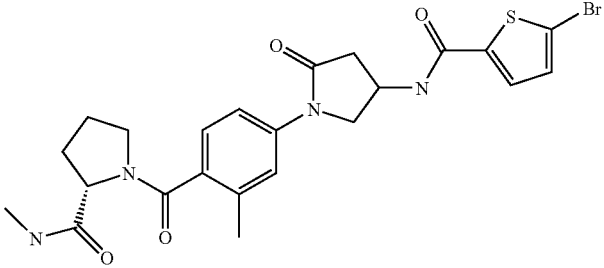<br>(2S)-1-(4-{4-[(5-bromo-thiophene-2-carbonyl)-amino]-2-oxo-pyrrolidin-1-yl}-2-methyl-benzoyl)-pyrrolidine-2-carboxylic acid methylamide | $(M + H)^+ = 534.46$ | 3.44 min |

-continued

| No. | Structural formula Name | Mass peak(s) | $R_f$ value or $R_t$ |
|---|---|---|---|
| 6 | 5-bromo-thiophene-2-carboxylic acid-{1-[3-methyl-4-(3,4,5,6-tetrahydro-2H-[2,3']bipyridinyl-1-carbonyl)-phenyl]-5-oxo-pyrrolidin-3-yl}-amide | $(M + H)^+ = 568.52$ | 3.34 min |
| 7 | 5-bromo-thiophene-2-carboxylic acid-{1-[3-methyl-4-((2S)-2-pyrrolidin-1-ylmethyl-pyrrolidine-1-carbonyl)-phenyl]-5-oxo-pyrrolidin-3-yl}-amide | $(M + H)^+ = 560.54$ | 3.32 min |
| 8 | methyl 1-(4-{4-[(5-bromo-thiophene-2-carbonyl)-amino]-2-oxo-pyrrolidin-1-yl}-2-methyl-benzoyl)-piperidine-2-carboxylate | $(M + H)^+ = 549.47$ | 4.03 min |
| 9 | (2R)-1-(4-{4-[(5-bromo-thiophene-2-carbonyl)-amino]-2-oxo-pyrrolidin-1-yl}-2-methyl-benzoyl)-pyrrolidine-2-carboxylic acid amide | $(M + H)^+ = 520.43$ | 3.39 min |

-continued

| No. | Structural formula Name | Mass peak(s) | $R_f$ value or $R_t$ |
|---|---|---|---|
| 10 | 5-bromo-thiophene-2-carboxylic acid-(1-{4-[3-(butane-1-sulphonylamino)-piperidine-1-carbonyl]-3-methyl-phenyl}-5-oxo-pyrrolidin-3-yl)-amide | $(M + H)^+ = 626.62$ | 3.90 min |
| 11 | 1-(4-{4-[(5-bromo-thiophene-2-carbonyl)-amino]-2-oxo-pyrrolidin-1-yl}-2-methyl-benzoyl)-piperidine-4-carboxylic acid amide | $(M + H)^+ = 534.46$ | 3.35 min |
| 12 | 5-bromo-thiophene-2-carboxylic acid-{1-[3-methyl-4-(3-methyl-piperidine-1-carbonyl)-phenyl]-5-oxo-pyrrolidin-3-yl}-amide | $(M + H)^+ = 505.46$ | 4.13 min |
| 13 | 5-bromo-thiophene-2-carboxylic acid-{1-[3-methyl-4-(4-methyl-piperidine-1-carbonyl)-phenyl]-5-oxo-pyrrolidin-3-yl}-amide | $(M + H)^+ = 505.46$ | 4.14 min |

-continued

| No. | Structural formula Name | Mass peak(s) | $R_f$ value or $R_t$ |
|---|---|---|---|
| 14 | 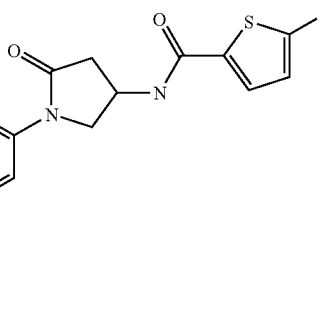<br>5-bromo-thiophene-2-carboxylic acid-(1-{4-[3-(3-butyl-ureido)-piperidine-1-carbonyl]-3-methyl-phenyl}-5-oxo-pyrrolidin-3-yl)-amide | $(M + H)^+ = 605.58$ | 3.81 min |
| 15 | 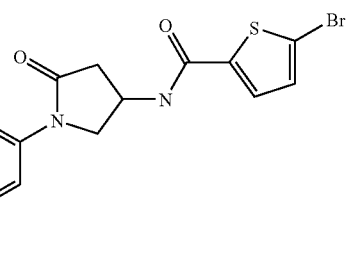<br>5-bromo-thiophene-2-carboxylic acid-{1-[4-(dimethylcarbamoylmethyl-methyl-carbamoyl)-3-methyl-phenyl]-5-oxo-pyrrolidin-3-yl}-amide | $(M + H)^+ = 522.44$ | 3.48 min |
| 16 | 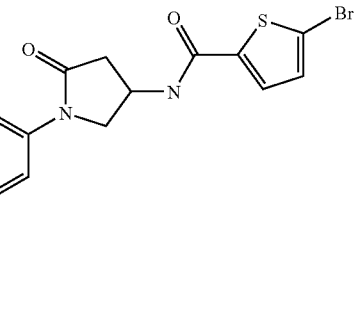<br>5-bromo-thiophene-2-carboxylic acid-(1-{4-[2-(4-dimethylamino-butyl)-piperidine-1-carbonyl]-3-methyl-phenyl}-5-oxo-pyrrolidin-3-yl)-amide | $(M + H)^+ = 590.61$ | 3.42 min |
| 17 | 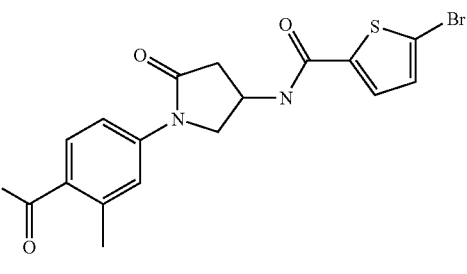<br>methyl (2S,4R)-1-(4-{4-[(5-bromo-thiophene-2-carbonyl)-amino]-2-oxo-pyrrolidin-1-yl}-2-methyl-benzoyl)-4-hydroxy-pyrrolidine-2-carboxylate | $(M + H)^+ = 551.44$ | 3.50 min |

-continued

| No. | Structural formula Name | Mass peak(s) | $R_f$-value or $R_t$ |
|---|---|---|---|
| 18 | 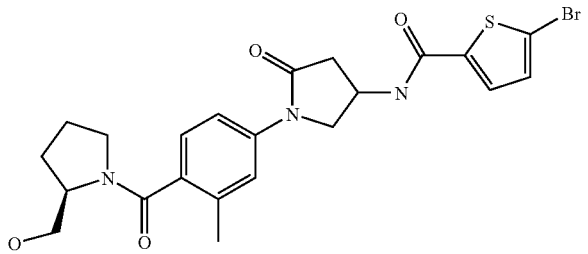<br>5-bromo-thiophene-2-carboxylic acid-{1-[4-(R-2-hydroxymethyl-pyrrolidine-1-carbonyl)-3-methyl-phenyl]-5-oxo-pyrrolidin-3-yl}-amide | $(M + H)^+ = 507.43$ | 3.55 min |
| 19 | 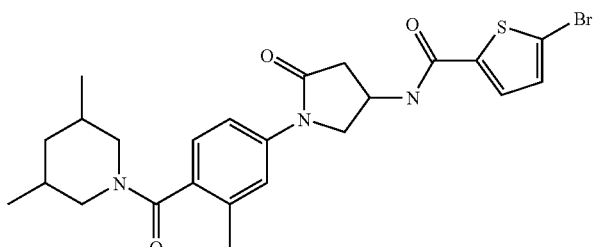<br>5-bromo-thiophene-2-carboxylic acid-{1-[4-(3,5-dimethyl-piperidine-1-carbonyl)-3-methyl-phenyl]-5-oxo-pyrrolidin-3-yl}-amide | $(M + H)^+ = 519.48$ | 4.31 min |
| 20 | 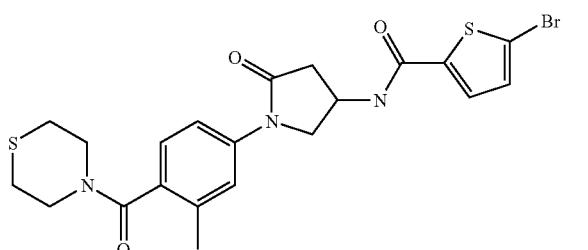<br>5-bromo-thiophene-2-carboxylic acid-{1-[3-methyl-4-(thiomorpholine-4-carbonyl)-phenyl]-5-oxo-pyrrolidin-3-yl}-amide | $(M + H)^+ = 509.47$ | 3.89 min |
| 21 | 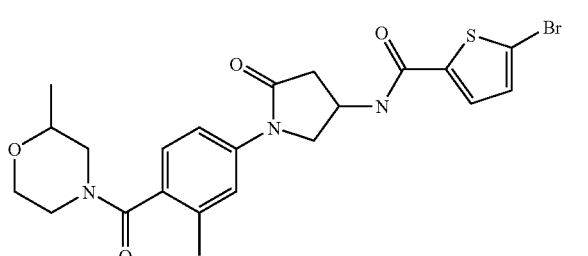<br>5-bromo-thiophene-2-carboxylic acid-{1-[3-methyl-4-(2-methyl-morpholine-4-carbonyl)-phenyl]-5-oxo-pyrrolidin-3-yl}-amide | $(M + H)^+ = 507.43$ | 3.73 min |
| 22 | 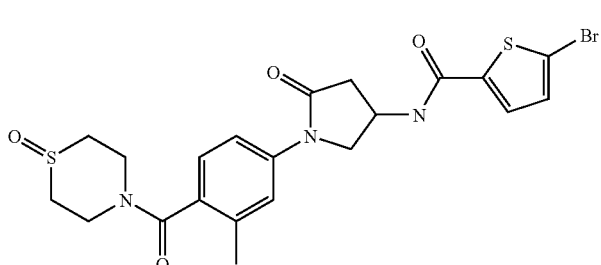<br>5-bromo-thiophene-2-carboxylic acid-{1-[3-methyl-4-(1-oxo-1$\lambda^4$-thiomorpholine-4-carbonyl)-phenyl]-5-oxo-pyrrolidin-3-yl}-amide | $(M + H)^+ = 525.47$ | 3.34 min |

-continued

| No. | Structural formula Name | Mass peak(s) | $R_f$ value or $R_t$ |
|---|---|---|---|
| 23 | 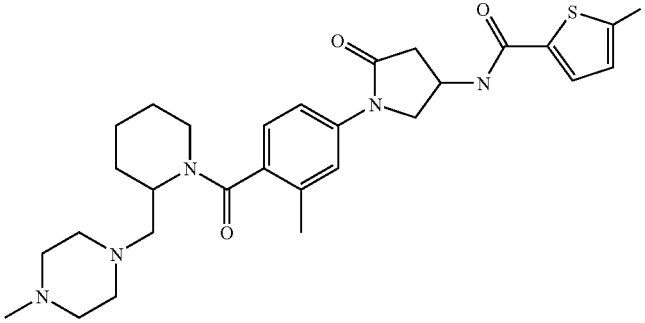<br>5-bromo-thiophene-2-carboxylic acid-(1-{3-methyl-4-[2-(4-methyl-piperazin-1-ylmethyl)-piperidine-1-carbonyl]-phenyl}-5-oxo-pyrrolidin-3-yl)-amide | $(M + H)^+ = 603.60$ | 3.26 min |
| 24 | 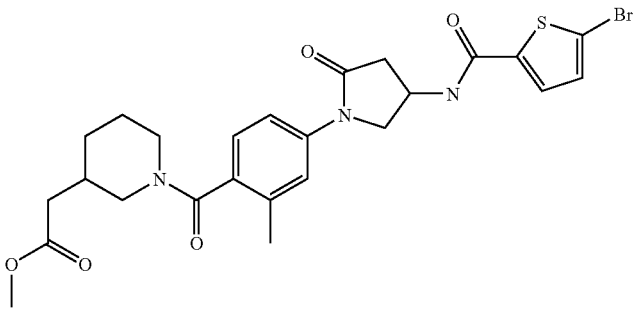<br>methyl 1-(4-{4-[(5-bromo-thiophene-2-carbonyl)-amino]-2-oxo-pyrrolidin-1-yl}-2-methyl-benzoyl)-piperidin-3-yl]acetate | $(M + H)^+ = 563.49$ | 3.91 min |
| 25 | 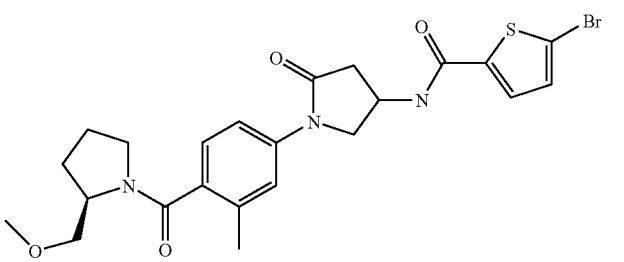<br>5-bromo-thiophene-2-carboxylic acid-{1-[4-((2R)-2-methoxymethyl-pyrrolidine-1-carbonyl)-3-methyl-phenyl]-5-oxo-pyrrolidin-3-yl}-amide | $(M + H)^+ = 521.46$ | 3.85 min |
| 26 | 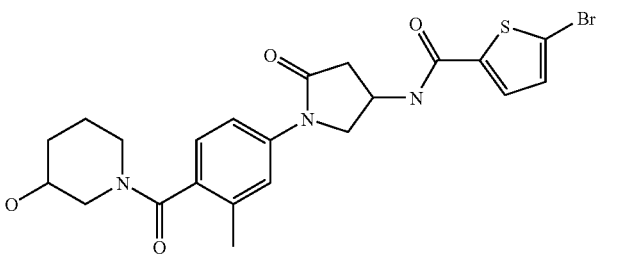<br>5-bromo-thiophene-2-carboxylic acid-{1-[4-(3-hydroxy-piperidine-1-carbonyl)-3-methyl-phenyl]-5-oxo-pyrrolidin-3-yl}-amide | $(M + H)^+ = 507.43$ | 3.50 min |

-continued

| No. | Structural formula / Name | Mass peak(s) | $R_f$ value or $R_t$ |
|---|---|---|---|
| 27 | 5-bromo-thiophene-2-carboxylic acid-{1-[4-((2S)-2-hydroxymethyl-pyrrolidine-1-carbonyl)-3-methyl-phenyl]-5-oxo-pyrrolidin-3-yl}-amide | $(M + H)^+ = 507.43$ | 3.55 min |
| 28 | 5-bromo-thiophene-2-carboxylic acid-{1-[4-((2S)-2-methoxymethyl-pyrrolidine-1-carbonyl)-3-methyl-phenyl]-5-oxo-pyrrolidin-3-yl}-amide | $(M + H)^+ = 521.46$ | 3.86 min |
| 29 | 5-bromo-thiophene-2-carboxylic acid-{1-[4-(4-methoxy-piperidine-1-carbonyl)-3-methyl-phenyl]-5-oxo-pyrrolidin-3-yl}-amide | $(M + H)^+ = 521.46$ | 3.74 min |
| 30 | 5-bromo-thiophene-2-carboxylic acid-(1-{4-[2-(2-diethylamino-ethyl)-piperidine-1-carbonyl]-3-methyl-phenyl}-5-oxo-pyrrolidin-3-yl)-amide | $(M + H)^+ = 590.61$ | 3.40 min |

-continued

| No. | Structural formula Name | Mass peak(s) | $R_f$ value or $R_t$ |
|---|---|---|---|
| 31 | 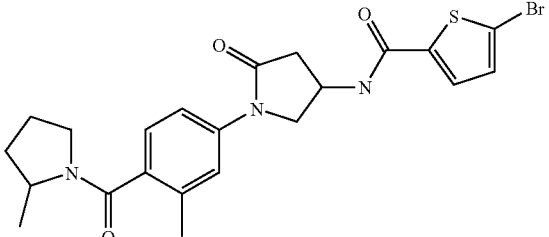<br>5-bromo-thiophene-2-carboxylic acid-{1-[3-methyl-4-(2-methyl-pyrrolidine-1-carbonyl)-phenyl]-5-oxo-pyrrolidin-3-yl}-amide | $(M + H)^+ = 491.43$ | 3.90 min |
| 32 | 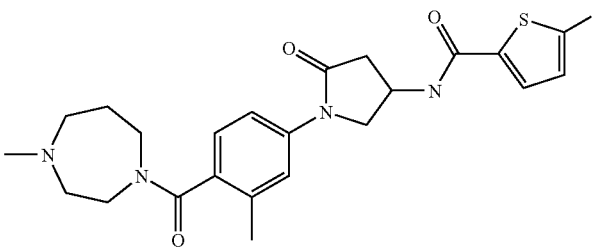<br>5-bromo-thiophene-2-carboxylic acid-{1-[3-methyl-4-(4-methyl-[1,4]diazepan-1-carbonyl)-phenyl]-5-oxo-pyrrolidin-3-yl}-amide | $(M + H)^+ = 520.47$ | 3.14 min |
| 33 | 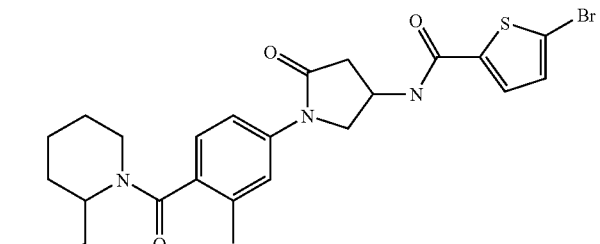<br>5-bromo-thiophene-2-carboxylic acid-(1-{4-[2-(3-hydroxy-propyl)-piperidine-1-carbonyl]-3-methyl-phenyl}-5-oxo-pyrrolidin-3-yl)-amide | $(M + H)^+ = 549.51$ | 3.74 min |
| 34 | 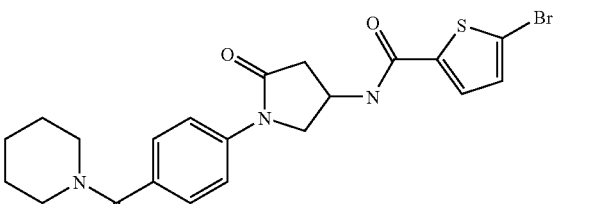<br>5-bromo-thiophene-2-carboxylic acid-{1-[3-methyl-4-(piperidine-1-carbonyl)-phenyl]-5-oxo-pyrrolidin-3-yl}-amide | $(M + H)^+ = 491.43$ | 3.95 min |
| 35 | 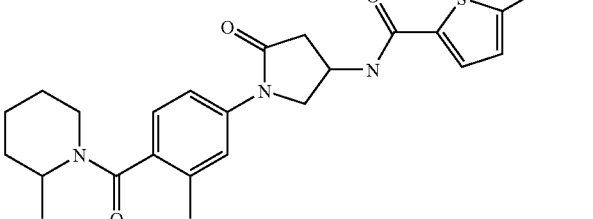<br>5-bromo-thiophene-2-carboxylic acid-{1-[3-methyl-4-(2-methyl-piperidine-1-carbonyl)-phenyl]-5-oxo-pyrrolidin-3-yl}-amide | $(M + H)^+ = 505.46$ | 4.07 min |

-continued

| No. | Structural formula Name | Mass peak(s) | $R_f$ value or $R_t$ |
|---|---|---|---|
| 36 | 1-(4-{4-[(5-bromo-thiophene-2-carbonyl)-amino]-2-oxo-pyrrolidin-1-yl}-2-methyl-benzoyl)-piperidine-3-carboxylic acid amide | $(M + H)^+ = 534.46$ | 3.42 min |
| 37 | 5-bromo-thiophene-2-carboxylic acid-{1-[4-(4-hydroxy-piperidine-1-carbonyl)-3-methyl-phenyl]-5-oxo-pyrrolidin-3-yl}-amide | $(M + H)^+ = 507.43$ | 3.42 min |
| 38 | 5-bromo-thiophene-2-carboxylic acid-{1-[4-(4-acetyl-piperazine-1-carbonyl)-3-methyl-phenyl]-5-oxo-pyrrolidin-3-yl}-amide | $(M + H)^+ = 534.46$ | 3.44 min |
| 39 | 5-bromo-thiophene-2-carboxylic acid-{1-[3-methyl-4-((2R)-2-phenylaminomethyl-pyrrolidine-1-carbonyl)-phenyl]-5-oxo-pyrrolidin-3-yl}-amide | $(M + H)^+ = 582.54$ | 3.79 min |

-continued

| No. | Structural formula Name | Mass peak(s) | $R_f$ value or $R_t$ |
|---|---|---|---|
| 40 | 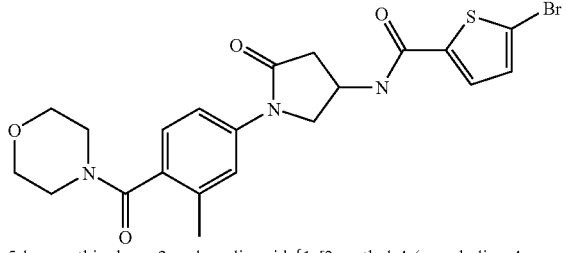 5-bromo-thiophene-2-carboxylic acid-{1-[3-methyl-4-(morpholine-4-carbonyl)-phenyl]-5-oxo-pyrrolidin-3-yl}-amide | $(M + H)^+ = 493.40$ | 3.59 min |
| 41 | 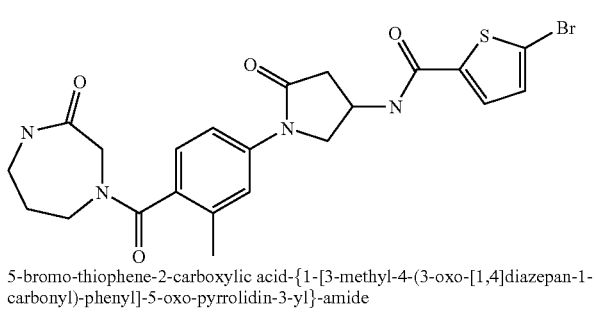 5-bromo-thiophene-2-carboxylic acid-{1-[3-methyl-4-(3-oxo-[1,4]diazepan-1-carbonyl)-phenyl]-5-oxo-pyrrolidin-3-yl}-amide | $(M + H)^+ = 520.43$ | 3.35 min |
| 42 | 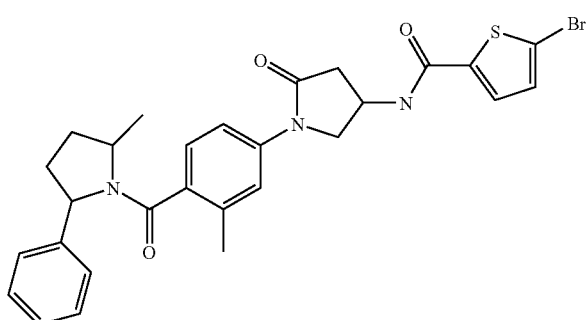 5-bromo-thiophene-2-carboxylic acid-{1-[3-methyl-4-(2-methyl-5-phenyl-pyrrolidine-1-carbonyl)-phenyl]-5-oxo-pyrrolidin-3-yl}-amide | $(M + H)^+ = 567.53$ | 4.38 min |
| 43 | 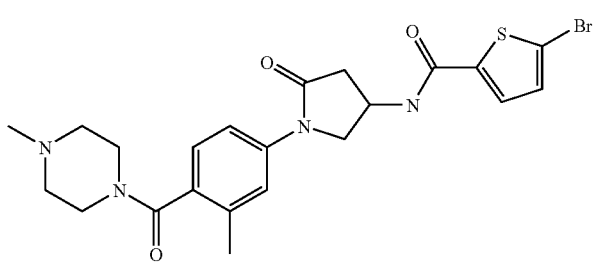 5-bromo-thiophene-2-carboxylic acid-{1-[3-methyl-4-(4-methyl-piperazine-1-carbonyl)-phenyl]-5-oxo-pyrrolidin-3-yl}-amide | $(M + H)^+ = 506.45$ | 3.14 min |
| 44 | 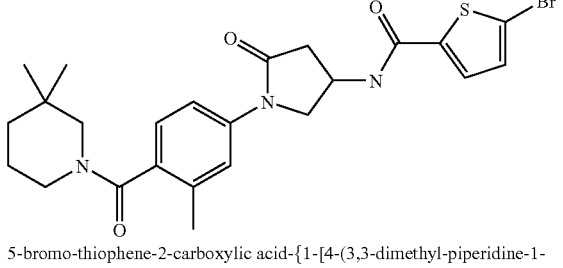 5-bromo-thiophene-2-carboxylic acid-{1-[4-(3,3-dimethyl-piperidine-1-carbonyl)-3-methyl-phenyl]-5-oxo-pyrrolidin-3-yl}-amide | $(M + H)^+ = 519.48$ | 4.23 min |

-continued

| No. | Structural formula Name | Mass peak(s) | R<sub>f</sub> value or R<sub>t</sub> |
|---|---|---|---|
| 45 | 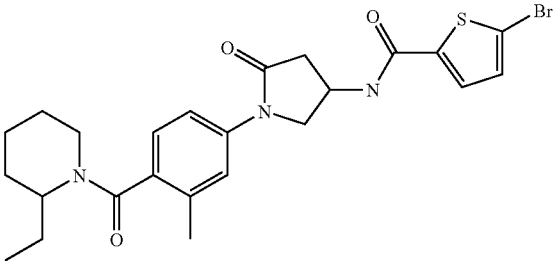<br>5-bromo-thiophene-2-carboxylic acid-{1-[4-(2-ethyl-piperidine-1-carbonyl)-3-methyl-phenyl]-5-oxo-pyrrolidin-3-yl}-amide | $(M + H)^+ = 519.48$ | 4.22 min |
| 46 | 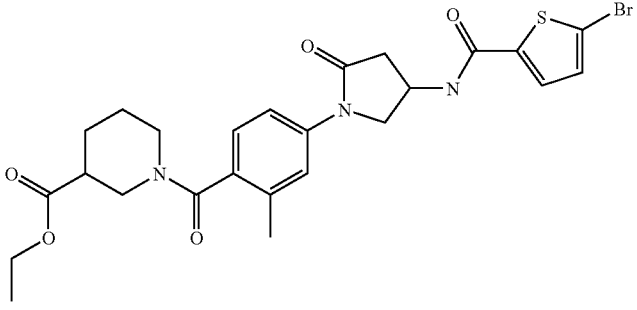<br>ethyl 1-(4-{4-[(5-bromo-thiophene-2-carbonyl)-amino]-2-oxo-pyrrolidin-1-yl}-2-methyl-benzoyl)-piperidine-3-carboxylate | $(M + H)^+ = 563.49$ | 4.03 min |
| 47 | 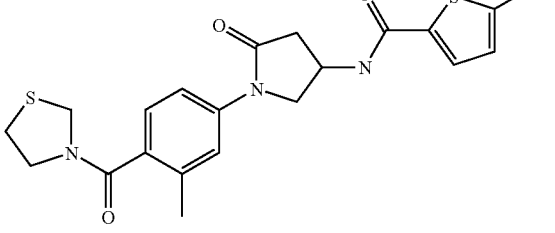<br>5-bromo-thiophene-2-carboxylic acid-{1-[3-methyl-4-(thiazolidine-3-carbonyl)-phenyl]-5-oxo-pyrrolidin-3-yl}-amide | $(M + H)^+ = 495.44$ | 3.85 min |
| 48 | 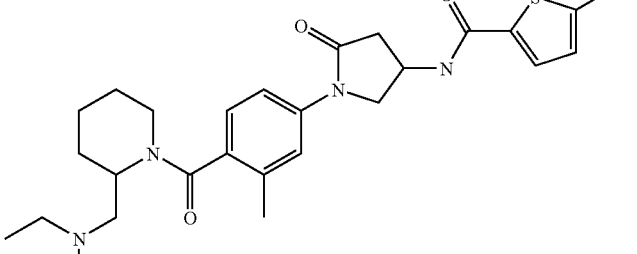<br>5-bromo-thiophene-2-carboxylic acid-[1-(4-{2-[(ethyl-methyl-amino)-methyl]-piperidine-1-carbonyl}-3-methyl-phenyl)-5-oxo-pyrrolidin-3-yl]-amide | $(M + H)^+ = 562.55$ | 3.34 min |

| No. | Structural formula Name | Mass peak(s) | $R_f$ value or $R_t$ |
|---|---|---|---|
| 49 | 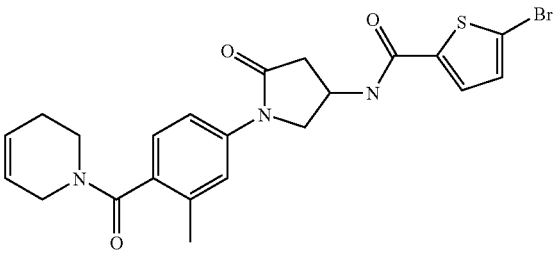<br>5-bromo-thiophene-2-carboxylic acid-{1-[4-(3,6-dihydro-2H-pyridine-1-carbonyl)-3-methyl-phenyl]-5-oxo-pyrrolidin-3-yl}-amide | $(M + H)^+ = 489.41$ | 3.91 min |
| 50 | 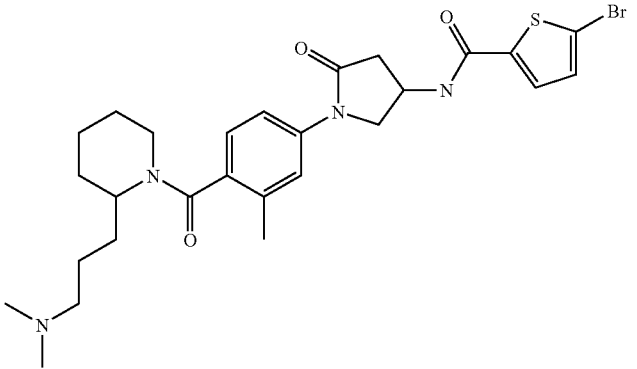<br>5-bromo-thiophene-2-carboxylic acid-(1-{4-[2-(3-dimethylamino-propyl)-piperidine-1-carbonyl]-3-methyl-phenyl}-5-oxo-pyrrolidin-3-yl)-amide | $(M + H)^+ = 576.58$ | 3.36 min |
| 51 | 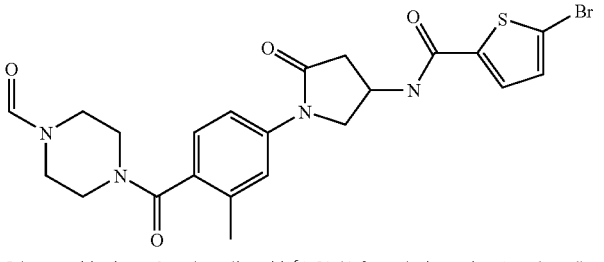<br>5-bromo-thiophene-2-carboxylic acid-{1-[4-(4-formyl-piperazine-1-carbonyl)-3-methyl-phenyl]-5-oxo-pyrrolidin-3-yl}-amide | $(M + H)^+ = 520.43$ | 3.43 min |
| 52 | 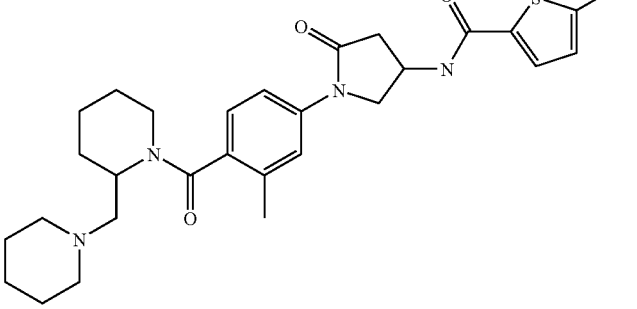<br>5-bromo-thiophene-2-carboxylic acid-{1-[3-methyl-4-(2-piperidin-1-ylmethyl-piperidine-1-carbonyl)-phenyl]-5-oxo-pyrrolidin-3-yl}-amide | $(M + H)^+ = 588.59$ | 3.39 min |

-continued

| No. | Structural formula Name | Mass peak(s) | R_f value or R_t |
|---|---|---|---|
| 53 | 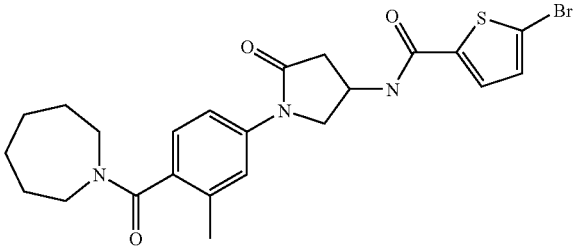  5-bromo-thiophene-2-carboxylic acid-{1-[4-(azepan-1-carbonyl)-3-methyl-phenyl]-5-oxo-pyrrolidin-3-yl}-amide | (M + H)⁺ = 505.46 | 4.06 min |
| 54 | 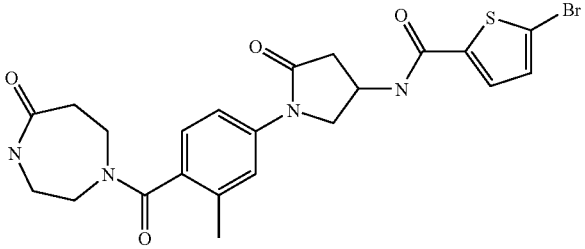  5-bromo-thiophene-2-carboxylic acid-{1-[3-methyl-4-(5-oxo-[1,4]diazepan-1-carbonyl)-phenyl]-5-oxo-pyrrolidin-3-yl}-amide | (M + H)⁺ = 520.43 | 3.34 min |
| 55 | 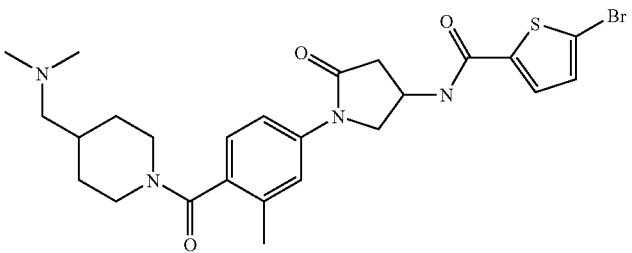  5-bromo-thiophene-2-carboxylic acid-{1-[4-(4-dimethylamino-piperidine-1-carbonyl)-3-methyl-phenyl]-5-oxo-pyrrolidin-3-yl}-amide | (M + H)⁺ = 548.53 | 3.16 min |
| 56 | 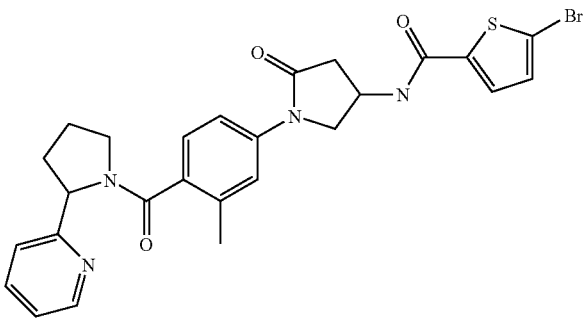  5-bromo-thiophene-2-carboxylic acid-{1-[3-methyl-4-(2-pyridin-2-yl-pyrrolidine-1-carbonyl)-phenyl]-5-oxo-pyrrolidin-3-yl}-amide | (M + H)⁺ = 554.49 | 3.30 min |

| No. | Structural formula Name | Mass peak(s) | $R_f$ value or $R_t$ |
|---|---|---|---|
| 57 | 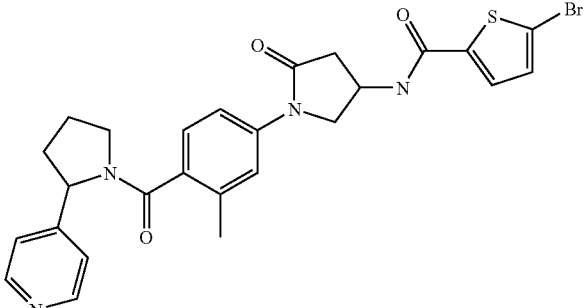 5-bromo-thiophene-2-carboxylic acid-{1-[3-methyl-4-(2-pyridin-4-yl-pyrrolidine-1-carbonyl)-phenyl]-5-oxo-pyrrolidin-3-yl}-amide | $(M + H)^+ = 554.49$ | 3.24 min |
| 58 | 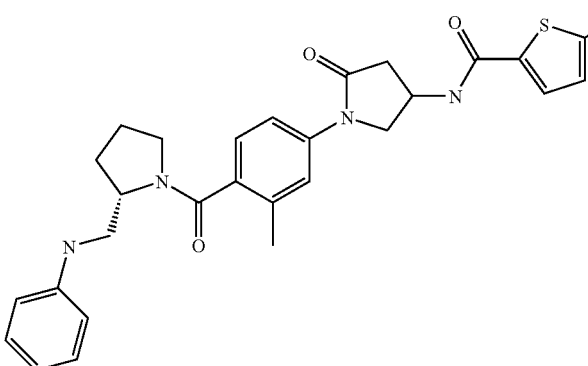 5-bromo-thiophene-2-carboxylic acid-{1-[3-methyl-4-((2S)-2-phenylaminomethyl-pyrrolidine-1-carbonyl)-phenyl]-5-oxo-pyrrolidin-3-yl}-amide | $(M + H)^+ = 582.54$ | 3.79 min |
| 59 | 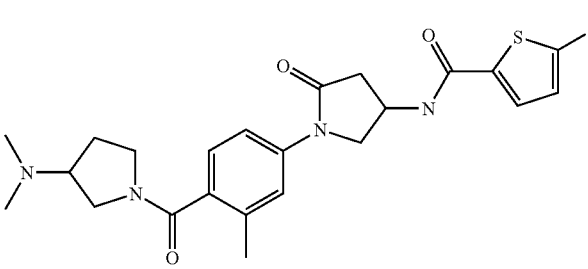 5-bromo-thiophene-2-carboxylic acid-{1-[4-(3-dimethylamino-pyrrolidine-1-carbonyl)-3-methyl-phenyl]-5-oxo-pyrrolidin-3-yl}-amide | $(M + H)^+ = 520.47$ | 3.12 min |
| 60 | 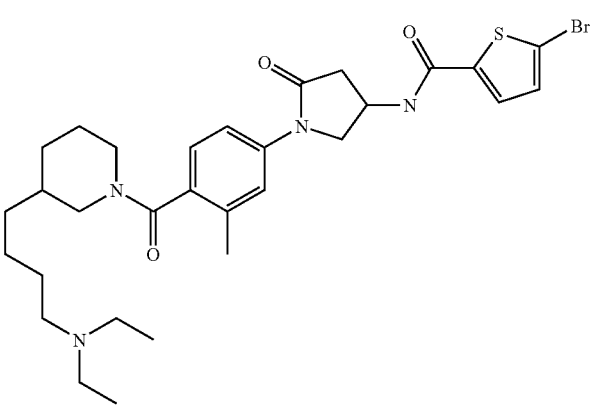 5-bromo-thiophene-2-carboxylic acid-(1-{4-[3-(4-diethylamino-butyl)-piperidine-1-carbonyl]-3-methyl-phenyl}-5-oxo-pyrrolidin-3-yl)-amide | $(M + H)^+ = 618.66$ | 3.47 min |

-continued

| No. | Structural formula Name | Mass peak(s) | $R_f$ value or $R_t$ |
|---|---|---|---|
| 61 | 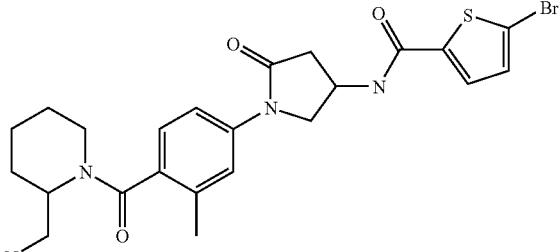<br>5-bromo-thiophene-2-carboxylic acid-{1-[4-(2-aminomethyl-piperidine-1-carbonyl)-3-methyl-phenyl]-5-oxo-pyrrolidin-3-yl}-amide | $(M + H)^+ = 520.47$ | 3.27 min |
| 62 | 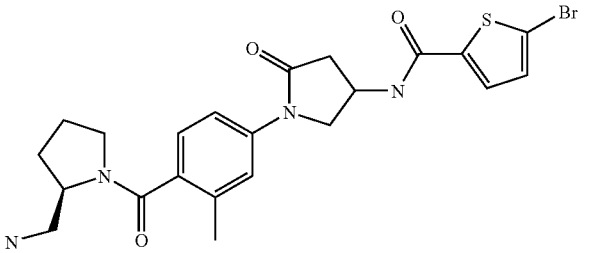<br>5-bromo-thiophene-2-carboxylic acid-{1-[4-((2R)-2-aminomethyl-pyrrolidine-1-carbonyl)-3-methyl-phenyl]-5-oxo-pyrrolidin-3-yl}-amide | $(M + H)^+ = 506.45$ | 3.24 min |
| 63 | 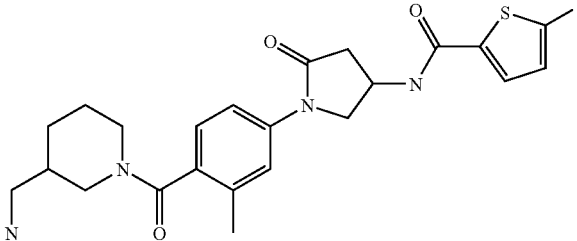<br>5-bromo-thiophene-2-carboxylic acid-{1-[4-(3-aminomethyl-piperidine-1-carbonyl)-3-methyl-phenyl]-5-oxo-pyrrolidin-3-yl}-amide | $(M + H)^+ = 520.47$ | 3.20 min |
| 64 | 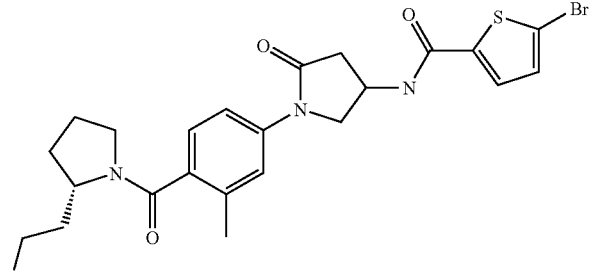<br>5-bromo-thiophene-2-carboxylic acid-(1-{4-[(2S)-2-(2-amino-ethyl)-pyrrolidine-1-carbonyl]-3-methyl-phenyl}-5-oxo-pyrrolidin-3-yl)-amide | $(M + H)^+ = 520.47$ | 3.27 min |
| 65 | 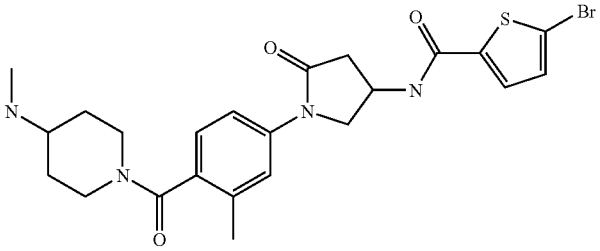<br>5-bromo-thiophene-2-carboxylic acid-{1-[3-methyl-4-(4-methylamino-piperidine-1-carbonyl)-phenyl]-5-oxo-pyrrolidin-3-yl}-amide | $(M + H)^+ = 520.47$ | 3.15 min |

| No. | Structural formula Name | Mass peak(s) | $R_f$ value or $R_t$ |
|---|---|---|---|
| 66 | 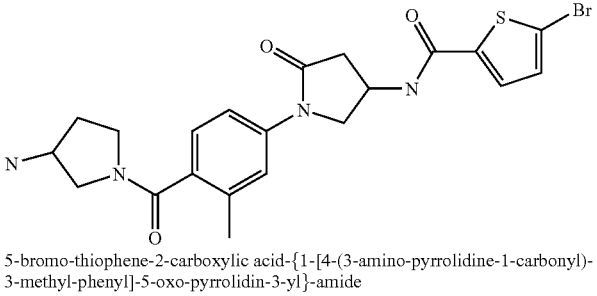<br>5-bromo-thiophene-2-carboxylic acid-{1-[4-(3-amino-pyrrolidine-1-carbonyl)-3-methyl-phenyl]-5-oxo-pyrrolidin-3-yl}-amide | $(M + H)^+ = 492.42$ | 3.11 min |
| 67 | 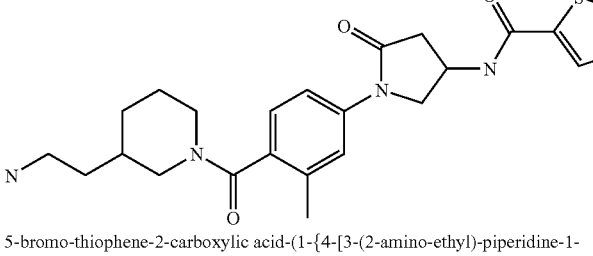<br>5-bromo-thiophene-2-carboxylic acid-(1-{4-[3-(2-amino-ethyl)-piperidine-1-carbonyl]-3-methyl-phenyl}-5-oxo-pyrrolidin-3-yl)-amide | $(M + H)^+ = 534.50$ | 3.24 min |
| 68 | 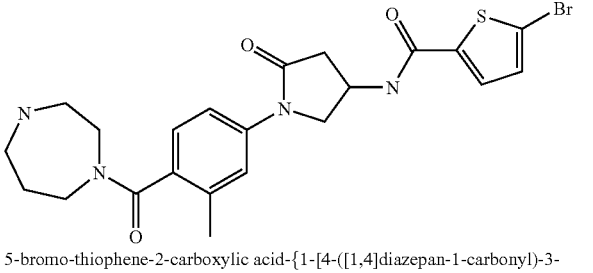<br>5-bromo-thiophene-2-carboxylic acid-{1-[4-([1,4]diazepan-1-carbonyl)-3-methyl-phenyl]-5-oxo-pyrrolidin-3-yl}-amide | $(M + H)^+ = 506.45$ | 3.15 min |
| 69 | 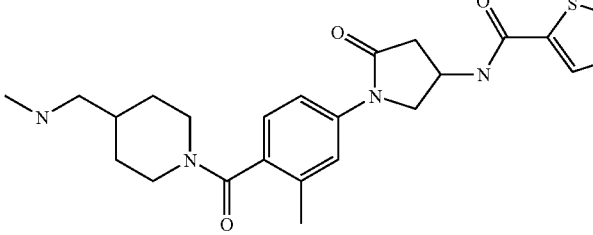<br>5-bromo-thiophene-2-carboxylic acid-{1-[3-methyl-4-(4-methylaminomethyl-piperidine-1-carbonyl)-phenyl]-5-oxo-pyrrolidin-3-yl}-amide | $(M + H)^+ = 534.50$ | 3.16 min |
| 70 | 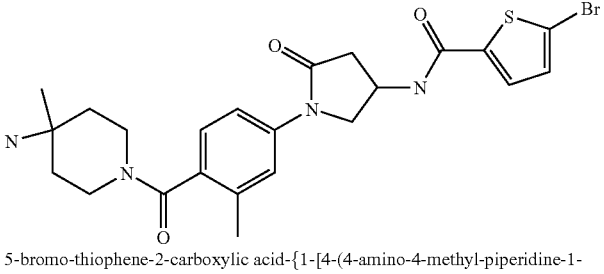<br>5-bromo-thiophene-2-carboxylic acid-{1-[4-(4-amino-4-methyl-piperidine-1-carbonyl)-3-methyl-phenyl]-5-oxo-pyrrolidin-3-yl}-amide | $(M + H)^+ = 520.47$ | 3.15 min |

-continued

| No. | Structural formula Name | Mass peak(s) | $R_f$ value or $R_t$ |
|---|---|---|---|
| 71 | 5-bromo-thiophene-2-carboxylic acid-(1-{4-[2-(2-amino-ethyl)-piperidine-1-carbonyl]-3-methyl-phenyl}-5-oxo-pyrrolidin-3-yl)-amide | $(M + H)^+ = 534.50$ | 3.32 min |
| 72 | 5-bromo-thiophene-2-carboxylic acid-{1-[4-(4-aminomethyl-piperidine-1-carbonyl)-3-methyl-phenyl]-5-oxo-pyrrolidin-3-yl}-amide | $(M + H)^+ = 520.47$ | 3.15 min |
| 73 | 5-bromo-thiophene-2-carboxylic acid-(1-{4-[4-(3-ethylamino-propyl)-piperidine-1-carbonyl]-3-methyl-phenyl}-5-oxo-pyrrolidin-3-yl)-amide | $(M + H)^+ = 576.58$ | 4.37 min |
| 74 | 5-bromo-thiophene-2-carboxylic acid-{1-[4-(dimethylcarbamoylmethyl-carbamoyl)-3-methyl-phenyl]-5-oxo-pyrrolidin-3-yl}-amide | $(M + H)^+ = 508.42$ | 3.47 min |
| 75 | 5-bromo-thiophene-2-carboxylic acid-{1-[4-(1-dimethylcarbamoyl-2-methyl-propylcarbamoyl)-3-methyl-phenyl]-5-oxo-pyrrolidin-3-yl}-amide | $(M + H)^+ = 522.44$ | 3.55 min |

-continued

| No. | Structural formula Name | Mass peak(s) | $R_f$ value or $R_t$ |
|---|---|---|---|
| 76 | 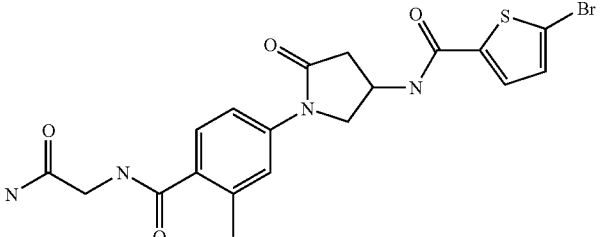 5-bromo-thiophene-2-carboxylic acid-{1-[4-(carbamoylmethyl-carbamoyl)-3-methyl-phenyl]-5-oxo-pyrrolidin-3-yl}-amide | $(M + H)^+ = 480.36$ | 3.32 min |
| 77 | 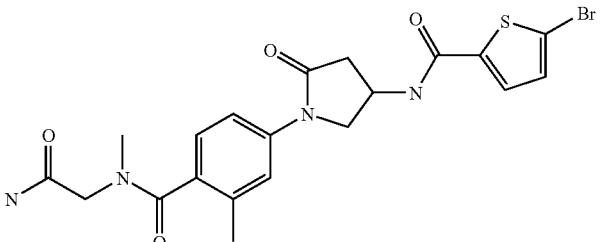 5-bromo-thiophene-2-carboxylic acid-{1-[4-(carbamoylmethyl-methyl-carbamoyl)-3-methyl-phenyl]-5-oxo-pyrrolidin-3-yl}-amide | $(M + H)^+ = 494.39$ | 3.34 min |
| 78 | 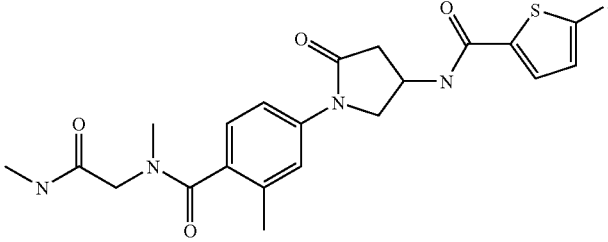 5-bromo-thiophene-2-carboxylic acid-{1-[3-methyl-4-(methyl-methylcarbamoylmethyl-carbamoyl)-phenyl]-5-oxo-pyrrolidin-3-yl}-amide | $(M + H)^+ = 508.42$ | 3.40 min |
| 79 | 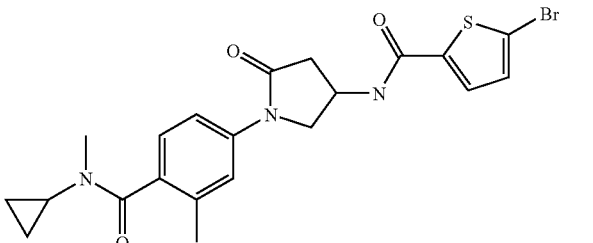 5-bromo-thiophene-2-carboxylic acid-{1-[4-(cyclopropyl-methyl-carbamoyl)-3-methyl-phenyl]-5-oxo-pyrrolidin-3-yl}-amide | $(M + H)^+ = 477.40$ | 3.82 min |
| 80 | 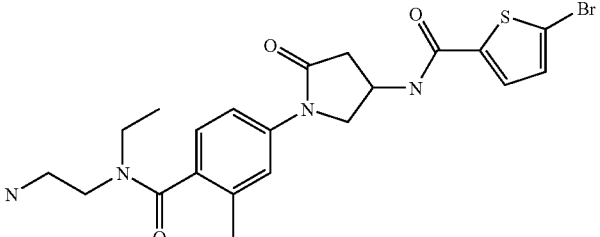 5-bromo-thiophene-2-carboxylic acid-(1-{4-[(2-amino-ethyl)-ethyl-carbamoyl]-3-methyl-phenyl}-5-oxo-pyrrolidin-3-yl)-amide | $(M + H)^+ = 494.43$ | 3.2 min |

| No. | Structural formula Name | Mass peak(s) | $R_f$ value or $R_t$ |
|---|---|---|---|
| 81 | 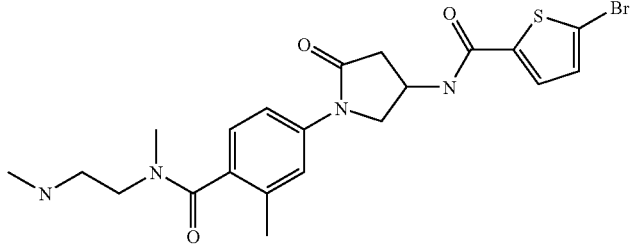<br>5-bromo-thiophene-2-carboxylic acid-(1-{3-methyl-4-[methyl-(2-methylamino-ethyl)-carbamoyl]-phenyl}-5-oxo-pyrrolidin-3-yl)-amide | $(M + H)^+ = 494.43$ | 3.18 min |
| 82 | 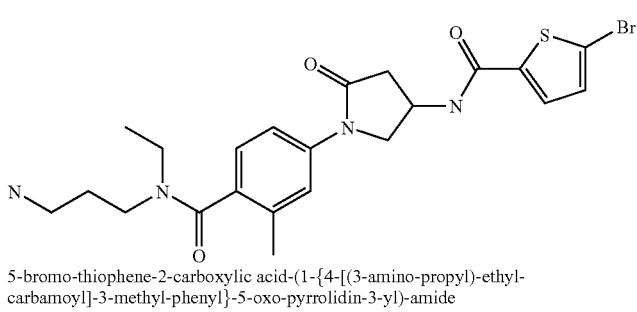<br>5-bromo-thiophene-2-carboxylic acid-(1-{4-[(3-amino-propyl)-ethyl-carbamoyl]-3-methyl-phenyl}-5-oxo-pyrrolidin-3-yl)-amide | $(M + H)^+ = 508.46$ | 3.24 min |
| 83 | 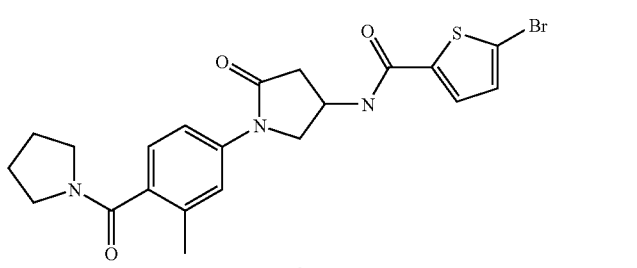<br>5-bromo-thiophene-2-carboxylic acid-{1-[3-methyl-4-(pyrrolidine-1-carbonyl)-phenyl]-5-oxo-pyrrolidin-3-yl}-amide | $(M + H)^+ = 476/478$ (bromine isotope) | 0.17 (silica gel, dichloromethane/ isopropanol 95:5) |

EXAMPLE 84

5-bromo-thiophene-2-carboxylic acid-[1-(2'-dimethylaminomethyl-biphenyl-4-yl)-5-oxo-pyrrolidin-3-yl]-amide

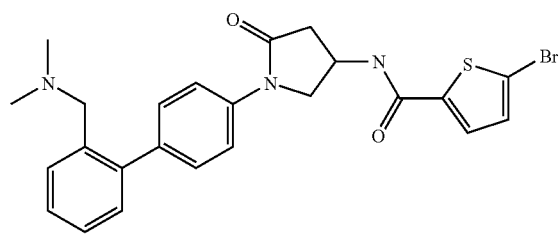

(a) 1-(4-bromo-phenyl)-5-oxo-pyrrolidine-3-carboxylic acid

Prepared analogously to Example 1b from 4-bromoaniline and itaconic acid.

Yield: 98% $R_t$ value: 4.07 min $C_{11}H_{10}BrNO_3$ (284.11)
Mass spectrum: $(M+H)^+=284/286$ (bromine isotope)

(b) tert-butyl[1-(4-bromo-phenyl)-5-oxo-pyrrolidin-3-yl]-carbamate

Prepared analogously to Example 1c from 1-(4-bromo-phenyl)-5-oxo-pyrrolidine-3-carboxylic acid, tert.-butanol and DPPA.

Yield: 60% $R_t$ value: 4.90 min $C_{15}H_{19}BrN_2O_3$ (355.23)
Mass spectrum: $(M+H)^+=355/357$ (bromine isotope)

(c) tert-butyl[1(3'-dimethylaminomethyl-biphenyl-4-yl)-5-oxo-pyrrolidin-3-yl]-carbamate 525 mg (1.48 mmol) tert-butyl[1-(4-bromo-phenyl)-5-oxo-pyrrolidin-3-yl]-carbamate are dissolved in 30 ml of toluene and 5 ml of water and combined with 318 mg (1.77 mmol) 2-(N,N-dimethylaminomethyl)phenylboronic acid, 48 mg (0.15 mmol) tetrabutylammonium bromide and 314 mg (2.96 mmol) potassium carbonate, and lastly 173 mg (0.15 mmol) tetrakis(triphenylphosphine)palladium(0) are added. The reaction solution is refluxed for 90 minutes at 400 Watt in the microwave. Then another 330 mg (1.84 mmol) 2-(N,N-dimethylaminomethyl)phenylboronic acid are added and the mixture is heated for one hour at 400 Watt in the microwave. The reaction solution is evaporated to dryness i. vac. The residue is purified by reversed phase chromatography.

Yield: 130 mg (21%) R$_f$ value: 4.17 min C$_{24}$H$_{31}$N$_3$O$_3$ (409.52) Mass spectrum: (M+H)$^+$=410

(d) 4-amino-1-(2'-dimethylaminomethyl-biphenyl-4-yl)-pyrrolidin-2-one-dihydrochloride 130 mg (0.32 mmol) tert-butyl[1,(3'-dimethylaminomethyl-biphenyl-4-yl)-5-oxo-pyrrolidin-3-yl]-carbamate are dissolved in 5 ml hydrogen chloride in dioxane (4 M), stirred for two hours at ambient temperature and then evaporated to dryness in the rotary evaporator.

Yield: quantitative R$_t$ value: 3.08 min C$_{19}$H$_{23}$N$_3$O×2 HCl (382.33) C$_{19}$H$_{23}$N$_3$O (309.41) Mass spectrum: (M+H)$^+$=310

(e) 5-bromo-thiophene-2-carboxylic acid[1-(2'-dimethylaminomethyl-biphenyl-4-yl)-5-oxo-pyrrolidin-3-yl]amide Prepared from 4-amino-1-(2'-dimethylaminomethyl-biphenyl-4-yl)-pyrrolidin-2-one-dihydrochloride, TBTU, NMM and 5-bromo-thiophene-2-carboxylic acid analogously to Example 1g. The purification is carried out by reversed phase chromatography.

Yield: 34% R$_t$ value: 4.27 min C$_{24}$H$_{24}$BrN$_3$O$_4$S×C$_2$HF$_3$O$_2$ (612.46) C$_{24}$H$_{24}$BrN$_3$O$_4$S (498.45) Mass spectrum: (M+H)=498/500 (bromine isotope)

The following compounds were prepared analogously:

| No. | Structural formula Name | Yield | Mass peak(s) | R$_f$ value or R$_t$ |
|---|---|---|---|---|
| 85 | 5-chloro-thiophene-2-carboxylic acid[1-(2'-dimethylaminomethyl-biphenyl-4-yl)-5-oxo-pyrrolidin-3-yl]amide | Σ: 7.3% | (M + H)$^+$ = 454/456 (chlorine isotope) | 4.24 min |
| 86 | 5-bromo-thiophene-2-carboxylic acid-[1-(2'-methanesulphonyl-biphenyl-4-yl)-5-oxo-pyrrolidin-3-yl]-amide | Σ: 9.5% | (M + H)$^+$ = 519/521 (bromine isotope) | 4.81 min |
| 87 | 5-chloro-thiophene-2-carboxylic acid-[1-(2'-methanesulphonyl-biphenyl-4-yl)-5-oxo-pyrrolidin-3-yl]-amide | Σ: 9.7% | (M + H)$^+$ = 475/477 (chlorine isotope) | 4.73 min |
| 88 | 5-bromo-furan-2-carboxylic acid-[1-(2'-methanesulphonyl-biphenyl-4-yl)-5-oxo-pyrrolidin-3-yl]-amide | Σ: 10.1% | (M + H)$^+$ = 503/505 (bromine isotope) | 4.43 min |

-continued

| No. | Structural formula Name | Yield | Mass peak(s) | $R_f$ value or $R_t$ |
|---|---|---|---|---|
| 89 | 4-bromo-N-[1-(2'-methanesulphonyl-biphenyl-4-yl)-5-oxo-pyrrolidin-3-yl]-benzamide | Σ: 7.5% | $(M + H)^+$ = 513/515 (bromine isotope) | 4.75 min |
| 90 | 4-chloro-N-[1-(2'-methanesulphonyl-biphenyl-4-yl)-5-oxo-pyrrolidin-3-yl]-benzamide | Σ: 4.9% | $(M + H)^+$ = 569/571 (chlorine isotope) | 4.65 min |
| 91 | 4-bromo-N-[1-(2'-dimethylaminomethyl-biphenyl-4-yl)-5-oxo-pyrrolidin-3-yl]-benzamide | Σ: 4.6% | $(M + H)^+$ = 492/494 (bromine isotope) | 4.25 min |
| 92 | 4-chloro-N-[1-(2'-dimethylaminomethyl-biphenyl-4-yl)-5-oxo-pyrrolidin-3-yl]-benzamide | Σ: 5.7% | $(M + H)^+$ = 448/450 (chlorine isotope) | 4.17 min |

EXAMPLE 93

(R)-5-bromo-thiophene-2-carboxylic acid-{1-[3-methyl-4-(pyrrolidine-1-sulphonyl)-phenyl]-5-oxo-pyrrolidin-3-yl}-amide

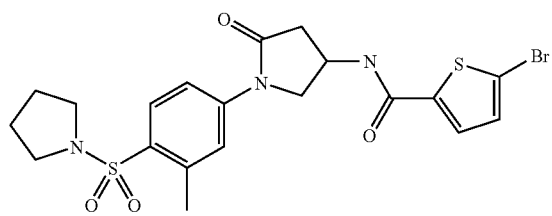

(a) 4-acetylamino-2-methyl-benzenesulphonyl chloride

N-m-tolylacetamide (1.0 g; 6.7 mmol) are added batchwise to 2.2 ml of chlorosulphonic acid. This mixture is heated to 60° C. for 2 hours and then poured onto ice water. It is extracted three times with ethyl acetate, the combined organic phases are dried with sodium sulphate and the solvent is distilled off using the rotary evaporator. A yellow oil remains.

Yield: 1.47 g (89%) $R_f$ value: 0.62 (silica gel, dichloromethane/ethanol 9:1) $C_9H_{10}NO_3S$ (247.70) Mass spectrum: $(M+H)^{30} =247/249$ (chlorine isotope)

(b) N-[3-methyl-4-(pyrrolidine-1-sulphonyl)-phenyl]-acetamide 1.45 g of 4-acetylamino-2-methyl-benzenesulphonyl chloride (5.85 mmol) at 0° C. are suspended in 19 ml sodium hydroxide solution (1 M) and then 0.51 ml pyrrolidine (6.47 mmol), dissolved in 9 ml acetone, are added dropwise within half an hour. The solution is heated to ambient temperature overnight and then acidified with hydrochloric acid (2 M). The suspension is extracted twice with ethyl acetate. The combined organic phases are dried over sodium sulphate and evaporated down. A brown oil remains.

Yield: 1.25 g (76%) $R_f$ value: 0.56 (silica gel, dichloromethane/ethanol 9:1) $C_{13}H_{18}N_2O_3S$ (282.36) Mass spectrum: $(M+H)^{30}=283$ (c) 3-methyl-4-(pyrrolidine-1-sulphonyl)-phenylamine 0.6 g of N-[3-methyl-4-(pyrrolidine-1-sulphonyl)-phenyl]-acetamide (2.13 mmol) are dissolved in 5 ml of ethanol and then 10 ml hydrochloric acid (6 N) are added thereto at ambient temperature. The mixture is stirred overnight at ambient temperature and then extracted three times with dichloromethane. The combined organic phases are washed successively with 5% sodium hydrogen carbonate solution and water. The aqueous phase is re-extracted with dichloromethane and combined with the dichloromethane phase already present, dried over sodium sulphate and evaporated down. A yellow oil is obtained which slowly crystallises out.

Yield: 430 mg (84%) $R_f$ value: 0.80 (silica gel, dichloromethane/ethanol 9:1) $C_{11}H_{16}N_2O_2S$ (240.32) Mass spectrum: $(M+H)^+=241$ (d) benzyl(R)-2-(hydroxy-1-{[3-methyl-4-(pyrrolidine-1-sulphonyl)-phenylcarbamoyl]-methyl}-ethyl)-carbamate 500 mg 3-methyl-4-(pyrrolidine-1-sulphonyl)-phenylamine (2.08 mmol) are dissolved in 40 ml dichloromethane and at 0° C. 1.04 ml trimethylaluminium in toluene (2 M, 2.08 mmol) are slowly added dropwise. After 15 minutes a solution of 489 mg benzyl(R)-(5-oxo-tetrahydrofuran-3-yl)-carbamate in 20 ml dichloromethane is added and the mixture is stirred for three days at ambient temperature. The mixture is then evaporated to dryness and taken up with 100 ml hydrochloric acid (0.5 N) and extracted three times with diethyl ether. The combined organic phases are dried over sodium sulphate and evaporated down. The residue is purified by reversed-phase HPLC.

Yield: 210 mg (21%) $R_t$ value: 4.45 min $C_{22}H_{27}N_3O_6S$ (461.53) Mass spectrum: $(M+H)^+=476$ (e) benzyl(R)-{1-[3-methyl-4-(pyrrolidine-1-sulphonyl)-phenyl]-5-oxo-pyrrolidin-3-yl}-carbamate 210 mg benzyl(R)-2-(hydroxy-1-{[3-methyl-4-(pyrrolidine-1-sulphonyl)-phenylcarbamoyl]-methyl}-ethyl)-carbamate (442 µmol) are dissolved in 5 ml THF and a solution of 203 mg di-tert.-butylazodicarboxylate (883 µmol) and 220 µl tributylphosphine (883 µmol) in 5 ml THF is added dropwise thereto. The mixture is stirred overnight at ambient temperature and then evaporated to dryness, acidified with TFA and purified by reversed phase HPLC.

Yield: 48 mg (24%) $R_t$ value: 4.88 min $C_{23}H_{27}N_3O_5S$ (457.54) Mass spectrum: $(M+H)^+=458$ (f) (R)-4-amino-1-[3-methyl-4-(pyrrolidine-1-sulphonyl)-phenyl]-pyrrolidin-2-one 45 mg (98 µmol) benzyl(R)-{1-[3-methyl-4-(pyrrolidine-1-sulphonyl)-phenyl]-5-oxo-pyrrolidin-3-yl}-carbamate are dissolved in 10 ml of methanol, combined with 25 mg palladium on charcoal and hydrogenated for 8 hours in a Parr apparatus at 3 bar hydrogen pressure at ambient temperature.

The mixture is filtered off from the catalyst and evaporated to dryness using the rotary evaporatory.

Yield: quantitative $R_t$ value: 3.50 min $C_{15}H_{21}N_3O_3S$ (323.41)

(g) (R)-5-bromo-thiophene-2-carboxylic acid-{1-[3-methyl-4-(pyrrolidine-1-sulphonyl)-phenyl]-5-oxo-Pyrrolidin-3-yl}-amide Prepared analogously to Example 1e from 5-bromo-thiophene-2-carboxylic acid and (R)-4-amino-1-[3-methyl-4-(pyrrolidine-1-sulphonyl)-phenyl]-pyrrolidin-2-one with TBTU and NMM in DMF and subsequent purification by reversed-phase chromatography.

Yield: 40% $R_t$ value: 4.96 min $C_{20}H_{22}BrN_3O_4S_2$ (512.44) Mass spectrum: $(M+H)^+=512/514$ (bromine isotope)

The following compound was prepared analogously:

| No. | Structural formula Name | Yield | Mass peak(s) | $R_f$ value or $R_t$ |
|---|---|---|---|---|
| 94 | (R)-5-ethynyl-thiophene-2-carboxylic acid-{1-[3-methyl-4-(3-oxo-morpholin-4-yl)-phenyl]-5-oxo-pyrrolidin-3-yl}-amide | Σ: 1.2% | (M + H)⁺ = 458 | 4.75 min |
| 95 | (R)-5-bromo-thiophene-2-carboxylic acid-{5-oxo-1-[4-(pyrrolidine-1-carbonyl)-phenyl]-pyrrolidin-3-yl}-amide | Σ: 2.7% | (M + H)⁺ = 462/464 (bromine isotope) | 2.75 min |
| 96 | (R)-5-chloro-thiophene-2-carboxylic acid-{5-oxo-1-[4-(pyrrolidine-1-carbonyl)-phenyl]-pyrrolidin-3-yl}-amide | Σ: 3.4% | (M + H)⁺ = 418/420 (chlorine isotope) | 2.72 min |

EXAMPLE 97

5-bromo-thiophene-2-carboxylic acid-{(3R)-1-[3-methyl-4-((2S)-2-pyrrolidin-1-ylmethyl-pyrrolidine-1-carbonyl)-phenyl]-5-oxo-pyrrolidin-3-yl}-amide (as a trifluoroacetate salt)

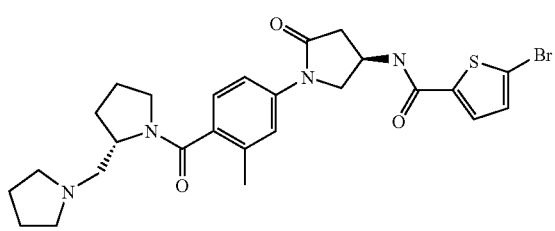

(a) tert.-butyl 4-benzylamino-2-methyl-benzoate tert.-butyl 4-bromo-2-methyl-benzoate (12 g; 43.4 mmol), caesium carbonate (21.2 g, 65 mmol), palladium(II)-acetate (1 g, 4.45 mmol) and BINAP (2.37 g, 4.40 mmol) are suspended in 150 ml of toluene under a nitrogen atmosphere and stirred for 10 minutes at ambient temperature. Then benzylamine (5.7 ml, 52.1 mmol) is added dropwise and the mixture is heated to 100° C. for two days. The mixture is then cooled, filtered to remove undissolved matter and evaporated to dryness. The oily residue is purified by chromatography (silica gel, petroleum ether/ethyl acetate 98:2). White crystals are obtained.

Yield: 10.15 g (79%) $R_f$ value: 0.62 (silica gel, petroleum ether/ethyl acetate 1:1) $C_{19}H_{23}NO_2$ (297.39) Mass spectrum: (M+H)⁺=298

(b) tert.-butyl 4-amino-2-methyl-benzoate

This is prepared analogously to Example 93f from tert.-butyl 4-benzylamino-benzoate by catalytic hydrogenation in ethanol.

Yield: 82% $R_f$ value: 0.72 (silica gel, dichloromethane/methanol 50:1) $C_{12}H_{17}NO_2$ (207.27) Mass spectrum: (M+H—C(CH$_3$)$_3$)⁺=152

(c) tert.-butyl(R)-4-(3-benzyloxycarbonylamino-4-hydroxy-butyrylamino)-2-methyl-benzoate This is prepared analogously to Example 93d from tert.-butyl 4-amino-benzoate and benzyl(R)-(5-oxo-tetrahydrofuran-3-yl)-carbamate by reaction with trimethylaluminium in dichloromethane.

Yield: 28% $R_f$ value: 3.15 min $C_{24}H_{30}N_2O_6$ (442.51) Mass spectrum: $(M+H)^+=443$ (d) tert.-butyl(R)-4-(4-benzyloxycarbonylamino-2-oxo-pyrrolidin-1-yl)-2-methyl-benzoate This is prepared analogously to Example 93e from tert.-butyl(R)-4-(3-benzyloxycarbonylamino-4-hydroxy-butyrylamino)-2-methyl-benzoate.

Yield: 80% $R_f$ value: 3.45 min $C_{24}H_{28}N_2O_5$ (424.49) Mass spectrum: $(M+H)^+=425$ (e) tert.-butyl(R)-4-(4-amino-2-oxo-pyrrolidin-1-yl)-2-methyl-benzoate This is prepared analogously to Example 93f from tert.-butyl(R)-4-(4-benzyloxycarbonylamino-2-oxo-pyrrolidin-1-yl)-2-methyl-benzoate by catalytic hydrogenation.

Yield: 74% $R_f$ value: 2.44 min $C_{16}H_{22}N_2O_3$ (290.36) Mass spectrum: $(M+H)^+=291$ (f) tert.-butyl(R)-4-[(5-bromo-thiophene-2-carbonyl)-amino]-2-oxo-pyrrolidin-1-yl)-2-methyl-benzoate This is prepared analogously to Example 93g from tert.-butyl(R)-4-(4-amino-2-oxo-pyrrolidin-1-yl)-2-methyl-benzoate and 5-bromo-thiophene-2-carboxylic acid.

Yield: 81% $R_f$ value: 3.51 min $C_{21}H_{23}BrN_2O_4S$ (479.39) Mass spectrum: $(M-H)^-=477/479$ (bromine isotope)

(g) (R)-4-[(5-bromo-thiophene-2-carbonyl)-amino]-2-oxo-pyrrolidin-1-yl)-2-methyl-benzoic acid tert.-butyl(R)-4-[(5-bromo-thiophene-2-carbonyl)-amino]-2-oxo-pyrrolidin-1-yl)-2-methyl-benzoate (96 mg; 200 μmol) is dissolved in 1 ml dichloromethane and combined with 0.5 ml trifluoroacetic acid. The mixture is stirred for 1.5 hours at ambient temperature and then evaporated to dryness. Yellowish crystals were obtained.

Yield: 86 mg (quantitative) $R_f$ value: 4.39 min $C_{17}H_{15}BrN_2O_4S$ (423.28)

(h) 5-bromo-thiophene-2-carboxylic acid-{(3R)-1-[3-methyl-4-((2S)-2-pyrrolidin-1-ylmethyl-pyrrolidine-1-carbonyl)-phenyl]-5-oxo-pyrrolidin-3-yl}-amide (as a trifluoroacetate salt)

Prepared analogously to Example 1e from (R)-4-[(5-bromo-thiophene-2-carbonyl)-amino]-2-oxo-pyrrolidin-1-yl)-2-methyl-benzoic acid and (S)-1-(2-pyrrolidinylmethyl)-pyrrolidine with TBTU and NMM in DMF and subsequent purification by reversed-phase chromatography.

Yield: 62% $R_f$ value: 4.23 min $C_{26}H_{31}BrN_4O_3S$ (559.53) Mass spectrum: $(M+H)^+=559/561$ (bromine isotope)

The following compounds were prepared analogously:

| No. | Structural formula Name | Yield | Mass peak(s) | $R_f$-value or $R_t$ |
|---|---|---|---|---|
| 98 | 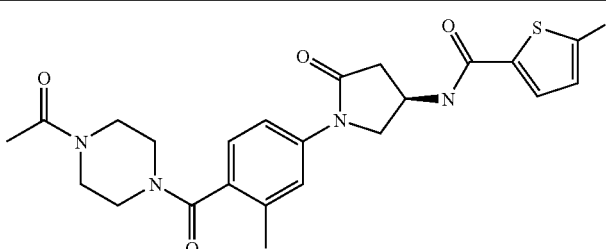 (R)-5-bromo-thiophene-2-carboxylic acid-{1-[4-(4-acetyl-piperazine-1-carbonyl)-3-methyl-phenyl]-5-oxo-pyrrolidin-3-yl}-amide | Σ: 6.6 | $(M+H)^+ = 433/435$ (bromine isotope) | 3.90 min |
| 99 | 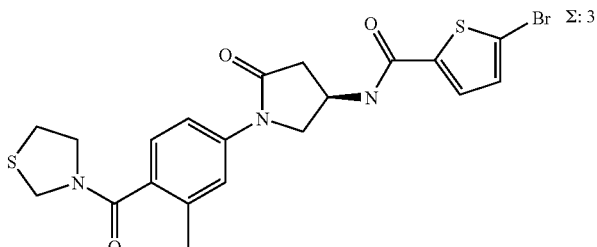 (R)-5-bromo-thiophene-2-carboxylic acid-{1-[3-methyl-4-(thiazolidine-3-carbonyl)-phenyl]-5-oxo-pyrrolidin-3-yl}-amide | Σ: 3.3% | $(M+H)^+ = 494/496$ (bromine isotope) | 4.49 min |

The invention claimed is:
1. A compound of the formula

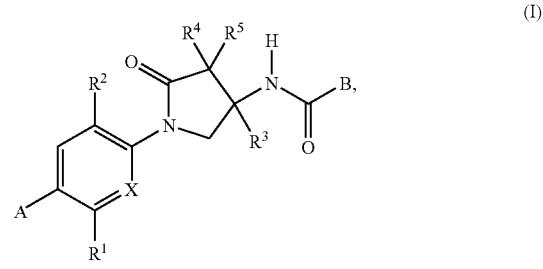

(I)

wherein:
A denotes a 4- to 7-membered cycloalkyleneiminocarbonyl or cycloalkyleneiminosulphonyl group, while
the cycloalkyleneimino moiety in the carbon skeleton may be substituted by one or two fluorine atoms, one or two $C_{1-3}$-alkyl, $C_{2-3}$-alkenyl, $C_{2-3}$-akynyl, hydroxy-$C_{1-3}$-alkyl, $C_{1-3}$-alkyloxy-$C_{1-3}$-alkyl, phenyl-$C_{1-3}$-alkyl, 1,1-diphenyl-$C_{1-3}$alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cyclo-alkyleneimino, trifluoromethylcarbonylamino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or
a methylene group in the 3-position of a 5-membered cycloalkyleneimino group may be replaced by a sulphur atom, a sulphinyl or sulphonyl group or
a methylene group in the 4-position of a 6- or 7-membered cycloalkyleneimino group may be replaced by an oxygen or sulphur atom, a carbonyl, sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the optionally substituted —NH group may be replaced by a carbonyl, sulphinyl or sulphonyl group, with the proviso that
during the substitution of the 6- to 7-membered cycloalkyleneimino groups, wherein a methylene group is replaced by an oxygen or sulphur atom, a sulphinyl or sulphonyl group, two heteroatoms are separated from one another by at least two carbon atoms,
a 5- to 7-membered cycloalkenyleneiminocarbonyl or cycloalkenyleniminosulphonyl group optionally substituted by one or two $C_{1-3}$-alkyl, hydroxy-$C_{1-3}$-alkyl, $C_{1-5}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, wherein the double bond is not bound to a nitrogen atom and may be fused to a 5- or 6-membered heteroaryl group,
an aminocarbonyl or aminosulphonyl group optionally substituted by one or two $C_{1-5}$-alkyl, $C_{2-3}$-alkenyl, $C_{2-3}$-alkynyl or $C_{3-6}$-cycloalkyl groups,
while the substituents may be identical or different and
in each case one of the $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-3}$-alkyl-aminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, or a group of formula

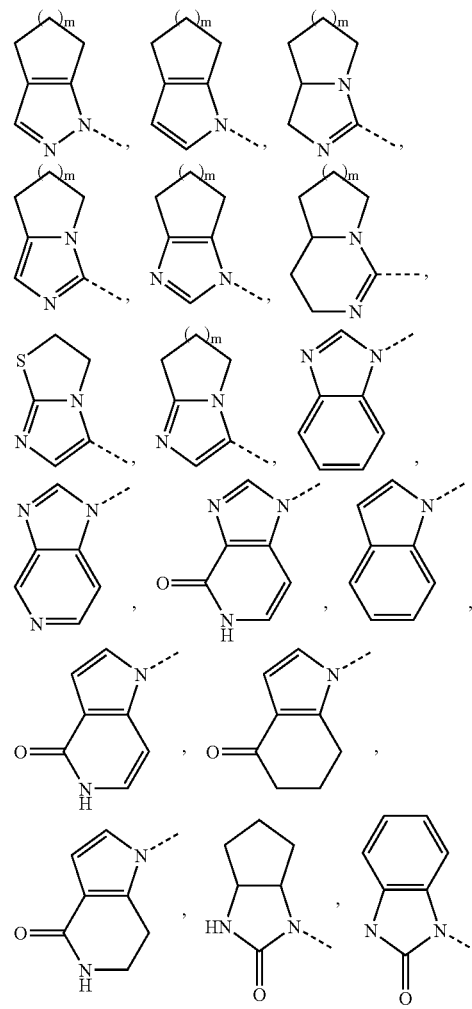

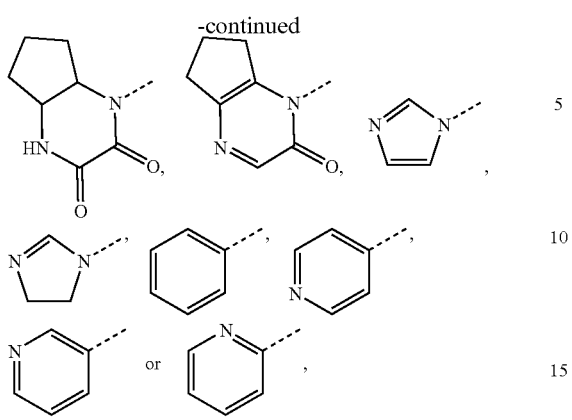

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkyl-sulphonyl, $C_{1-3}$-alkyl-sulphonyl-$C_{1-3}$-alkyl, aminosulphonyl, $C_{1-3}$-alkylsulphonyl-$C_{1-3}$-alkyl, $C_{1-3}$-alkylsulphonylamino-$C_{1-3}$-alkyl, $C_{1-3}$-alkylsulphonylamino, $C_{1-3}$-alkylcarbonylamino-$C_{1-3}$-alkyl, $C_{1-3}$-alkylcarbonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, hydroxy-$C_{1-3}$-alkyl, $C_{1-3}$-alkoxy-$C_{1-3}$-alkyl, a 4- to 7-membered cycloalkyleneimino-$C_{1-3}$-alkyl, morpholin-$C_4$-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH— group, $R^3$ denotes a hydrogen atom or a $C_{1-3}$-alkyl group, $R^4$ and $R^5$ each independently of one another denote
a hydrogen atom, a hydroxy group, an $OR^9$ group, a $C_{2-6}$-alkenyl or $C_{2-6}$-alkynyl group,
a straight-chain or branched $C_{1-6}$-alkyl group,
while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_5$-al kylcarbonyloxy, $C_5$-al kyloxycarbonyloxy, carboxy-$C_5$-alkyloxy, $C_{1-5}$-alkyloxycarbonyl-$C_{1-5}$-al kyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N13 ($C_{1-5}$-alkylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to the —$NR^7$ group may be replaced by a carbonyl group, a phenyl or heteroaryl group
which may optionally be mono-to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group, a 3- to 7-membered cycloalkyl, cycloalkyleneimino, cycloalkyl-$C_{1-5}$-alkyl or cycloalkyleneimino-$C_{1-3}$-alkyl group,
wherein in 4- to 7-membered cyclic groups in the cyclic moiety a methylene group may optionally be replaced by an —$N(R^7)$ group, an oxygen or sulphur atom or a —S(O) or —$S(O)_2$ group, or
wherein in 4- to 7-membered cyclic groups in the cyclic moiety two adjacent methylene groups together may optionally be replaced by a 13 C(O) $N(R^8)$ or —$S(O)_2N(R^8)$ group, or
wherein in 6- to 7-membered cyclic groups in the cyclic moiety three adjacent methylene groups together may optionally be replaced by a substituted $OC(O)N(R^8)$ or —$N(R^8)C(O)N(R^8)$ or —$N(R^8)S(O)_2N(R^8)$ group,
with the proviso that a 3- to 7-membered cycloalkyl, cycloalkyleneimino, cycloalkyl-$C_{1-5}$-alkyl or cycloalkyleneimino-$C_{1-3}$-alkyl group wherein two heteroatoms selected from oxygen and nitrogen are separated from one another by precisely one optionally substituted —$CH_2$ group, is excluded,
while a 3- to 7-membered cycloalkyl, cycloalkyleneimino, cycloalkyl- $C_{1-5}$-alkyl or cycloalkyleneimino-$C_{1-3}$-alkyl group may be substituted at one or two —$CH_2$ groups by one or two $C_{1-3}$-alkyl groups in each case, with the proviso that $R^4$ and $R^5$ may not simultaneously be defined as hydroxy or $OR^9$ groups, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or a —N($R^7$), or a carbonyl, sulphinyl or sulphonyl group, and/or two directly adjacent methylene groups of a $C_{4-8}$-cycloalkyl group may together be replaced by a —C(O)N($R^8$) or —S(O)$_2$N($R^8$) group, and/or three directly adjacent methylene groups of a $C_{6-8}$-cycloalkyl group may together be replaced by a —OC(O)N($R^8$), —N($R^8$)C(O)N($R^8$) or —N($R^8$)S(O)$_2$N($R^8$) group, while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not linked to another carbon atom by a double bond, may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino groups, with the proviso that a $C_{3-8}$-cycloalkyl or $C_{3-8}$-cycloalkenyl group of this kind formed from $R^4$ and $R^5$ together, wherein two heteroatoms in the cyclic group comprising oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a heteroatom selected from among oxygen, nitrogen, sulphur and halogen atom bound directly to the cyclic group, is separated from another heteroatom selected from among oxygen, nitrogen and sulphur, with the exception of the sulphone group, by precisely one optionally substituted methylene group, and/or wherein two oxygen atoms are directly joined together, is excluded, $R^7$ in each case independently of one another denotes a hydrogen atom, a hydroxy, a formyl, a $C_{1-5}$-alkyl, $C_{1-5}$-alkylcarbonyl, $C_{1-5}$-alkyloxycarbonyl or $C_{1-5}$-alkylsulphonyl group, $R^8$ in each case independently of one another denotes a hydrogen atom or a $C_{1-5}$alkyl group, $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —NR$^7$ group and additionally a methylene group adjacent to the —NR$^7$ group may be replaced by a carbonyl group, with the proviso that replacement of hydrogen atoms of the first carbon atom of the straight-chain or branched $C_{1-6}$-alkyl group by substituents from the group comprising oxygen, sulphur or nitrogen is excluded, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$alkyl group, wherein in 4- to 7-membered cyclic groups in the cyclic moiety a methylene group may optionally be replaced by a —N($R^7$) group, an oxygen or sulphur atom or a —S(O) or —S(O)$_2$ group, or wherein in 4- to 7-membered cyclic groups in the cyclic moiety two adjacent methylene groups together may optionally be replaced by a 13 C(O)N($R^8$) or —S(O)$_2$N($R^8$) group, or wherein in 6- to 7-membered cyclic groups in the cyclic moiety three adjacent methylene groups together may optionally be replaced by a substituted —OC(O)N($R^8$) or —N($R^8$)C(O)N($R^8$) or —N($R^8$)S(O)$_2$N($R^8$) group, with the proviso that a 3- to 7-membered cycloalkyl, cycloalkyl-$C_{1-5}$-alkyl or cycloalkyleneimino-$C_{2-3}$-alkyl group wherein two heteroatoms selected from oxygen and nitrogen are separated from one another by precisely one optionally substituted —CH$_2$ group, is excluded, while a 3- to 7-membered cycloalkyl, cycloalkyl-C$_{1-5}$-alkyl or cycloalkyleneimino-C$_{2-3}$-alkyl group may be substituted at one or two -CH$_2$ groups by one or two C$_{1-3}$-alkyl groups in each case, B denotes a group of formula

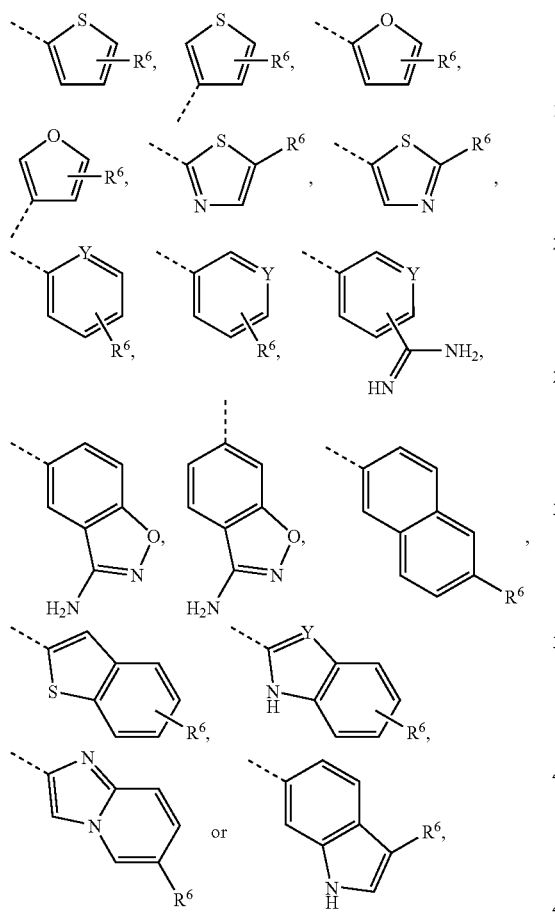

Y denotes a nitrogen atom or a CH— group,

R$^6$ denotes a hydrogen, a halogen atom, a nitrile group, a C$_{2-3}$-alkenyl, C$_{2-3}$-alkynyl, a C$_{1-3}$-alkyl group, or a C$_{1-3}$-alkoxy group, while the hydrogen atoms of the C$_{1-3}$-alkyl or C$_{1-3}$-alkoxy group may optionally be wholly or partly replaced by fluorine atoms, while the 6-membered heteroaryl group contains one, two or three nitrogen atoms and the 5-membered heteroaryl group contains an imino group optionally substituted by a C$_{1-3}$-alkyl, phenyl or phenyl-C$_{1-3}$-alkyl group, or an oxygen or sulphur atom or an imino group optionally substituted by a C$_{1-3}$-alkyl, phenyl, amino-C$_{2-3}$-alkyl, C$_{1-3}$-alkylamino-C$_{2-3}$-alkyl, di-(C$_{1-3}$-alkyl)-amino-C$_{2-3}$-alkyl, a C$_{3-6}$-cycloalkyleneimino-C$_{1-3}$-alkyl or phenyl-C$_{1-3}$-alkyl group or an oxygen or sulphur atom and additionally a nitrogen atom or an imino group optionally substituted by a C$_{1-3}$-alkyl or phenyl-C$_{1-3}$-alkyl group and two or three nitrogen atoms, and a phenyl ring optionally substituted by a fluorine, chlorine or bromine atom, a C$_{1-3}$-alkyl, hydroxy, C$_{1-3}$-alkyloxy group, amino, C$_{1-3}$-alkylamino, di-(C$_{1-3}$-alkyl)-amino or C$_{3-6}$-cycloalkyleneimino group may be fused to the heteroaryl groups via two adjacent carbon atoms and the bond is effected via a nitrogen atom or a carbon atom of the heterocyclic moiety or a fused-on phenyl ring, while the alkyl, alkenyl, alkynyl and alkoxy groups which have more than two carbon atoms may be straight-chain or branched and the alkyl groups in dialkylated groups may be identical or different, and the hydrogen atoms of the methyl or ethyl groups may be wholly or partly replaced by fluorine atoms, or a tautomer or salt thereof.

2. A compound of the formula I according to claim 1, wherein:

A denotes a 4- to 7-membered cycloalkyleneiminocarbonyl or cycloalkyleneiminosulphonyl group, while the cycloalkyleneimino moiety in the carbon skeleton may be substituted by one or two fluorine atoms, one or two C$_{1-3}$-alkyl, C$_{2-3}$-alkenyl, C$_{2-3}$-alkynyl, hydroxy-C$_{1-3}$-alkyl, C$_{1-3}$-alkyloxy-C$_{1-3}$-alkyl, phenyl-C$_{1-3}$-alkyl, 1,1-diphenyl-C$_{1-3}$-alkyl, heteroaryl-C$_{1-3}$-alkyl, amino-C$_{1-3}$-alkyl, C$_{3-6}$-cycloalkylamino-C$_{1-3}$-alkyl, phenylamino-C$_{1-3}$-alkyl, C$_{1-5}$-alkylamino-C$_{1-3}$-alkyl, di-(C$_{1-5}$-alkyl)-amino-C$_{1-5}$-alkyl, N—(C$_{3-6}$-cycloalkyl)-C$_{1-3}$-alkylamino-C$_{1-3}$-alkyl, a 4- to 7-membered cycloalkyleneimino-C$_{1-3}$-alkyl, N—(C$_{1-3}$-alkylcarbonyl)-C$_{1-3}$-alkylamino-C$_{1-3}$-alkyl, carboxy-C$_{1-3}$-alkyl, C$_{1-3}$-alkyloxycarbonyl-C$_{1-3}$-alkyl, aminocarbonyl-C$_{1-3}$-alkyl, C$_{1-3}$-alkylaminocarbonyl-C$_{1-3}$-alkyl, di-(C$_{1-3}$-alkyl)-aminocarbonyl-C$_{1-3}$-alkyl, a 4- to 7-membered cycloalkyleneiminocarbonyl-C$_{1-3}$-alkyl, C$_{1-5}$-alkyloxycarbonylamino-C$_{1-3}$-alkyl, C$_{1-3}$-alkylcarbonylamino-C$_{1-3}$-alkyl, C$_{1-5}$-alkylsulphonylamino-C$_{1-3}$-alkyl, aminocarbonylamino-C$_{1-3}$-alkyl, C$_{1-5}$-alkylaminocarbonylamino-C$_{1-3}$-alkyl, di-(C$_{1-3}$-alkyl)-aminocarbonylamino-C$_{1-3}$-alkyl, C$_{1-5}$-alkylsulphonylamino, C$_{1-5}$-alkylaminocarbonylamino, carboxy, C$_{1-3}$-alkyloxycarbonyl, benzyloxycarbonyl, C$_{1-3}$-alkylcarbonyl, aminocarbonyl, C$_{1-3}$-alkylaminocarbonyl, di-(C$_{1-3}$-alkyl)-aminocarbonyl, N—(C$_{3-7}$-cycloalkyl)-C$_{1-5}$-alkylaminocarbonyl, N—(phenyl-C$_{1-3}$-alkyl)-C$_{1-5}$-alkylaminocarbonyl, a 4- to 7-membered cycloalkyleneiminocarbonyl, aminocarbonyl-C$_{1-3}$-alkylaminocarbonyl, hydroxy, C$_{1-3}$-alkyloxy, allyloxy, propargyloxy, benzyloxy, amino, C$_{1-3}$-alkylamino, di-(C$_{1-3}$-alkyl)-amino, a 4- to 7-membered cycloalkyleneimino, trifluoromethylcarbonylamino, N—(C$_{1-3}$-alkyl)-piperazin-4-yl-C$_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom, a sulphinyl or sulphonyl group or a methylene group in the 4-position of a 6- or 7-membered cycloalkyleneimino group may be replaced by an oxygen or sulphur atom, a carbonyl, sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the optionally substituted —NH group may be replaced by a carbonyl, sulphinyl or sulphonyl group, with the proviso that in the substitution of the 6- to 7-membered cycloalkyleneimino groups, wherein a methylene group is replaced by an oxygen or sulphur atom, a sulphinyl or sulphonyl group, two heteroatoms are separated from one another by at least two carbon atoms, a 5- to 7-membered cycloalkenyleneiminocarbonyl or cycloalkenyleneiminosulphonyl group optionally substituted by one or two $C_{1-3}$-alkyl, hydroxy-$C_{1-3}$-alkyl, $C_{1-5}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, $C_{2-3}$-alkenyl, $C_{2-3}$-alkynyl, or $C_{3-6}$-cycloalkyl groups, while the substituents may be identical or different and in each case one of the $C_{1-5}$-alkyl groups may be substituted by one or two hydroxyl-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-3}$-alkylaminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, or a group of formula

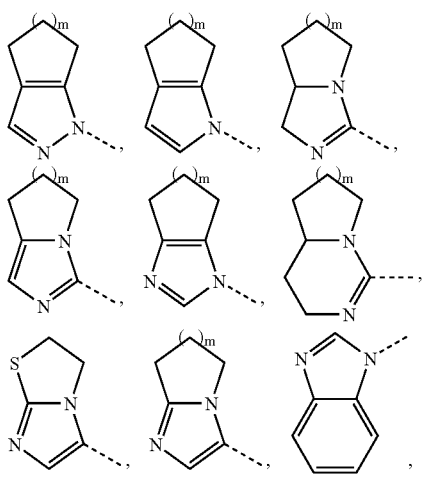

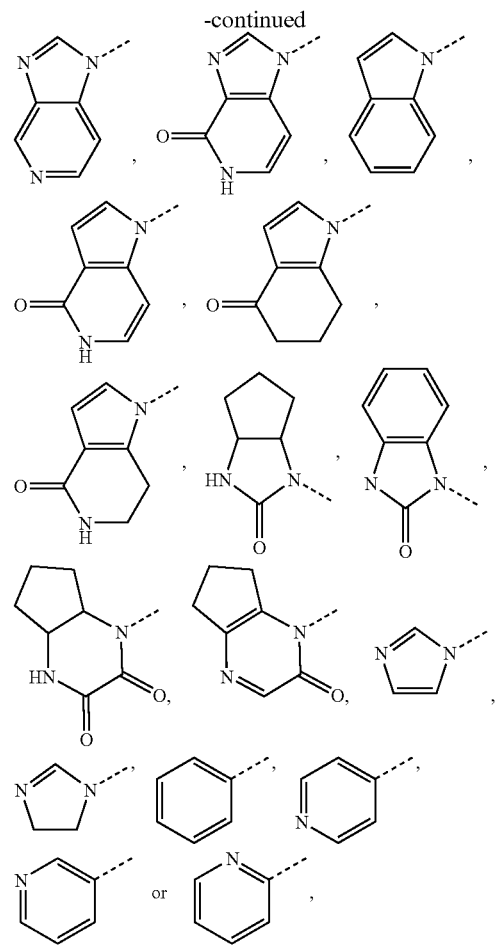

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkyl-suiphonyl, $C_{1-3}$-alkyl-sulphonyl-$C_{1-3}$-alkyl, aminosuiphonyl, $C_{1-3}$-alkylsulphonyl-$C_{1-3}$-alkyl, $C_{1-3}$-alkylsulphonylamino-$C_{1-3}$-alkyl, $C_{1-3}$-alkylsulphonylamino, $C_{1-3}$-alkylcarbonylamino-$C_{1-3}$-alkyl, $C_{1-3}$-alkylcarbonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, hydroxy-$C_{1-3}$-alkyl, $C_{1-5}$-alkoxy-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH— group, $R^3$ denotes a hydrogen atom or a $C_{1-3}$-alkyl group, $R^4$ and $R^5$ each independently of one another denote
a hydrogen atom, a hydroxy group, an $OR^9$ group, a $C_{2-6}$-alkenyl or $C_{2-6}$-alkynyl group, a straight-chain or branched $C_{1-6}$-alkyl group,
  while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group,
    while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —NR$^7$ group and additionally a methylene group adjacent to the —NR$^7$ group may be replaced by a carbonyl group,
a phenyl or heteroaryl group
  which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
a phenyl-$C_{1-5}$-alkyl or heteroaryl-$C_{1-5}$-alkyl group,
  which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group,
a 3- to 7-membered cycloalkyl, cycloalkyleneimino, cycloalkyl-$C_{1-5}$-alkyl or cycloalkyleneimino-$C_{1-3}$-alkyl group,
  wherein in 4- to 7-membered cyclic groups in the cyclic moiety a methylene group may optionally be replaced by an —N(R$^7$) group, an oxygen or sulphur atom or a —S(O) or —S(O)$_2$ group, or
  wherein in 4- to 7-membered cyclic groups in the cyclic moiety two adjacent methylene groups together may optionally be replaced by a —C(O)N(R$^8$) or —S(O)$_2$N(R$^8$) group, or
  wherein in 6- to 7-membered cyclic groups in the cyclic moiety three adjacent methylene groups together may optionally be replaced by a substituted —OC(O)N(R$^8$) or —N(R$^8$)C(O)N(R$^8$) or —N(R$^8$)S(O)$_2$N(R$^8$) group,
    with the proviso that a 3- to 7-membered cycloalkyl, cycloalkyleneimino, cycloalkyl-$C_{1-5}$-alkyl or cycloalkyleneimino-$C_{1-3}$-alkyl group wherein two heteroatoms selected from oxygen and nitrogen are separated from one another by precisely one optionally substituted —CH$_2$ group, is excluded,
    while a 3- to 7-membered cycloalkyl, cycloalkyleneimino, cycloalkyl- $C_{1-5}$-alkyl or cycloalkyleneimino-$C_{1-3}$-alkyl group may be substituted at one or two —CH$_2$ groups by one or two $C_{1-3}$-alkyl groups in each case,
  with the proviso that R$^4$ and R$^5$ may not simultaneously be defined as hydroxy or OR$^9$ groups, or
R$^4$ and R$^5$ together with the carbon atom to which they are bound form a $C_{3-8}$-cycloalkyl or $C_{3-8}$-cycloalkenyl group,
  while one of the methylene groups of a $C_{4-8}$-cycloalkyl group may be replaced by an oxygen or sulphur atom or an —N(R$^7$), or a carbonyl, sulphinyl or sulphonyl group, and/or
  two directly adjacent methylene groups of a $C_{4-8}$-cycloalkyl group may together be replaced by a —C(O)N(R$^8$) or —S(O)$_2$N(R$^8$) group, and/or
  three directly adjacent methylene groups of a $C_{6-8}$-cycloalkyl group may together be replaced by a —OC(O)N(R$^8$), —N(R$^8$)C(O)N(R$^8$) or —N(R$^8$)S(O)$_2$N(R$^8$) group,
  while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino groups,
  while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups,
  and 1 to 2 carbon atoms of a $C_{4-8}$-cycloalkenyl group which are not linked to another carbon atom by a double bond may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)$C_{1-5}$-alkylamino or $C_{3-6}$-cycloalkylcarbonylamino groups, with the proviso that a $C_{3-8}$-cycloalkyl or $C_{3-8}$-cycloalkenyl group of this kind formed from $R^4$ and $R^5$ together,
wherein two heteroatoms in the cyclic group comprising oxygen and nitrogen are separated from one another by precisely one optionally substituted —$CH_2$ group, and/or
wherein one or both methylene groups of the cyclic group which are directly connected to the carbon atom to which the groups $R^4$ and $R^5$ are bound, are replaced by a heteroatom selected from among oxygen, nitrogen and sulphur, and/or
wherein a heteroatom selected from among oxygen, nitrogen, sulphur and halogen atom bound directly to the cyclic group, is separated from another heteroatom selected from among oxygen, nitrogen and sulphur, with the exception of the sulphone group, by precisely one optionally substituted methylene group, and/or
wherein two oxygen atoms are directly joined together,
is excluded,
$R^7$ each independently of one another denote a hydrogen atom, a hydroxy, a formyl, a $C_{1-5}$-alkyl, $C_{1-5}$-alkylcarbonyl, $C_{1-5}$-alkyloxycarbonyl or $C_{1-5}$-alkylsulphonyl group,
$R^8$ each independently of one another denote a hydrogen atom or a $C_{1-5}$-alkyl group,
$R^9$ denotes a straight-chain or branched $C_{1-6}$-alkyl group,
while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)$C_{1-5}$-alkylamino or $C_{3-6}$-cycloalkylcarbonylamino group,
while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to the —$NR^7$ group may be replaced by a carbonyl group,
with the proviso that the replacement of hydrogen atoms of the first carbon atom of the straight-chain or branched $C_{1-6}$-alkyl group by substituents from the group comprising oxygen, sulphur or nitrogen is excluded,
a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
a 3- to 7-membered cycloalkyl, cycloalkyl-$C_{1-5}$-alkyl or cycloalkyleneimino-$C_{2-3}$-alkyl group,
wherein in 4- to 7-membered cyclic groups in the cyclic moiety a methylene group may optionally be replaced by a —$N(R^7)$ group, an oxygen or sulphur atom or a —$S(O)$ or —$S(O)_2$ group, or
wherein in 4- to 7-membered cyclic groups in the cyclic moiety two adjacent methylene groups together may optionally be replaced by a 13 $C(O)N(R^8)$ or —$S(O)_2N(R^8)$ group, or
wherein in 6- to 7-membered cyclic groups in the cyclic moiety three adjacent methylene groups together may optionally be replaced by a substituted —$OC(O)N(R^8)$ or —$N(R^8)C(O)N(R^8)$ or —$N(R^8)S(O)_2N(R^8)$ group,
with the proviso that a 3- to 7-membered cycloalkyl, cycloalkyl-$C_{1-5}$-alkyl or cycloalkyleneimino-$C_{2-3}$-alkyl group wherein two heteroatoms selected from oxygen and nitrogen are separated from one another by precisely one optionally substituted —$CH_2$ group, is excluded,
while a 3- to 7-membered cycloalkyl, cycloalkyl-$C_{1-5}$-alkyl or cycloalkyleneimino-$C_{2-3}$-alkyl group may be substituted at one or two —$CH_2$ groups by one or two $C_{1-3}$-alkyl groups in each case,
B denotes a group of formula

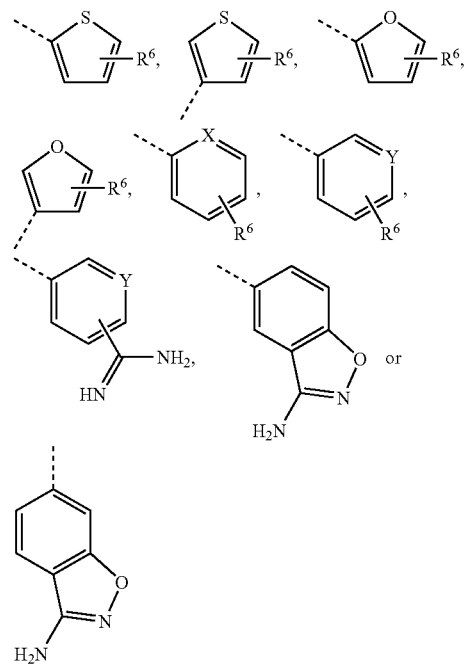

Y denotes a nitrogen atom or a CH— group,
$R^6$ denotes a hydrogen, a halogen atom, a nitrile group, a $C_{2-3}$-alkenyl, $C_{2-3}$-alkynyl, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms,
while
the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the heteroaryl groups via two adjacent carbon atoms and the bond is effected via a nitrogen atom or a carbon atom of the heterocyclic moiety or a fused-on phenyl ring, while the alkyl, alkenyl, alkynyl and alkoxy groups which have more than two carbon atoms may be straight-chain or branched and the alkyl groups in dialkylated groups may be identical or different, and the hydrogen atoms of the methyl or ethyl groups may be wholly or partly replaced by fluorine atoms, or a tautomer or salt thereof.

3. A compound of the formula I according to claim 1, wherein:

A denotes a 4- to 7-membered cycloalkyleneiminocarbonyl or cycloalkyleneiminosulphonyl group, while
the cycloalkyleneimino moiety in the carbon skeleton may be substituted by one or two fluorine atoms, one or two $C_{1-3}$-alkyl, $C_{2-3}$-alkenyl, $C_{2-3}$-alkynyl, hydroxyl-$C_{1-3}$-alkyl, $C_{1-3}$-alkyloxy-$C_{1-3}$-alkyl, phenyl-$C_{1-3}$-alkyl, 1,1-diphenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, trifluoromethylcarbonylamino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- or 7-membered cycloalkyleneimino group may be replaced by an oxygen or sulphur atom, a carbonyl, sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the optionally substituted —NH group may be replaced by a carbonyl, sulphinyl or sulphonyl group, with the proviso that in the substitution of the 6- to 7-membered cycloalkyleneimino groups, wherein a methylene group is replaced by an oxygen or sulphur atom, a sulphinyl or sulphonyl group, two heteroatoms are separated from one another by at least two carbon atoms, a 5- to 7-membered cycloalkenyleneiminocarbonyl or cycloalkenyleneiminosulphonyl group optionally substituted by one or two $C_{1-3}$-alkyl, hydroxy-$C_{1-3}$-alkyl, $C_{1-5}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, $C_{2-3}$-alkenyl, $C_{2-3}$-alkynyl, or $C_{3-6}$-cycloalkyl groups,
while the substituents may be identical or different and
in each case one of the $C_{1-5}$-alkyl groups may be substituted by one or two hydroxyl-$C_{1-3}$-alkyl, $C_{1-3}$-alkoxy-$C_{1-3}$-alkyl, benzyloxy-$c_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-3}$-alkylaminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, or a group of formula

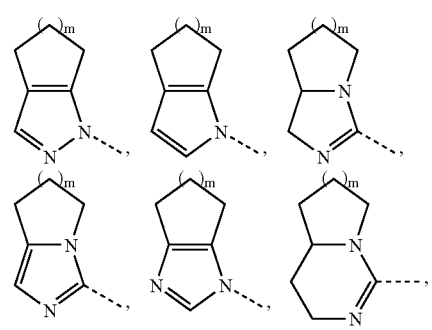

-continued which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkyl-sulphonyl, $C_{1-3}$-alkyl-sulphonyl-$C_{1-3}$-alkyl, aminosulphonyl, $C_{1-3}$-alkylsulphonyl-$C_{1-3}$-alkyl, $C_{1-3}$-alkylsulphonylamino-$C_{1-3}$-alkyl, $C_{1-3}$-alkylsulphonylamino, $C_{1-3}$-alkylcarbonylamino-$C_{1-3}$-alkyl, $C_{1-3}$-alkylcarbonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, hydroxy-$C_{1-3}$-alkyl, $C_{1-5}$-alkoxy-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a methyl group, X denotes a nitrogen atom or a CH— group, $R^3$ denotes a hydrogen atom or a $C_{1-3}$-alkyl group, $R^4$ and $R^5$ each independently of one another denote
  a hydrogen atom, a hydroxy group, an $OR^9$ group, a $C_{2-6}$-alkenyl or $C_{2-6}$-alkynyl group,
  a straight-chain or branched $C_{1-6}$-alkyl group,
    while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group,
    while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom or by a carbonyl, sulphinyl, sulphonyl or —$NR^7$ group and additionally a methylene group adjacent to the —$NR^7$ group may be replaced by a carbonyl group,
  a phenyl, heteroaryl, phenyl-$C_{1-5}$-alkyl or heteroaryl-$C_{1-5}$-alkyl group,
    which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
  a 3- to 7-membered cycloalkyl, cycloalkyleneimino, cycloalkyl-$C_{1-5}$-alkyl or cycloalkyleneimino-$C_{1-3}$-alkyl group,
    wherein in 4- to 7-membered cyclic groups in the cyclic moiety a methylene group may optionally be replaced by a —$N(R^7)$ group, an oxygen or sulphur atom or a —$S(O)$ or —$S(O)_2$ group, or
    wherein in 4- to 7-membered cyclic groups in the cyclic moiety two adjacent methylene groups together may optionally be replaced by a —$C(O)N(R^8)$ or —$S(O)_2N(R^8)$ group, or
    wherein in 6- to 7-membered cyclic groups in the cyclic moiety three adjacent methylene groups together may optionally be replaced by a substituted —$OC(O)N(R^8)$ or —$N(R^8)C(O)N(R^8)$ or —$N(R^8)S(O)_2N(R^8)$ group,
    with the proviso that a 3- to 7-membered cycloalkyl, cycloalkyleneimino, cycloalkyl-$C_{1-5}$-alkyl or cycloalkyleneimino-$C_{1-3}$-alkyl group wherein two heteroatoms selected from oxygen and nitrogen are separated from one another by precisely one optionally substituted —$CH_2$ group, is excluded,
    while a 3- to 7-membered cycloalkyl, cycloalkyleneimino, cycloalkyl-$C_{1-5}$-alkyl or cycloalkyleneimino-$C_{1-3}$-alkyl group may be substituted at one or two —$CH_2$ groups by one or two $C_{1-3}$-alkyl groups in each case,
  with the proviso that $R^4$ and $R^5$ may not simultaneously be defined as hydroxy or $OR^9$ groups, $R^7$ each independently of one another denote a hydrogen atom, a hydroxy, a formyl, a $C_{1-3}$-alkyl, $C_{1-3}$-alkylcarbonyl, $C_{1-3}$-alkyloxycarbonyl or $C_{1-3}$-alkylsulphonyl group, $R^8$ each independently of one another denote a hydrogen atom or a $C_{1-3}$-alkyl group $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-al kylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to the —$NR^7$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a C3- to 7-membered cycloalkyl, cycloalkyl-$C_{1-5}$-alkyl or cycloalkyleneimino-$C_{2-3}$alkyl group, wherein in 4- to 7-membered cyclic groups in the cyclic moiety a methylene group may optionally be replaced by an —N($R^7$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N($R^8$) or —S(O)$_2$N($R^8$) group, or wherein in 6- to 7-membered cyclic groups in the cyclic moiety three adjacent methylene groups together may optionally be replaced by a substituted —OC(O)N($R^8$) or —N($R^8$)C(O)N($R^8$) or —N($R^8$)S(O)$_2$N($R^8$) group, with the proviso that a 3- to 7-membered cycloalkyl, cycloalkyl-$C_{1-5}$-alkyl or cycloalkyleneimino-$C_{2-3}$-alkyl group wherein two heteroatoms selected from oxygen and nitrogen are separated from one another by precisely one optionally substituted —$CH_2$ group, is excluded, while a 3- to 7-membered cycloalkyl, cycloalkyl-$C_{1-5}$-alkyl or cycloalkyleneimino-$C_{2-3}$-alkyl group may be substituted at one or two $CH_2$ groups by one or two $C_{1-3}$-alkyl groups in each case, B denotes a group of formula

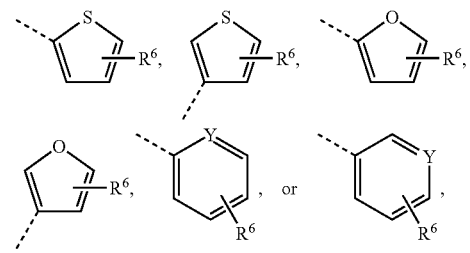

Y denotes a nitrogen atom or a CH— group, $R^6$ denotes a hydrogen, a halogen atom, an ethynyl, a methyl group, a methoxy group, while the hydrogen atoms of the methoxy group may optionally be wholly or partly replaced by fluorine atoms, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the heteroaryl groups via two adjacent carbon atoms and the bond is effected via a nitrogen atom or a carbon atom of the heterocyclic moiety or a fused-on phenyl ring, while the alkyl, alkenyl, alkynyl and alkoxy groups which have more than two carbon atoms may be straight-chain or branched and the alkyl groups in dialkylated groups may be identical or different, and the hydrogen atoms of the methyl or ethyl groups may be wholly or partly replaced by fluorine atoms, or a tautomer or salt thereof.

4. A compound of the formula I according to claim 1, wherein:

A denotes a 4- to 7-membered cycloalkyleneiminocarbonyl or cycloalkyleneiminosulphonyl group, while
the cycloalkyleneimino moiety in the carbon skeleton may be substituted by one or two fluorine atoms, one or two $C_{1-3}$-alkyl, hydroxy-$C_{1-3}$-alkyl, $C_{1-3}$-alkyloxy-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-5}$-alkylsulphonylamino-$C_{1-3}$-alkyl, aminocarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, N—($C_{1-3}$-alkyl)-piperazin-4-yl-$C_{1-3}$-alkyl, a phenyl or a 5- to 6-membered heteroaryl group, with the proviso that in the substitution of a methylene group adjacent to the imino group two heteroatoms are separated from one another by at least two carbon atoms, and/or
a methylene group in the 3-position of a 5-membered cycloalkyleneimino group may be replaced by a sulphur atom or
a methylene group in the 4-position of a 6- or 7-membered cycloalkyleneimino group may be replaced by an oxygen or sulphur atom, a sulphinyl or sulphonyl group or by an —NH group optionally substituted by a $C_{1-3}$-alkyl, hydroxy, formyl or $C_{1-3}$-alkylcarbonyl group, while additionally a methylene group adjacent to the optionally substituted —NH group may be replaced by a carbonyl, sulphinyl or sulphonyl group, with the proviso that
in the substitution of the 6- to 7-membered cycloalkyleneimino groups, wherein a methylene group is replaced by an oxygen or sulphur atom, a sulphinyl or sulphonyl group, two heteroatoms are separated from one another by at least two carbon atoms,
a 5- to 7-membered cycloalkenyleneiminocarbonyl or cycloalkenyleneiminosulphonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulphonyl group optionally substituted by one or two $C_{1-5}$-alkyl, or $C_{3-6}$-cycloalkyl groups,
while the substituents may be identical or different and in each case one of the $C_{1-5}$-alkyl groups may be substituted by one or two hydroxyl-$C_{1-3}$-alkyl, $C_{1-3}$-alkoxy-$C_{1-3}$-alkyl, amino-$C_{1-3}$-alkyl, di-($C_{1-3}$-alkyl)-amino-$C_{1-3}$-alkyl, a 4- to 7-membered cycloalkyleneimino-$C_{1-3}$-alkyl, aminocarbonyl, $C_{1-3}$-alkylaminocarbonyl, di-($C_{1-3}$-alkyl)-aminocarbonyl or a 4- to 7-membered cycloalkyleneiminocarbonyl group,
or a group of formula

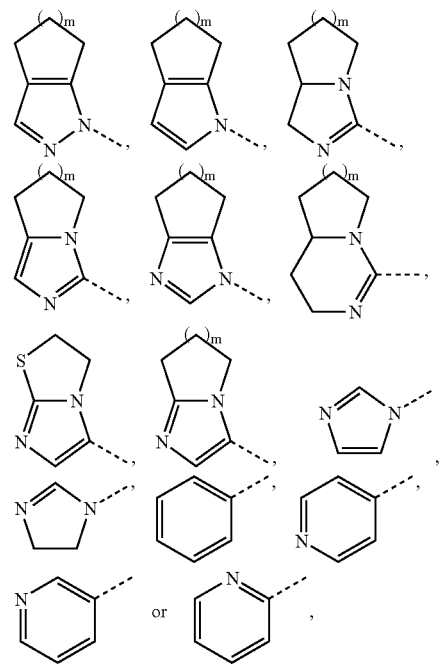

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkyl-sulphonyl, $C_{1-3}$-alkyl-sulphonyl-$C_{1-3}$-alkyl, aminosulphonyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di($C_{1-3}$-alkyl)-aminocarbonyl group and wherein
m denotes the number 1 or 2,
$R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group,
$R^2$ denotes a hydrogen or fluorine atom or a methyl group,
X denotes a nitrogen atom or a CH— group,
$R^3$ denotes a hydrogen atom or a $C_{1-3}$-alkyl group,
$R^4$ denotes a hydrogen atom,
a straight-chain or branched $C_{1-4}$-alkyl group,
while the hydrogen atoms of the straight-chain or branched $C_{1-4}$-alkyl group may optionally be wholly or partly replaced by fluorine atoms, and which may optionally be substituted by a $C_{1-3}$- alkyloxy group, while the hydrogen atoms of the $C_{1-3}$-alkyloxy group may optionally be wholly or partly replaced by fluorine atoms, $R^5$ denotes a hydrogen atom, a hydroxy group, an $OR^9$ group, a $C_{2-4}$-alkenyl or $C_{2-4}$alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, aminosulphonyl, $C_{1-5}$-alkylaminosulphonyl, di-($C_{1-5}$-alkyl)-aminosulphonyl, $C_{4-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to the —$NR^7$ group may be replaced by a carbonyl group a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, $R^7$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-6}$-cycloalkyleneiminocarbonyl, $C_{1-5}$-alkyloxycarbonylamino, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, while the 6- to 7-membered cyclic groups of the $C_{4-6}$-cycloalkyleneiminocarbonyl group in the cyclic moiety a methylene group in the 4-position of a 6- or 7-membered cycloalkyleneimino group may be replaced by an oxygen or sulphur atom, by a carbonyl, sulphinyl, sulphonyl or —$NR^7$ group and additionally a methylene group adjacent to the —$NR^7$ group may be replaced by a carbonyl group with the proviso that the replacement of hydrogen atoms of the first carbon atom of the straight-chain or branched $C_{1-4}$-alkyl group by substituents from the group comprising oxygen, sulphur or nitrogen is excluded, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

B denotes a group of formula

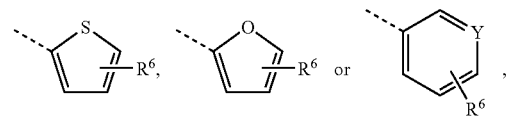

Y denotes a nitrogen atom or a CH— group, $R^6$ denotes a hydrogen, a halogen atom, an ethynyl, a methyl group, a methoxy group, while the hydrogen atoms of the methoxy group may optionally be wholly or partly replaced by fluorine atoms, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cyclo-alkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the heteroaryl groups via two adjacent carbon atoms and the bond is effected via a nitrogen atom or a carbon atom of the heterocyclic moiety or a fused-on phenyl ring, while the alkyl, alkenyl, alkynyl and alkoxy groups which have more than two carbon atoms may be straight-chain or branched and the alkyl groups in dialkylated groups may be identical or different, and the hydrogen atoms of the methyl or ethyl groups may be wholly or partly replaced by fluorine atoms, or a tautomer or salt thereof.

5. A compound of the formula I according to claim 1, wherein:

A denotes a 5- to 6-membered cycloalkyleneiminocarbonyl or cycloalkyleneiminosulphonyl group, while the cycloalkyleneimino moiety in the carbon skeleton may be substituted by one or two fluorine atoms, one or two $C_{1-3}$-alkyl, hydroxy-$C_{1-3}$-alkyl, $C_{1-3}$-alkyloxy-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a $C_{1-3}$-alkylcarbonylamino-$C_{1-3}$-alkyl, $C_{1-5}$-alkylaminocarbonylamino-$C_{1-3}$-alkyl, di-($C_{1-3}$-alkyl)-aminocarbonylamino-$C_{1-3}$-alkyl, $C_{1-5}$-alkylsulphonylamino, $C_{1-5}$-alkylaminocarbonylamino, carboxy, $C_{1-3}$-alkyloxycarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, hydroxy, $C_{1-3}$-alkyloxy, amino, $C_{1-3}$-alkylamino, di-($C_{1-3}$-alkyl)-amino, N—($C_{1-3}$-alkyl)-piperazin-C4-yl-$C_{1-3}$-alkyl, a phenyl or a 6-membered heteroaryl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- to 7-membered cycloalkyleneimino group may be replaced by an oxygen or sulphur atom or by an —NH group optionally substituted by a $C_{1-3}$-alkyl, hydroxy, formyl or $C_{1-3}$-alkylcarbonyl group, while additionally a methylene group adjacent to the optionally substituted —NH group may be replaced by a carbonyl group, with the proviso that in the substitution of the 6- to 7-membered cycloalkyleneimino groups, wherein a methylene group is replaced by an oxygen or sulphur atom, two heteroatoms are separated from one another by at least two carbon atoms, or A denotes a group of formula

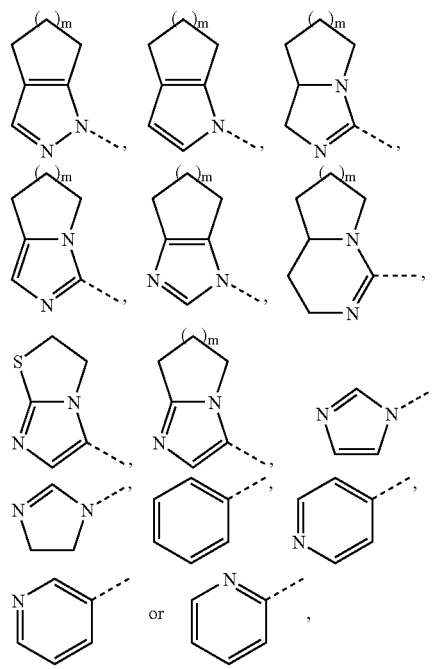

which may be substituted in each case at a carbon atom by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, $C_{1-3}$-alkyl-sulphonyl, $C_{1-3}$-alkyl-sulphonyl-$C_{1-3}$-alkyl, aminosuiphonyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)-piperazin-4-yl-$C_{1-3}$-alkyl, aminocarbonyl, $C_{1-3}$-alkylaminocarbonyl or di-($C_{1-3}$-alkyl)-aminocarbonyl group and wherein m denotes the number 1 or 2, $R^1$ denotes a hydrogen, fluorine, chlorine or bromine atom, a methyl or methoxy group, while the hydrogen atoms of the methyl or methoxy group may optionally be wholly or partly replaced by fluorine atoms, $R^2$ denotes a hydrogen or fluorine atom, X denotes a nitrogen atom or a OH- group, $R^3$ denotes a hydrogen atom or a $C_{1-3}$-alkyl group, $R^4$ denotes a hydrogen atom, $R^5$ denotes a hydrogen atom, a hydroxy group, an $OR^9$ group, a $C_{2-4}$-alkenyl or $C_{2-4}$alkynyl group, a straight-chain or branched $C_{1-4}$-alkyl group, while the hydrogen atoms may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{4-6}$-cycloalkyleneiminocarbonyl, amino, $C_{1-3}$-alkylamino, di-($C_{1-3}$-alkyl)-amino, $C_{1-3}$-alkylcarbonylamino, or $C_{1-3}$-alkylsulphonylamino group, a phenyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, a phenyl-$C_{1-3}$-alkyl, heteroaryl-$C_{1-3}$-alkyl- group, while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, and which may optionally be substituted in the $C_{1-3}$-alkyl moiety by a hydroxy, a $C_{1-3}$-alkyloxy group, while the hydrogen atoms of the $C_{1-3}$-alkyloxy group may optionally be wholly or partly replaced by fluorine atoms, a $C_{1-5}$-alkylcarbonyloxy, or a $C_{1-5}$-alkyloxycarbonyloxy group;

$R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkyloxycarbonyl, aminocarbonyl, $C_{1-3}$-alkylaminocarbonyl, di-($C_{1-3}$-alkyl)-aminocarbonyl, $C_{4-6}$-cycloalkyleneiminocarbonyl, amino, $C_{1-3}$-alkylamino, di-($C_{1-3}$-alkyl)-amino, $C_{1-3}$-alkylcarbonylamino, $C_{1-3}$-alkylsulphonylamino group, with the proviso that the replacement of hydrogen atoms of the first carbon atom of the straight-chain or branched $C_{1-4}$-alkyl group by substituents from the group comprising oxygen, sulphur or nitrogen is excluded, a phenyl, phenyl-$C_{1-2}$-alkyl, heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, B denotes a group of formula

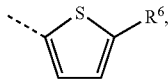

$R^6$ denotes a hydrogen, a chlorine or bromine atom, an ethynyl, a methyl or a methoxy group, while the alkyl, alkenyl, alkynyl and alkoxy groups which have more than two carbon atoms may be straight-chain or branched and the alkyl groups in dialkylated groups may be identical or different, and the hydrogen atoms of the methyl or ethyl groups may be wholly or partly replaced by fluorine atoms, or a tautomer or salt thereof.

6. A compound of the formula I according to claim 1, wherein:

A denotes a 5- to 6-membered cycloalkyleneiminocarbonyl or cycloalkyleneiminosulphonyl group, while the cycloalkyleneimino moiety may be substituted in the carbon skeleton by one or two $C_{1-3}$-alkyl, hydroxy-$C_{1-3}$-alkyl, $C_{1-3}$-alkyloxy-$C_{1-3}$-alkyl, pyridinyl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-5}$-alkyl, N-pyrrolidinyl-$C_{1-3}$-alkyl, $C_{1-3}$-alkyloxycarbonyl-$C_{1-3}$-alkyl, $C_{1-3}$-alkyloxycarbonyl, aminocarbonyl, $C_{1-3}$-alkylaminocarbonyl, di-($C_{1-3}$-alkyl)-aminocarbonyl, hydroxy, $C_{1-3}$-alkyloxy, $C_{1-3}$-alkylamino, di-($C_{1-3}$-alkyl)-amino, N—($C_{1-3}$-alkyl)-piperazin-4-yl-$C_{1-3}$-alkyl, a phenyl or a pyridinyl group, with the proviso that in the substitution of a methylene group adjacent to the imino group two heteroatoms are separated from one another by at least two carbon atoms, and/or a methylene group in the 3-position of a 5-membered cycloalkyleneimino group may be replaced by a sulphur atom or a methylene group in the 4-position of a 6- to 7-membered cycloalkyleneimino group may be replaced by an oxygen or sulphur atom, by an —NH group optionally substituted by a $C_{1-3}$-alkyl, hydroxy, formyl or $C_{1-3}$-alkylcarbonyl group, while additionally a methylene group adjacent to the optionally substituted —NH group may be replaced by a carbonyl group, with the proviso that in the substitution of the 6- to 7-membered cycloalkyleneimino groups wherein a methylene group is replaced by an oxygen or sulphur atom, two heteroatoms are separated from one another by at least two carbon atoms, or A denotes a group of formula

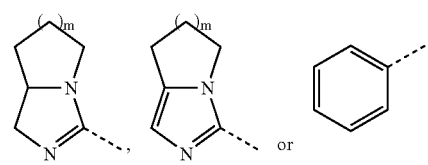

which may be substituted in each case at a carbon atom by a $C_{1-3}$-alkyl, methylsulphonylmethyl, aminosulphonyl, amino-$C_{1-3}$-alkyl, $C_{1-3}$-alkylamino-$C_{1-3}$-alkyl or a di-($C_{1-3}$-alkyl)-amino-$C_{1-3}$-alkyl group and wherein m denotes the number 1 or 2, $R^1$ denotes a hydrogen, fluorine, chlorine or bromine atom, a methyl, trifluoromethyl or methoxy group, $R^2$ denotes a hydrogen atom, X denotes a nitrogen atom or a CH— group, $R^3$ denotes a hydrogen atom or a methyl group, $R^4$ denotes a hydrogen atom, $R^5$ denotes a hydrogen atom, a hydroxy group, an $OR^9$ group, an allyl or methallyl group, a methyl group which may optionally be substituted by a $C_{1-3}$-alkyl, hydroxy, $OR^9$ group, aminocarbonyl, pyridin-4-yl, pyridin-3-yl, pyridin-2-yl, pyrazin-2-yl, pyrazin-3-yl or phenyl group, or a phenyl group, $R^9$ denotes a straight-chain or branched $C_{1-4}$-alkyl group, which may optionally be substituted by a hydroxy, a $C_{1-3}$-alkoxy group, a benzyloxy or a di-($C_{1-3}$-alkyl)-amino group, with the proviso that the replacement of hydrogen atoms of the first carbon atom of the straight-chain or branched $C_{1-4}$-alkyl group by substituents from the group oxygen or nitrogen is excluded, B denotes a group of formula

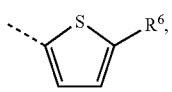

$R^6$ denotes a chlorine or bromine atom or an ethynyl group, while the alkyl, alkenyl, alkynyl and alkoxy groups which have more than two carbon atoms may be straight-chain or branched and the alkyl groups in dialkylated groups may be identical or different, and the hydrogen atoms of the methyl or ethyl groups may be wholly or partly replaced by fluorine atoms, or a tautomer or salt thereof.

7. A compound of the formula I according to claim 1, wherein the group B denotes the group

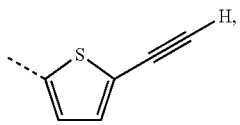

or a tautomer or salt thereof.

8. A compound of the formula I according to claim 1, wherein the group B denotes the group

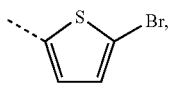

or a tautomer or salt thereof.

9. A compound of the formula I according to claim 1, wherein the group A denotes the group

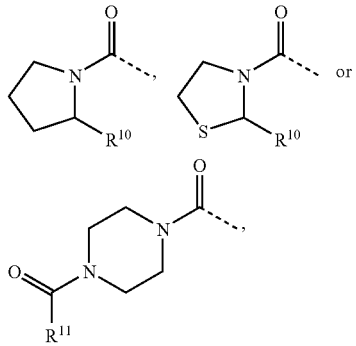

where $R^{10}$ denotes the hydrogen atom, a methyl, aminomethyl, $C_{1-3}$-alkylamino-$C_{1-2}$-alkyl, di-($C_{1-3}$-alkyl)-amino-$C_{1-2}$-alkyl, pyrrolidin-1-yl-methyl or 2-(pyrroldin-1-yl)-ethyl group, $R^{11}$ denotes the hydrogen atom or a methyl group, or a tautomer or salt thereof.

10. A compound of the formula I according to claim 1, wherein the heteroaryl group is monocyclic.

11. A compound of the formula I according to claim 1, wherein the halogen atom is selected from the group consisting of fluorine, chlorine, bromine and iodine.

12. A physiologically acceptable salt of a compound according to claim 1, 2, 3, 4, 5, 6, 7, 8 or 9.

13. A pharmaceutical composition containing a compound according to claim 1, 2, 3, 4, 5, 6, 7, 8 or 9 or a physiologically acceptable salt thereof together with one or more inert carriers and/or diluents.

14. A method for treating a thrombotic condition or reducing the incidence of thrombosis which comprises the administration of an effective amount of a compound according to claim 1, 2, 3, 4, 5, 6, 7, 8 or 9 or a physiologically acceptable salt thereof.

* * * * *